US011465976B2

(12) United States Patent
Sasikumar et al.

(10) Patent No.: US 11,465,976 B2
(45) Date of Patent: *Oct. 11, 2022

(54) 1,2,4-OXADIAZOLE AND THIADIAZOLE COMPOUNDS AS IMMUNOMODULATORS

(71) Applicant: Aurigene Discovery Technologies Limited, Bangalore (IN)

(72) Inventors: Pottayil Govindan N. Sasikumar, Bangalore (IN); Muralidhara Ramachandra, Bangalore (IN); Seetharamaiah Setty Sudarshan Naremaddepalli, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 154 days.

This patent is subject to a terminal disclaimer.

(21) Appl. No.: 16/945,854

(22) Filed: Aug. 1, 2020

(65) Prior Publication Data

US 2020/0361880 A1    Nov. 19, 2020

Related U.S. Application Data

(63) Continuation of application No. 15/556,800, filed as application No. PCT/IB2016/051266 on Mar. 7, 2016, now Pat. No. 10,781,189.

(30) Foreign Application Priority Data

Mar. 10, 2015   (IN) ........................... 1178/CHE/2015
Mar. 10, 2015   (IN) ........................... 1180/CHE/2015

(51) Int. Cl.
| | | |
|---|---|---|
| *A61K 31/4245* | (2006.01) | |
| *C07D 271/06* | (2006.01) | |
| *A61P 35/00* | (2006.01) | |
| *C07D 413/04* | (2006.01) | |
| *C07D 413/06* | (2006.01) | |
| *C07D 413/12* | (2006.01) | |
| *C07D 271/10* | (2006.01) | |
| *C07K 5/087* | (2006.01) | |
| *A61K 38/05* | (2006.01) | |
| *A61K 45/06* | (2006.01) | |
| *C07K 5/065* | (2006.01) | |

(52) U.S. Cl.
CPC ........ *C07D 271/06* (2013.01); *A61K 31/4245* (2013.01); *A61K 38/05* (2013.01); *A61K 45/06* (2013.01); *A61P 35/00* (2018.01); *C07D 271/10* (2013.01); *C07D 413/04* (2013.01); *C07D 413/06* (2013.01); *C07D 413/12* (2013.01); *C07K 5/06078* (2013.01); *C07K 5/0812* (2013.01)

(58) Field of Classification Search
CPC .... A61K 31/4245; C07D 271/06; A61P 35/00
See application file for complete search history.

(56) References Cited

U.S. PATENT DOCUMENTS

| | | |
|---|---|---|
| 3,227,725 A | 1/1966 | Fernand et al. |
| 5,387,585 A | 2/1995 | Borer et al. |
| 5,665,718 A | 9/1997 | Godel et al. |
| 8,735,553 B1 | 5/2014 | Li et al. |
| 9,771,338 B2 | 9/2017 | Sasikumar et al. |
| 10,173,989 B2 | 1/2019 | Sasikumar et al. |
| 10,590,093 B2 | 3/2020 | Sasikumar et al. |
| 10,781,189 B2* | 9/2020 | Sasikumar ........... C07D 413/04 |
| 10,961,205 B2 | 3/2021 | Sasikumar et al. |
| 11,040,948 B2 | 6/2021 | Yu |
| 11,136,300 B2 | 10/2021 | Sasikumar et al. |
| 2005/0272779 A1 | 12/2005 | Edwards et al. |
| 2007/0197522 A1 | 8/2007 | Edwards et al. |
| 2007/0225332 A1 | 9/2007 | Gu et al. |
| 2009/0099227 A1 | 4/2009 | Fyfe et al. |
| 2011/0275673 A1 | 11/2011 | Xiang et al. |
| 2013/0022629 A1 | 1/2013 | Sharpe et al. |
| 2014/0199334 A1 | 7/2014 | Sasikumar et al. |
| 2014/0235620 A1 | 8/2014 | Caferro et al. |
| 2015/0073042 A1 | 3/2015 | Sasikumar et al. |
| 2020/0061030 A1 | 2/2020 | Sasikumar et al. |
| 2020/0239422 A1 | 7/2020 | Sasikumar et al. |
| 2020/0247766 A1 | 8/2020 | Yu |
| 2020/0289477 A1 | 9/2020 | Sasikumar et al. |
| 2020/0368210 A1 | 11/2020 | Sasikumar et al. |
| 2021/0380544 A1 | 12/2021 | Yu |
| 2022/0048875 A1 | 2/2022 | Sasikumar et al. |

FOREIGN PATENT DOCUMENTS

| | | |
|---|---|---|
| JP | 2016532710 A | 10/2016 |
| KR | 20160081897 A | 7/2016 |
| WO | 2001014557 A1 | 3/2001 |

(Continued)

OTHER PUBLICATIONS

Anderson et al., "Lag-3, Tim-3, and TIGIT: Co-inhibitory Receptors with Specialized Functions in Immune Regulation," Immunity, 44(5): 989-1004 (2016).
Ardestani et al., "Cell death features induced in Leishmania major by 1,3,4-thiadiazole derivatives," Exp Parasitol, 132(2): 116-122 (2012).
Borg et al., "1,2,4-Oxadiazole Derivatives of Phenylalnine: Potential Inhibitors of Substance P Endopeptidase," Eur. J. Med. Chem., 28(10):801-810 (1993).
Brittain. "Polymorphism in pharmaceutical solids," edited by H.G Brittain, D.J.W. Grant (chapter 1) p. 1-10 and J.K. Guillory (Chapter 5) p. 183-226 (1999).
Byrn et al., Pharmaceutical Solids: A Strategic Approach to Regulatory Considerations, Pharmaceutical Research, 12(7):945-954 (1995).
CAS Registry No. 1252104-30-5 (2013).
CAS Registry No. 1356744-17-6 (2012).

(Continued)

*Primary Examiner* — Theodore R. Howell
(74) *Attorney, Agent, or Firm* — Benjamin Aaron Adler

(57) ABSTRACT

The present invention relates to 1,2,4-oxadiazole and thiadiazole compounds of formula (I) and their use to inhibit the programmed cell death 1 (PD1) signaling pathway and/or for treatment of disorders by inhibiting an immunosuppressive signal induced by PD-1, PD-L1 or PD-L2.

30 Claims, No Drawings

(56) References Cited

FOREIGN PATENT DOCUMENTS

| | | |
|---|---|---|
| WO | 2002079499 A1 | 10/2002 |
| WO | 2002086083 A2 | 10/2002 |
| WO | 2003042402 A2 | 5/2003 |
| WO | 03070711 A1 | 8/2003 |
| WO | 2004004771 A1 | 1/2004 |
| WO | 2004056875 A1 | 7/2004 |
| WO | 2005056550 A2 | 6/2005 |
| WO | 2006121168 A1 | 11/2006 |
| WO | 2006133216 A2 | 12/2006 |
| WO | 2007075749 A2 | 7/2007 |
| WO | 2008011557 A2 | 1/2008 |
| WO | 2008039431 A2 | 4/2008 |
| WO | 2008156712 A1 | 12/2008 |
| WO | 2009006555 A2 | 1/2009 |
| WO | 2009059162 A2 | 5/2009 |
| WO | 2009105712 A1 | 8/2009 |
| WO | 2010051447 A1 | 5/2010 |
| WO | 2010077634 A1 | 7/2010 |
| WO | 2011066389 A1 | 6/2011 |
| WO | 2011082400 A2 | 7/2011 |
| WO | 2011137587 A1 | 11/2011 |
| WO | 2011161699 A2 | 12/2011 |
| WO | 2012129564 A2 | 9/2012 |
| WO | 2012168944 A1 | 12/2012 |
| WO | 2013132317 A1 | 9/2013 |
| WO | 2013144704 A1 | 10/2013 |
| WO | 2014055897 A2 | 4/2014 |
| WO | 2014059173 A2 | 4/2014 |
| WO | 2014100079 A1 | 6/2014 |
| WO | 2014110298 A1 | 7/2014 |
| WO | 2014141104 A1 | 9/2014 |
| WO | 2014147586 A1 | 9/2014 |
| WO | 2015033299 A1 | 3/2015 |
| WO | 2015033301 A1 | 3/2015 |
| WO | 2016073470 A1 | 5/2016 |
| WO | 2016142833 A1 | 9/2016 |
| WO | 2016142852 A1 | 9/2016 |
| WO | 2016142886 A2 | 9/2016 |
| WO | 2018047143 A1 | 3/2018 |
| WO | 2018073754 A1 | 4/2018 |
| WO | 2019067678 A1 | 4/2019 |
| WO | 2019087087 A1 | 5/2019 |

OTHER PUBLICATIONS

CAS Registry No. 146429-76-5 (2013).
CAS Registry No. 1494629-78-5 (2013).
CAS Registry No. 1496514-97-6 (2013).
CAS Registry No. 1496518-51-4 (2013).
CAS Registry No. 1557852-63-7 (2014).
CAS Registry No. 1848907-06-1 (2016).
CAS Registry No. 1848909-97-6 (2016).
CAS Registry No. 1857027-85-0 (2016).
CAS Registry No. 1868314-35-5 (2016).
CAS Registry No. 1868388-36-6 (2016).
CAS Registry No. 1868393-26-3 (2016).
CAS Registry No. 1869758-25-7 (2016).
CAS Registry No. 1870159-31-1 (2016).
CAS Registry No. 1875311-16-2 (2016).
CAS Registry No. 1875758-09-0 (2016).
CAS Registry No. 1878569-90-4 (2016).
CAS Registry No. 876710-85-9 (2006).
Database Registry Chemical Abstracts, STN Accession No. 172410-37-6.
Database Registry Chemical Abstracts, STN Accession No. 197083-27-5.
Extended European Search Report for EP Application No. 16761169.8 dated Jul. 2, 2019.
Extended European Search Report for EP Application No. 16761184 dated Jun. 26, 2018.
Extended European Search Report for EP Application No. 17862427.6 dated Jun. 5, 2020.
Extended European Search Report for European Application No. 18162983.3 dated Jun. 27, 2018.
Graham, Clinical Trials of HIV Vaccines, HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.
Guo et al., Design of oxobenzimidazoles and oxindoles as novel androgen receptor antagonists, Bioorg Med Chem Letts 22(7):2572-2578 (2012).
Harvey, Immunologic and Clinical Effects of Targeting PD-1 in Lung Cancer, Nature, 96: 214-223 (2014).
International Preliminary Report on Patentability for International Application No. PCT/IB2018/058526 dated May 14, 2020.
International Search Report and Written Opinion for International Application No. PCT/CN2017/104485 dated Jun. 29, 2018.
International Search Report and Written Opinion for International Application No. PCT/IB2014/064279 dated Dec. 12, 2014.
International Search Report and Written Opinion for International Application No. PCT/IB2016/051266 dated Jul. 8, 2016.
International Search Report and Written Opinion for International Application No. PCT/IB2016/051343 dated Jul. 28, 2016.
International Search Report and Written Opinion for International Application No. PCT/IB2017/056462 dated Jan. 10, 2018.
International Search Report Written Opinion for International Application No. PCT/US2018/053052 dated Jan. 29, 2019.
Jin, Role of PD-1 in Regulating T-Cell Immunity, Current Topics in Microbiology and Immunology, 350: 17-37 (2010).
Lazorchak et al., Abstract A36: CA-170, an oral small molecule PD-L1 and VISTA immune checkpoint antagonist, promotes T cell immune activation and inhibits tumor growth in pre-clinical models of cancer, Cancer Immunology Research, 5(S3):A36 (2017).
Liu et al., Immune-checkpoint proteins VISTA and PD-1 nonredundantly regulate murine T-cell responses, PNAS, 112(21): 6682-6687 (2015).
Luo et al., Principles of Cancer Therapy: Oncogene and Non-oncogene Addiction, Cell, 136(5): 823-837 (2009).
Marechal et al., 1,2,4-oxadiazoles identified by virtual screening and their non-covalent inhibition of the human 20S proteasome, Curr Med Chem 20(18):2351-2362 (2013).
Moussebois et al., Synthese de Deux Nouveaux Acides Amines Phenoliques Comportant un Cycle 1,2,4-Oxadiazole, Helv. Chim. ACTA, 60(1):237-242 (1977).
Ozcan et al., Oxadiazole-Isopropylamieds as Potent and Noncovalent Proteasome Inhibitors, J. Med. Chem., 56(10):3783-3805 (2013).
Palazzo et al., 1,2,4-Oxadiazoles—IV. Synthesis and Pharmacological Properties of a Series of Substituted Aminoalkyl- 1,2,4-Oxadiazoles, J. Med. Chem., 351-367 (1961).
Patwardhan et al., Structure—Activity Relationship Studies and in Vivo Activity of Guanidine-Based Sphingosine Kinase Inhibitors: Discovery of SphK1- and SphK2—Selective Inhibitors, J. Med Chem., 58(4):1879-1899 (2015).
Pedoeem et al., Programmed Death—1 Pathway in Cancer and Autoimmunity, Clinical Immunology, 153: 145-152 (2014).
Shi et al., The Role of PD-1 and PD-L1 in T-cell Immune Suppression in Patients with Hematological Malignancies, Journal of Hematology & Oncology, 6(74): 1-6 (2013).
Sureshbabu et al., Synthesis of 1,2,4-oxadiazole-linked Orthogonally Urethane—Protected Dipeptide Mimetics, Tetrahedron Letters, 49(35): 5133-5136 (2008).
Waldmann, Effective Cancer Therapy Through Immunomodulation, T Annu Rev Med, 57: 65-81 (2006).
Berge et al., "Pharmaceutical Salts," Journal of Pharmaceutical Sciences, 66(1):1-19 (1977).
Censi et al., "Polymorph Impact on the Bioavailability and Stability of Poorly Soluble Drugs," Molecules, 20(10): 18759-18776 (2015).
Clinical Trial NCT 02812875., "A Study of CA-170 (Oral PD-L1, PD-L2 and VISTA Checkpoint Antagonist) in Patients With Advanced Tumors and Lymphomas," U.S. National Library of Medicine: 7 pages (2016).
Clinical Trial NCT02671955., "A Study of Safety, Pharmacokinetics, Pharmacodynamics of JNJ-61610588 in Participants With Advanced Cancer," U.S. National Library of Medicine: 9 pages (2016).

(56) References Cited

OTHER PUBLICATIONS

Dempke et al., "Second-and third-generation drugs for immuno-oncology treatment—The more the better?" Eur J Cancer, 74: 55-72 (2017).
Extended European Search Report for EP Application No. EP/US18/18863750 dated May 31, 2021.
Lee "A practical guide to pharmaceutical polymorph screening & selection," Asian J Pharm Sci, 9(4): 163-175 (2014).
Newman "Specialized Solid Form Screening Techniques," Org Process Res Dev, 13(3): 457-471 (2012).
Rietz et al., "Fragment-Based Discovery of Small Molecules Bound to T-Cell Immunoglobulin and Mucin Domain-Containing Molecule 3 (TIM-3)," J Med Chem, 64: 14757-14772 (2021).
Sasikumar et al., "PD-1 derived CA-170 is an oral immune checkpoint inhibitor that exhibits preclinical anti-tumor efficacy," Communications Biology, 4: 12 pages (2021).
Wu et al., "VISTA inhibitors in cancer immunotherapy: a short perspective on recent progresses," RSC Med Chem, 12: 1672-1679 (2021).

* cited by examiner

1,2,4-OXADIAZOLE AND THIADIAZOLE COMPOUNDS AS IMMUNOMODULATORS

This application is a continuation under 35 U.S.C. § 120 of pending application U.S. Ser. No. 15/556,800, filed Sep. 8, 2017, which is a national stage application under 35 U.S.C. § 371, filed Mar. 7, 2016, now abandoned, which claims the benefit of Indian provisional application number 1180/CHE/2015, filed on Mar. 10, 2015, now abandoned, and Indian provisional application number 1178/CHE/2015, filed on Mar. 10, 2015, now abandoned; the specifications of all of which are hereby incorporated by reference in their entireties.

TECHNICAL FIELD

The present invention relates to 1,2,4-oxadiazole and thiadiazole compounds and their derivatives therapeutically useful as immune modulators. The invention also relates to pharmaceutical compositions comprising 1,2,4-oxadiazole and thiadiazole compounds and their derivatives.

BACKGROUND OF THE INVENTION

Programmed cell death-1 (PD-1) is a member of the CD28 superfamily that delivers negative signals upon interaction with its two ligands, PD-1 or PD-L2. PD-1 and its ligands are broadly expressed and exert a wider range of immunoregulatory roles in T cells activation and tolerance compared with other CD28 members. PD-1 and its ligands are involved in attenuating infectious immunity and tumor immunity and facilitating chronic infection and tumor progression. The biological significance of PD-1 and its ligand suggests the therapeutic potential of manipulation of PD-1 pathway against various human diseases (Hyun-Tak Jin, et al., Curr Top Microbiol Immunol. (2011); 350:17-37).

T-cell activation and dysfunction relies on direct and modulated receptors. Based on their functional outcome, co-signaling molecules can be divided as co-stimulators and co-inhibitors, which positively and negatively control the priming, growth, differentiation and functional maturation of a T-cell response (Li Shi, et al., Journal of Hematology & Oncology 2013, 6:74).

Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of clinical trials (RD Harvey, Clinical Pharmacology & Therapeutics (2014); 96 2, 214-223).

Programmed death-1 (PD-1) is a co-receptor that is expressed predominantly by T cells. The binding of PD-1 to its ligands, PD-L1 or PD-L2, is vital for the physiological regulation of the immune system. A major functional role of the PD-1 signaling pathway is the inhibition of self-reactive T cells, which serve to protect against autoimmune diseases. Elimination of the PD-1 pathway can therefore result in the breakdown of immune tolerance that can ultimately lead to the development of pathogenic autoimmunity. Conversely, tumor cells can at times co-opt the PD-1 pathway to escape from immunosurveillance mechanisms. Therefore, blockade of the PD-1 pathway has become an attractive target in cancer therapy. Current approaches include six agents that are either PD-1 and PD-L1 targeted neutralizing antibodies or fusion proteins. More than forty clinical trials are underway to better define the role of PD-1 blockade in variety of tumor types (Ariel Pedoeem et al., Clinical Immunology (2014), 153(1), 145-152).

International applications WO2002086083, WO2004004771, WO2004056875, WO2006121168, WO2008156712, WO2010077634, WO2011066389, WO2014055897 and WO2014100079 report PD-1, PD-L1 inhibitory antibodies and/or methods of identifying such antibodies. Further, US patents such as U.S. Pat. Nos. 8,735,553 and 8,168,757 report PD-1 or PD-L1 inhibitory antibodies and/or fusion proteins.

Furthermore, International applications, WO2011161699, WO2012168944, WO2013144704 and WO2013132317 report peptides or peptidomimetic compounds which are capable of suppressing and/or inhibiting the programmed cell death 1 (PD1) signaling pathway.

Still there is a need for more potent, better and/or selective immune modulators of the PD-1 pathway.

SUMMARY OF INVENTION

The present invention provides 1,2,4-oxadiazole and thiadiazole compounds and their pharmaceutically acceptable salts or stereoisomers. These compounds are capable of suppressing and/or inhibiting the programmed cell death 1 (PD1) signalling pathway.

In one aspect, the present invention provides 1,2,4-oxadiazole and thiadiazole compounds of formula (I):

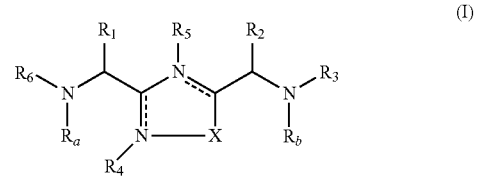

or a pharmaceutically acceptable salt or a stereoisomer thereof; wherein,
----- is an optional double bond;
X is O or S;
$R_1$ and $R_2$ independently are a side chain of an amino acid or hydrogen, ($C_1$-$C_6$)alkyl, ($C_2$-$C_6$)alkenyl, ($C_2$-$C_6$)alkynyl or cycloalkyl; wherein ($C_1$-$C_6$)alkyl, ($C_2$-$C_6$)alkenyl, ($C_2$-$C_6$)alkynyl and cycloalkyl are optionally substituted by one or more substituents selected from amino, alkylamino, acylamino, carboxylic acid, carboxylate, carboxylic acid ester, thiocarboxylate, thioacid, —$CONR_7R_8$, hydroxy, cycloalkyl, (cycloalkyl)alkyl, aryl, arylalkyl, heterocyclyl, (heterocyclyl)alkyl, heteroaryl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl and optionally wherein two or three carbon atoms of the ($C_1$-$C_6$)alkyl, ($C_2$-$C_6$)alkenyl or ($C_2$-$C_6$)alkynyl form part of a 3-7-membered carbocyclic or heterocyclic ring (such as a cyclobutyl or oxirane ring);
$R_3$ is hydrogen, —CO-[Aaa1]$_m$, [Aaa1]$_m$, [Aaa1]$_m$—CO-[Aaa1]$_m$, —S(O)$_p$-[Aaa1]$_m$, —$CONR_7R_8$, —$COR_c$, —$SO_2R_c$, ($C_1$-$C_6$)alkyl, ($C_2$-$C_6$)alkenyl or ($C_2$-$C_6$)alkynyl; wherein ($C_1$-$C_6$)alkyl, ($C_2$-$C_6$)alkenyl and ($C_2$-$C_6$)alkynyl are optionally substituted by one or more substituents selected from amino, alkylamino, acylamino, —COO-alkyl, carboxylic acid, carboxylate, thiocarboxylate, thioacid, —$CONR_7R_8$, hydroxy, aryl, arylalkyl, cycloalkyl, heterocyclyl, heteroaryl, (cycloalkyl)alkyl, (heterocyclyl)alkyl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl, optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_4$ and $R_5$ independently are hydrogen or absent;

$R_6$ is hydrogen, alkyl, alkenyl, alkynyl, aralkyl, aryl, heteroaralkyl, heteroaryl, cycloalkyl, (cycloalkyl)alkyl, amino, aminoalkyl, hydroxyalkyl, alkoxyalkyl, acyl, $[Aaa2]_n$, —CO-$[Aaa2]_n$, $[Aaa2]_n$—CO-$[Aaa2]_n$ or —S(O)$_p$-$[Aaa2]_n$;

$R_7$ and $R_8$ independently are hydrogen, $(C_1-C_6)$alkyl, $(C_2-C_6)$alkenyl, $(C_2-C_6)$alkynyl, aryl or heterocyclyl; wherein $(C_1-C_6)$alkyl, $(C_2-C_6)$alkenyl and $(C_2-C_6)$alkynyl, aryl and heterocyclyl are optionally substituted by one or more substituents selected from halogen, hydroxyl, amino, nitro, cyano, cycloalkyl, heterocyclyl, heteroaryl, aryl, guanidino, (cycloalkyl)alkyl, (heterocyclyl)alkyl and (heteroaryl)alkyl; optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

alternatively $R_7$ and $R_8$ together with the nitrogen to which they are attached form an optionally substituted 3-7-membered ring containing 0-2 additional heteroatoms independently selected from N, O and S in any stable combination; wherein the optional substituent at each occurrence is selected from hydroxyl, —COOH, —COO-alkyl, amide, halo, amino, nitro and cyano;

[Aaa1] and [Aaa2], independently for each occurrence, represents an amino acid residue; wherein a C-terminal carboxyl group of amino acid residue is a free C-terminal carboxyl group (—COOH) or a modified C-terminal carboxyl group and an N-terminal amino group of amino acid residue is a free N-terminus (—NH$_2$) or a modified N-terminal amino group;

$R_a$ is hydrogen or alkyl, alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl; $R_b$ is hydrogen or alkyl, alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl; or $R_b$ and $R_2$, together with the atoms to which they are attached, may form pyrrolidine or piperidine optionally substituted with one or more groups independently selected from hydroxyl, halo, amino, cyano and alkyl;

$R_c$ is $(C_1-C_6)$alkyl, cycloalkyl, aryl, heterocyclyl or heteroaryl; wherein the said $(C_1-C_6)$alkyl, cycloalkyl, aryl, heterocyclyl or heteroaryl is optionally substituted by one or more substituents selected from carboxylic acid, hydroxyl, alkyl, alkoxy, amino, alkylamino, acylamino, carboxylic ester, cycloalkyl, heterocyclyl, heteroaryl, (cycloalkyl)alkyl, (heterocyclyl)alkyl or (heteroaryl)alkyl;

m and n independently are integers selected from 1 to 3; p is an integer selected from 1 to 2;

with a proviso that $R_1$ is not a side chain of Ser or Thr, when $R_2$ is a side chain of Asp, Asn, Glu or Gln, $R_3$ is hydrogen, —CO-Ser or —CO-Thr, $R_6$ is hydrogen, alkyl or acyl and $R_a$ and $R_b$ are hydrogen.

In another aspect, the present invention relates to a process for preparation of compounds of formula (I) or a pharmaceutically acceptable salt or a stereoisomer thereof.

In a further aspect, the present invention relates to pharmaceutical compositions comprising a compound of formula (I) or a pharmaceutically acceptable salt or a stereoisomer thereof and processes for preparing such compositions.

Yet another aspect of the present invention provides methods of administering a compound of formula (I) or a pharmaceutically acceptable salt or a stereoisomer, to suppress and/or inhibit the programmed cell death 1 (PD1) signaling pathway. For example, these compounds can be used to treat one or more diseases characterized by aberrant or undesired activity of the PD1 signaling pathway.

DETAILED DESCRIPTION OF THE INVENTION

The present invention provides 1,2,4-oxadiazole and thiadiazole compounds and their derivatives as therapeutic agents useful for treatment of disorders via immunopotentiation comprising inhibition of immunosuppressive signal induced due to PD-1, PD-1 or PD-L2 and therapies using them.

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus it is intended that the present invention include such modifications and variations and their equivalents. Other objects, features and aspects of the present invention are disclosed in or are obvious from, the following detailed description. It is to be understood by one of ordinary skill in the art that the present discussion is a description of exemplary embodiments only and is not to be construed as limiting the broader aspects of the present invention.

In certain embodiments, the present invention provides compounds of formula (I):

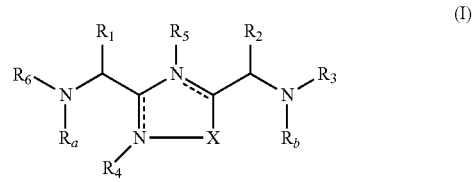

or a pharmaceutically acceptable salt or a stereoisomer thereof; wherein,

----- is an optional double bond;

X is O or S;

$R_1$ and $R_2$ independently are a side chain of an amino acid or hydrogen, $(C_1-C_6)$alkyl, $(C_2-C_6)$alkenyl, $(C_2-C_6)$alkynyl or cycloalkyl; wherein $(C_1-C_6)$alkyl, $(C_2-C_6)$alkenyl, $(C_2-C_6)$alkynyl and cycloalkyl are optionally substituted by one or more substituents selected from amino, alkylamino, acylamino, carboxylic acid, carboxylate, carboxylic acid ester, thiocarboxylate, thioacid, —CONR$_7$R$_8$, hydroxy, cycloalkyl, (cycloalkyl)alkyl, aryl, arylalkyl, heterocyclyl, (heterocyclyl)alkyl, heteroaryl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl and optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_3$ is hydrogen, —CO-[Aaa1]$_m$, [Aaa1]$_m$, [Aaa1]$_m$—CO-[Aaa1]$_m$, —S(O)$_p$-[Aaa1]$_m$, —CONR$_7$R$_8$, —COR$_c$, —SO$_2$R$_c$, $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are optionally substituted by one or more substituents selected from amino, alkylamino, acylamino, —COO-alkyl, carboxylic acid, carboxylate, thiocarboxylate, thioacid, —CONR$_7$R$_8$, hydroxy, aryl, arylalkyl, cycloalkyl, heterocyclyl, heteroaryl, (cycloalkyl)alkyl, (heterocyclyl)alkyl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl, optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_4$ and $R_5$ independently are hydrogen or absent;

$R_6$ is hydrogen, alkyl, alkenyl, alkynyl, aralkyl, aryl, heteroaralkyl, heteroaryl, cycloalkyl, (cycloalkyl)alkyl, amino, aminoalkyl, hydroxyalkyl, alkoxyalkyl, acyl, [Aaa2]$_n$, —CO-[Aaa2]$_n$, [Aaa2]$_n$—CO-[Aaa2]$_n$ or —S(O)$_p$-[Aaa2]$_n$;

$R_7$ and $R_8$ independently are hydrogen, $(C_1-C_6)$alkyl, $(C_2-C_6)$alkenyl, $(C_2-C_6)$alkynyl, aryl or heterocyclyl; wherein $(C_1-C_6)$alkyl, $(C_2-C_6)$alkenyl and $(C_2-C_6)$alkynyl, aryl and heterocyclyl are optionally substituted by one or more substituents selected from halogen, hydroxyl, amino, nitro, cyano, cycloalkyl, heterocyclyl, heteroaryl, aryl, guanidino, (cycloalkyl)alkyl, (heterocyclyl)alkyl and (heteroaryl)alkyl; optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

alternatively $R_7$ and $R_8$ together with the nitrogen to which they are attached form an optionally substituted 3-7-membered ring containing 0-2 additional heteroatoms independently selected from N, O and S in any stable combination; wherein the optional substituent at each occurrence is selected from hydroxyl, —COOH, —COO-alkyl, amide, halo, amino, nitro and cyano;

[Aaa1] and [Aaa2], independently for each occurrence, represents an amino acid residue; wherein a C-terminal carboxyl group of amino acid residue is a free C-terminal carboxyl group (—COOH) or a modified C-terminal carboxyl group and an N-terminal amino group of amino acid residue is a free N-terminus (—NH$_2$) or a modified N-terminal amino group;

$R_a$ is hydrogen or alkyl, alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl; $R_b$ is hydrogen or alkyl, alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl; or $R_b$ and $R_2$, together with the atoms to which they are attached, may form pyrrolidine or piperidine optionally substituted with one or more groups independently selected from hydroxyl, halo, amino, cyano and alkyl;

$R_c$ is $(C_1-C_6)$alkyl, cycloalkyl, aryl, heterocyclyl or heteroaryl; wherein the said $(C_1-C_6)$alkyl, cycloalkyl, aryl, heterocyclyl or heteroaryl is optionally substituted by one or more substituents selected from carboxylic acid, hydroxyl, alkyl, alkoxy, amino, alkylamino, acylamino, carboxylic ester, cycloalkyl, heterocyclyl, heteroaryl, (cycloalkyl)alkyl, (heterocyclyl)alkyl or (heteroaryl)alkyl;

m and n independently are integers selected from 1 to 3;

p is an integer selected from 1 to 2;

with a proviso that $R_1$ is not a side chain of Ser or Thr, when $R_2$ is a side chain of Asp, Asn, Glu or Gln, $R_3$ is hydrogen, —CO-Ser or —CO-Thr, $R_6$ is hydrogen, alkyl or acyl and $R_a$ and $R_b$ are hydrogen.

In certain embodiments of the compound of formula (I): or a pharmaceutically acceptable salt or a stereoisomer thereof; wherein, ----- is an optional double bond;

X is O or S;

$R_1$ and $R_2$ independently are a side chain of an amino acid or hydrogen, $(C_1-C_6)$alkyl, $(C_2-C_6)$alkenyl, $(C_2-C_6)$alkynyl or cycloalkyl; wherein $(C_1-C_6)$alkyl, $(C_2-C_6)$alkenyl, $(C_2-C_6)$alkynyl and cycloalkyl are optionally substituted by one or more substituents selected from amino, alkylamino, acylamino, carboxylic acid, carboxylate, thiocarboxylate, thioacid, —CONR$_7$R$_8$, hydroxy, cycloalkyl, (cycloalkyl)alkyl, aryl, heterocyclyl, heteroaryl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl;

$R_3$ is hydrogen, —CO-[Aaa1]$_m$, [Aaa1]$_m$, [Aaa1]$_m$—CO-[Aaa1]$_m$, —S(O)$_p$-[Aaa1]$_m$, —CONR$_7$R$_8$, —COR$_c$, —SO$_2$R$_c$, $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are optionally substituted by one or more substituents selected from amino, alkylamino, acylamino, carboxylic acid, carboxylate, thiocarboxylate, thioacid, —CONR$_7$R$_8$, hydroxy, cycloalkyl, aryl, heterocyclyl, heteroaryl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl;

$R_4$ and $R_5$ independently are hydrogen or absent;

$R_6$ is hydrogen, alkyl, acyl, [Aaa2]$_n$, —CO-[Aaa2]$_n$, [Aaa2]$_n$—CO-[Aaa2]$_n$ or —S(O)$_p$-[Aaa1]$_n$;

$R_7$ and $R_8$ independently are hydrogen, $(C_1-C_8)$alkyl, $(C_2-C_6)$alkenyl, $(C_2-C_6)$alkynyl, aryl or heterocyclyl; wherein $(C_1-C_6)$alkyl, $(C_2-C_6)$alkenyl and $(C_2-C_6)$alkynyl, aryl and heterocyclyl are optionally substituted by one or more substituents selected from halogen, hydroxyl, amino, nitro, cyano, cycloalkyl, heterocyclyl, heteroaryl, aryl, guanidino, (cycloalkyl)alkyl, (heterocyclyl)alkyl and (heteroaryl)alkyl; optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

alternatively $R_7$ and $R_8$ together with the nitrogen to which they are attached form an optionally substituted 3-7-membered ring containing 0-2 additional heteroatoms independently selected from N, O and S in any stable combination; wherein the optional substituent at each occurrence is selected from hydroxyl, —COOH, —COO-alkyl, amide, halo, amino, nitro and cyano;

each of [Aaa1] and [Aaa2] is independently selected amino acid residues; wherein C-terminal carboxyl group of amino acid residue is a free C-terminal carboxyl group (—COOH) or a modified C-terminal carboxyl group and N-terminal amino group of amino acid residue is a free N-terminus (—NH$_2$) or a modified N-terminal amino group;

$R_a$ is hydrogen or alkyl;

$R_b$ is hydrogen or alkyl; or $R_b$ and $R_2$, together with the atoms to which they are attached, may form pyrrolidine or piperidine optionally substituted with one or more groups independently selected from hydroxyl, halo, amino, cyano and alkyl;

$R_c$ is $(C_1-C_6)$alkyl, cycloalkyl, aryl, heterocyclyl or heteroaryl; wherein the said $(C_1-C_6)$alkyl, cycloalkyl, aryl, heterocyclyl or heteroaryl is optionally substituted by one or more substituents selected from carboxylic acid, hydroxyl, alkyl, alkoxy, amino, alkylamino, acylamino, carboxylic ester, cycloalkyl, heterocyclyl, heteroaryl, (cycloalkyl)alkyl, (heterocyclyl)alkyl or (heteroaryl)alkyl;

m and n independently are integers selected from 1 to 3;

p is an integer selected from 1 to 2;

with a proviso that $R_1$ is not a side chain of Ser or Thr, when $R_2$ is a side chain of Asp, Asn, Glu or Gln, $R_3$ is hydrogen, —CO-Ser or —CO-Thr, $R_6$ is hydrogen, alkyl or acyl and $R_a$ and $R_b$ are hydrogen.

In certain embodiments the compounds of the invention are represented by formula (I),

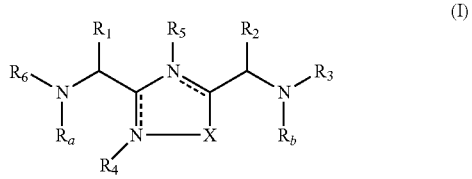

wherein,

X is O or S;

each dotted line [----] independently represents an optional double bond;

$R_a$ and $R_b$ are each independently hydrogen or a substituent, such as alkyl, alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl;

$R_1$ is $(C_1-C_6)$alkyl substituted by one or more substituents selected from amino, alkylamino, acylamino, heterocyclyl, heteroaryl, guanidino, (heterocyclyl)alkyl and (heteroaryl)alkyl, wherein any heterocyclyl or heteroaryl contains at least one nitrogen atom and $R_1$ includes a basic nitrogen atom whose conjugate acid has a pKa above 3, preferably above 5 and optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_2$ is $(C_1-C_6)$alkyl, $(C_2-C_6)$alkenyl or $(C_2-C_6)$alkynyl substituted by one or more substituents selected from carboxylate, carboxylic acid, carboxylic acid ester, thiocarboxylate, thio acid, amido, amino and heterocyclyl, optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_3$ is hydrogen or —CO-Aaa;

Aaa represents an amino acid residue, wherein the amino acid residue comprises a side chain that includes a —OH, —O-acyl, —SH, —NH$_2$ or NH(alkyl) moiety;

each of $R_4$ and $R_5$ independently is hydrogen or absent; and $R_6$ represents hydrogen, alkyl, alkenyl, alkynyl, aralkyl, aryl, heteroaralkyl, heteroaryl, cycloalkyl, (cycloalkyl)alkyl, amino, aminoalkyl, hydroxyalkyl, alkoxyalkyl or acyl;

or a pharmaceutically acceptable salt thereof.

In yet further embodiments of the compound of formula (I):

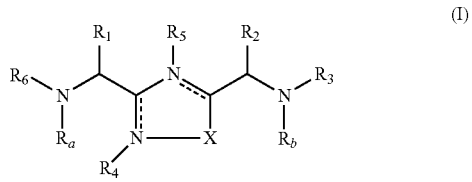

or a pharmaceutically acceptable salt or a stereoisomer thereof; wherein,

----- is an optional double bond;

X is O or S;

$R_1$ and $R_2$ independently are a side chain of an amino acid or $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are substituted by one or more substituents selected from amino, alkylamino, acylamino, —COO— alkyl, cycloalkyl, heterocyclyl, heteroaryl, guanidino, (cycloalkyl)alkyl, (heterocyclyl)alkyl and (heteroaryl)alkyl; optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_3$ is hydrogen —CO-[Aaa], —CONR$_7$R$_8$, $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are substituted by one or more substituents selected from amino, alkylamino, acylamino, —COO-alkyl, cycloalkyl, heterocyclyl, heteroaryl, guanidino, (cycloalkyl)alkyl, (heterocyclyl)alkyl and (heteroaryl)alkyl; optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

$R_4$ and $R_5$ independently are hydrogen or absent;

$R_6$ is hydrogen, alkyl or acyl;

$R_7$ and $R_8$ independently are hydrogen, $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are substituted by one or more substituents selected from halogen, hydroxyl, amino, nitro, cyano, cycloalkyl, heterocyclyl, heteroaryl, guanidino, (cycloalkyl)alkyl, (heterocyclyl)alkyl and (heteroaryl)alkyl; optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

alternatively $R_7$ and $R_8$ together with the nitrogen to which they are attached form an optionally substituted 3-7-membered ring containing 0-2 additional heteroatoms independently selected from N, O and S in any stable combination; wherein the optional substituent at each occurrence is selected from hydroxyl, —COOH, —COO-alkyl, amide, halo, amino, nitro or cyano;

[Aaa] is an amino acid residue;

$R_a$ is hydrogen or alkyl;

$R_b$ is hydrogen or alkyl;

or $R_b$ and $R_2$, together with the atoms to which they are attached, may form pyrrolidine or piperidine optionally substituted with one or more groups independently selected from hydroxyl, halo, amino, cyano and alkyl; and with a proviso that $R_1$ is not the side chain of Ser, Thr, Lys, Arg or His, when $R_2$ is the side chain of Asp, Asn, Glu or Gln, $R_3$ is hydrogen, —CO-Ser or —CO-Thr and $R_a$ and $R_b$ are hydrogen.

In certain preferred embodiments of Formula (I), X is O. In certain such embodiments, the ring containing X is an oxadiazole ring.

In certain embodiments, $R_1$ or $R_2$ represents a side chain of an amino acid. Alternatively, $R_1$ or $R_2$ may represent hydrogen.

In certain embodiments, $R_1$ and $R_2$ may independently represent $(C_1-C_6)$alkyl, $(C_2-C_6)$alkenyl, $(C_2-C_6)$alkynyl or cycloalkyl wherein $(C_1-C_6)$alkyl, $(C_2-C_6)$alkenyl, $(C_2-C_6)$alkynyl and cycloalkyl are substituted by carboxylic acid, carboxylate, carboxylic acid ester, thiocarboxylate, thioacid, —$CONR_7R_8$, hydroxy, cycloalkyl and aryl. In certain such embodiments, $R_1$ and $R_2$ may independently represent $(C_1-C_6)$alkyl, $(C_2-C_6)$alkenyl or $(C_2-C_6)$alkynyl substituted by carboxylic acid ester, thiocarboxylate, thioacid or cycloalkyl.

In certain embodiments, $R_1$ is a side chain of an amino acid or hydrogen, $(C_1-C_6)$alkyl, $(C_2-C_6)$alkenyl, $(C_2-C_6)$alkynyl or cycloalkyl; wherein $(C_1-C_6)$alkyl, $(C_2-C_6)$alkenyl, $(C_2-C_6)$alkynyl and cycloalkyl are optionally substituted by one or more substituents selected from amino, alkylamino, acylamino, carboxylic acid, carboxylate, carboxylic acid ester, thiocarboxylate, thioacid, —$CONR_7R_8$, hydroxy, cycloalkyl, (cycloalkyl)alkyl, aryl, heterocyclyl, (heterocyclyl)alkyl, heteroaryl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl and optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

In certain embodiments, $R_1$ is $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are optionally substituted by one or more substituents selected from amino, alkylamino, acylamino, carboxylic acid, carboxylate, thiocarboxylate, thioacid, —$CONR_7R_8$, hydroxy, cycloalkyl, aryl, heterocyclyl, heteroaryl, guanidino, —SH and —S(alkyl).

In certain embodiments, $R_1$ is $(C_1-C_6)$alkyl, $(C_2-C_6)$alkenyl or $(C_2-C_6)$alkynyl substituted by one or more substituents selected from amino, alkylamino, acylamino, heterocyclyl, heteroaryl and guanidino and is optionally further substituted by one or more substituents such as alkyl, alkoxy, aralkyl or aryl.

In certain embodiments, $R_1$ is $(C_1-C_6)$alkyl, $(C_2-C_6)$alkenyl or $(C_2-C_6)$alkynyl is substituted by amino, alkylamino, acylamino, heterocyclyl, heteroaryl, guanidino, (heterocyclyl)alkyl; wherein (heteroaryl)alkyl, heterocyclyl or heteroaryl contains at least one basic nitrogen atom. A basic nitrogen atom refers to a nitrogen that is protonated and positively charged at pH levels below its $pK_a$ value. For example, the $pK_a$ of the conjugate acid of the nitrogen-containing compound is >5, preferably >7. In certain such embodiments, $R_1$ is optionally further substituted by one or more substituents, such as alkyl, alkoxy, aralkyl or aryl.

In some embodiments, $R_1$ represents $(C_1-C_6)$alkyl, $(C_2-C_6)$alkenyl or $(C_2-C_6)$alkynyl substituted by one or more substituents selected from carboxylate, carboxylic acid, carboxylic acid ester, thiocarboxylate, thio acid, —$CONR_7R_8$, hydroxy, cycloalkyl, aryl, guanidino, —SH and —S(alkyl). In some such embodiments, $R_1$ represents $(C_1-C_6)$alkyl, $(C_2-C_6)$alkenyl or $(C_2-C_6)$alkynyl substituted by one or more substituents selected from carboxylic acid ester, thiocarboxylate, thio acid or cycloalkyl.

In accordance with any of the foregoing embodiments, in certain embodiments, $R_1$ is $(C_1-C_4)$alkyl substituted by one or more substituents selected from amino, heteroaryl or guanidino. In certain embodiments, $R_1$ is —$(CH_2)$imidazolyl, —$(CH_2)_3NHC(=N)$—$NH_2$ or —$(CH_2)_4NH_2$.

In certain embodiments, $R_2$ is a side chain of an amino acid or hydrogen, $(C_1-C_6)$alkyl, $(C_2-C_6)$alkenyl, $(C_2-C_6)$alkynyl or cycloalkyl; wherein $(C_1-C_6)$alkyl, $(C_2-C_6)$alkenyl, $(C_2-C_6)$alkynyl and cycloalkyl are optionally substituted by one or more substituents selected from amino, alkylamino, acylamino, carboxylic acid, carboxylate, carboxylic acid ester, thiocarboxylate, thioacid, —$CONR_7R_8$, hydroxy, cycloalkyl, (cycloalkyl)alkyl, aryl, heterocyclyl, (heterocyclyl)alkyl, heteroaryl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl and optionally wherein two or three carbon atoms of the $(C_1-C_6)$alkyl, $(C_2-C_6)$alkenyl or $(C_2-C_6)$alkynyl form part of a 3-7-membered carbocyclic or heterocyclic ring (such as a cyclobutyl or oxirane ring);

In certain embodiments, $R_2$ is $(C_1-C_6)$alkyl, $(C_2-C_6)$alkenyl or $(C_2-C_6)$alkynyl; wherein $(C_1-C_6)$alkyl, $(C_2-C_6)$alkenyl and $(C_2-C_6)$alkynyl are optionally substituted by one or more substituents selected from amino, alkylamino, acylamino, carboxylic acid, carboxylate, thiocarboxylate, thioacid, —$CONR_7R_8$, hydroxy, cycloalkyl, aryl, heterocyclyl, (heterocyclyl)alkyl, heteroaryl, (heteroaryl)alkyl, guanidino, —SH and —S(alkyl). In some such embodiments, $R_2$ represents $(C_1-C_6)$alkyl, $(C_2-C_6)$alkenyl or $(C_2-C_6)$alkynyl substituted by one or more substituents selected from alkylamino, acylamino, cycloalkyl and (heterocyclyl)alkyl.

In certain embodiments, $R_2$ is $(C_1-C_6)$alkyl substituted by one or more substituents selected from carboxylate, carboxylic acid, carboxylic acid ester, thiocarboxylate, thio acid, amido, amino and heterocyclyl and optionally further substituted by one or more substituents, such as alkyl, alkoxy, aralkyl or aryl. In certain such embodiments, $R_2$ further optionally contains one or more double bonds or triple bonds. In certain embodiments, $R_2$ is $(C_3-C_8)$cycloalkyl substituted by one or more substituents selected from carboxylate, carboxylic acid, thiocarboxylate, thio acid, amido, ester, amino and heterocyclyl and additionally optionally substituted by one or more further substituents, such as alkyl, alkoxy, aralkyl or aryl.

In accordance with any of the foregoing embodiments, in certain embodiments, $R_2$ is $(C_1-C_4)$alkyl substituted by one or more substituents selected from carboxylate, carboxylic acid and amido. In certain embodiments, $R_2$ is —$(CH_2)$COOH, —$(CH_2)_2COOH$, —$(CH_2)CONH_2$ or —$(CH_2)_2CONH_2$. In such certain embodiments, $R_2$ is —$(CH_2)_2C(O)NH_2$, —$CH_2C(O)NH_2$, —$(CH_2)_2C(O)NH(alkyl)$ or —$CH_2C(O)NH(alkyl)$.

In some embodiments, $R_2$ represents $(C_1-C_6)$alkyl, $(C_2-C_6)$alkenyl or $(C_2-C_6)$alkynyl substituted by one or more substituents selected from amino, alkylamino, acylamino, hydroxy, cycloalkyl, aryl, (heterocyclyl)alkyl, heteroaryl, (heteroaryl)alkyl, guanidino, —SH and —S(alkyl). In some such embodiments, $R_2$ represents $(C_1-C_6)$alkyl, $(C_2-C_6)$alkenyl or $(C_2-C_6)$alkynyl substituted by one or more substituents selected from alkylamino, acylamino, cycloalkyl and (heterocyclyl)alkyl.

In certain embodiments, $R_3$ is hydrogen, —CO-[Aaa1]$_m$, [Aaa1]$_m$, [Aaa1]$_m$—CO-[Aaa1]m or —S(O)$_p$-[Aaa1]$_m$.

In certain embodiments, $R_3$ is —CO-Aaa1 and the side chain of Aaa1 comprises a $(C_1-C_4)$alkyl group optionally substituted by one or more substituents selected from amino, alkylamino, acylamino, carboxylic acid, carboxylate, carboxylate, thioacid, —$CONR_7R_8$, hydroxy, cycloalkyl, aryl, heterocyclyl, heteroaryl, guanidino, —SH, —S(alkyl); optionally wherein cycloalkyl, aryl, heterocyclyl and heteroaryl are further substituted by one or more substituents such as hydroxy, alkoxy, halo, amino, nitro, cyano or alkyl.

Alternatively, $R_3$ may represent —CO-[Aaa1]$_m$, wherein m is greater than 1. In other embodiments, $R_3$ may represent [Aaa1]$_m$, [Aaa1]$_m$—CO-[Aaa1]m or —S(O)$_p$-[Aaa1]$_m$, wherein m is an integer from 1 to 3.

In further embodiments, the side chain of Aaa1 comprises a ($C_1$-$C_4$)alkyl group substituted by one or more substituents selected from amino, acylamino, carboxylic acid, —CONR$_7$R$_8$, hydroxy, cycloalkyl, aryl, heteroaryl, guanidino, —SH and —S(alkyl); wherein $R_7$ and $R_8$ independently are hydrogen, alkyl, aryl or heterocyclyl.

In further alternative embodiments, $R_3$ may represent ($C_1$-$C_6$)alkyl, ($C_2$-$C_6$)alkenyl or ($C_2$-$C_6$)alkynyl, substituted by carboxylic acid, carboxylate, thiocarboxylate, thioacid, —CONR$_7$R$_8$, hydroxy, —SH and —S(alkyl). Particularly, $R_3$ is CONR$_7$R$_8$; wherein $R_7$ and $R_8$ independently are hydrogen, ($C_1$-$C_6$)alkyl, ($C_2$-$C_6$)alkenyl or ($C_2$-$C_6$)alkynyl; wherein ($C_1$-$C_6$)alkyl, ($C_2$-$C_6$)alkenyl and ($C_2$-$C_6$)alkynyl are substituted by one or more substituents selected from halogen, hydroxyl, amino, nitro, cyano, cycloalkyl, heterocyclyl, heteroaryl, guanidino, (cycloalkyl)alkyl, (heterocyclyl)alkyl and (heteroaryl)alkyl.

In further alternative embodiments, $R_3$ may represent —CONR$_7$R$_8$; wherein $R_7$ and $R_8$ independently are hydrogen, ($C_1$-$C_6$)alkyl, ($C_2$-$C_6$)alkenyl or ($C_2$-$C_6$)alkynyl; wherein ($C_1$-$C_6$)alkyl, ($C_2$-$C_6$)alkenyl and ($C_2$-$C_6$)alkynyl; optionally wherein two or three carbon atoms of the ($C_1$-$C_6$)alkyl, ($C_2$-$C_6$)alkenyl or ($C_2$-$C_6$)alkynyl form part of a 3-7-membered carbocyclic or heterocyclic ring (such as a cyclobutyl or oxirane ring);

In certain embodiments, $R_3$ is —COR$_c$ or —SO$_2$R$_c$ wherein $R_1$ is ($C_1$-$C_6$)alkyl, cycloalkyl, aryl, heterocyclcyl or heteroaryl; wherein the said ($C_1$-$C_6$)alkyl, cycloalkyl, aryl, heterocyclcyl or heteroaryl is optionally substituted by one or more substituents selected from carboxylic acid, hydroxyl, alkyl, alkoxy, amino, alkylamino, acylamino, carboxylic ester, cycloalkyl, heterocyclyl, heteroaryl, (cycloalkyl)alkyl, (heterocyclyl)alkyl or (heteroaryl)alkyl.

Alternatively, $R_3$ may represent —COR$_c$ or —SO$_2$R$_c$ wherein $R_c$ is ($C_1$-$C_6$)alkyl, cycloalkyl, aryl, heterocyclcyl or heteroaryl; wherein the said ($C_1$-$C_6$)alkyl, aryl, heterocyclcyl or heteroaryl is optionally substituted by one or more substituents selected from carboxylic acid, hydroxyl, alkyl, amino or acylamino.

In further alternative embodiments, $R_3$ may represent ($C_1$-$C_6$)alkyl, ($C_2$-$C_6$)alkenyl or ($C_2$-$C_6$)alkynyl, substituted by carboxylic acid, carboxylate, thiocarboxylate, thioacid, —CONR$_7$R$_8$, hydroxy, —SH and —S(alkyl).

In certain embodiments, $R_6$ is hydrogen, alkyl, [Aaa2]$_n$ or —CO-[Aaa2]$_n$. $R_6$ may be —CO-[Aaa2]$_n$. Alternatively, $R_6$ may be H.

In certain embodiments, $R_6$ is —CO-Aaa2 and the side chain of Aaa2 comprises a ($C_1$-$C_4$)alkyl group optionally substituted by one or more substituents selected from amino, alkylamino, acylamino, carboxylic acid, carboxylate, thiocarboxylate, thioacid, —CONR$_7$R$_8$, hydroxy, cycloalkyl, aryl, heterocyclyl, heteroaryl, guanidino, —SH, —S(alkyl); optionally wherein cycloalkyl, heterocyclyl and heteroaryl are further substituted by one or more substituents such as hydroxy, alkoxy, halo, amino, nitro, cyano or alkyl.

In further embodiments, the side chain of Aaa2 comprises a ($C_1$-$C_4$)alkyl group substituted by one or more substituents selected from amino, acylamino, carboxylic acid, —CONR$_7$R$_8$, hydroxy, cycloalkyl, aryl, heteroaryl, guanidino, —SH and —S(alkyl); wherein $R_7$ and $R_8$ independently are hydrogen or alkyl.

In certain embodiments, Aaa1 or Aaa2 represents an amino acid residue, wherein the amino acid residue comprises a side chain that includes a —OH, —O-acyl, —SH, —NH$_2$ or NH(alkyl) moiety.

In certain embodiments, $R_7$ is ($C_1$-$C_6$)alkyl, ($C_2$-$C_6$)alkenyl or ($C_2$-$C_6$)alkynyl substituted by one or more substituents selected from halogen, hydroxyl, amino, nitro, cyano, cycloalkyl, heterocyclyl, heteroaryl, guanidino, (cycloalkyl)alkyl, (heterocyclyl)alkyl and (heteroaryl)alkyl.

In certain embodiments, $R_8$ is ($C_1$-$C_6$)alkyl, ($C_2$-$C_6$)alkenyl or ($C_2$-$C_6$)alkynyl substituted by one or more substituents selected from halogen, hydroxyl, amino, nitro, cyano, cycloalkyl, heterocyclyl, heteroaryl, guanidino, (cycloalkyl)alkyl, (heterocyclyl)alkyl and (heteroaryl)alkyl.

In certain embodiments, $R_a$ is alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl.

In certain embodiments, $R_1$ is a side chain of an amino acid or hydrogen, ($C_1$-$C_6$)alkyl, ($C_2$-$C_6$)alkenyl, ($C_2$-$C_6$)alkynyl or cycloalkyl; wherein ($C_1$-$C_6$)alkyl, ($C_2$-$C_6$)alkenyl, ($C_2$-$C_6$)alkynyl and cycloalkyl are optionally substituted by one or more substituents selected from amino, alkylamino, acylamino, carboxylic acid, carboxylate, carboxylic acid ester, thiocarboxylate, thioacid, —CONR$_7$R$_8$, hydroxy, cycloalkyl, (cycloalkyl)alkyl, aryl, heterocyclyl, (heterocyclyl)alkyl, heteroaryl, (heteroaryl)alkyl, guanidino, —SH and —S(alkyl); optionally wherein cycloalkyl, aryl, heterocyclyl and heteroaryl are further substituted by one or more substituents such as hydroxy, alkoxy, halo, amino, nitro, cyano or alkyl, and optionally wherein two or three carbon atoms of the ($C_1$-$C_6$)alkyl, ($C_2$-$C_6$)alkenyl, or ($C_2$-$C_6$)alkynyl form part of a 3-7-membered carbocyclic or heterocyclic ring (such as a cyclobutyl or oxirane ring); and $R_a$ is hydrogen or alkyl, alkenyl, alkynyl, acyl, aralkyl, aryl, heteroaralkyl, heteroaryl, cycloalkyl, (cycloalkyl)alkyl, aminoalkyl, hydroxyalkyl, or alkoxyalkyl.

In certain embodiments, $R_b$ is alkenyl, alkynyl, acyl, aralkyl, aryl, heteroaralkyl, heteroaryl, cycloalkyl, (cycloalkyl)alkyl, aminoalkyl, hydroxyalkyl or alkoxyalkyl. Alternatively, in certain embodiments, $R_b$ and $R_2$, together with the atoms to which they are attached, form a pyrrolidine or piperidine ring optionally substituted with one or more groups independently selected from hydroxyl, halo, amino, cyano and alkyl.

In certain embodiments, the present invention provides compounds of formula (IA):

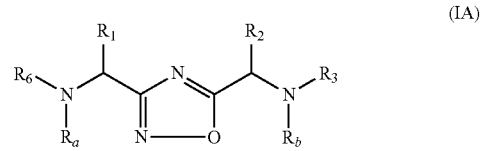

(IA)

or a pharmaceutically acceptable salt or a stereoisomer thereof; wherein, $R_1$, $R_2$, $R_3$, $R_6$, $R_a$ and $R_b$ are same as defined in formula (I).

In certain embodiments of the compound of formula (I) or formula (IA), $R_b$ is H.

In further embodiments of the compound of formula (I) or formula (IA), $R_3$ is —CO-[Aaa1]$_m$.

For example, the compounds of the present invention may have the structure of formula (IB):

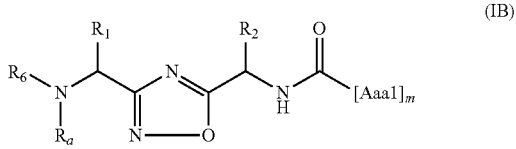

(IB)

or a pharmaceutically acceptable salt or a stereoisomer thereof; wherein, $R_1$, $R_2$, $R_6$, $R_a$, [Aaa1] and m are same as defined in formula (I).

In certain embodiments, the present invention provides compounds of formula (IC):

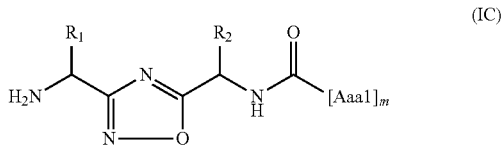

(IC)

or a pharmaceutically acceptable salt or a stereoisomer thereof; wherein, $R_1$, $R_2$, [Aaa1] and m are same as defined in formula (I).

In certain embodiments, the present invention provides compounds of formula (ID):

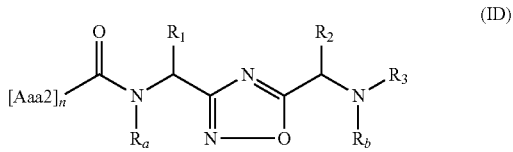

(ID)

or a pharmaceutically acceptable salt or a stereoisomer thereof; wherein, $R_1$, $R_2$, $R_3$, $R_a$, $R_b$, [Aaa2] and n are same as defined in formula (I).

In certain embodiments, the present invention provides compounds of formula (IE):

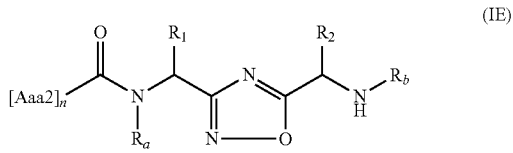

(IE)

or a pharmaceutically acceptable salt or a stereoisomer thereof; wherein, $R_1$, $R_2$, $R_a$, $R_b$, [Aaa2] and n are same as defined in formula (I).

An amino acid residue is understood in the art to mean a carboxylic acid, substituted at the alpha, beta or gamma carbon by an amino (—$NH_2$) group. In the group —CO-Aaa, the amino acid residue Aaa is connected to the carbonyl group CO via a covalent bond between the carbonyl carbon and the amino group of the amino acid residue. In preferred embodiments, the amino acid is an alpha-amino acid and the amino acid residue Aaa is connected to the carbonyl group CO via a covalent bond between the carbonyl carbon and the alpha-amino group of the amino acid residue.

In accordance with any of the foregoing embodiments, in certain embodiments, X is O.

In accordance with any of the foregoing embodiments, in certain embodiments of formula (I), (IA) or (ID), $R_3$ is hydrogen.

In accordance with one of the foregoing embodiments, in certain embodiments of formula (I), (IA) or (ID), $R_3$ is —CO-Aaa.

In accordance with any one of the foregoing embodiments, in certain embodiments of formula (I), (IA), (IB), (IC), (ID) or (IE), $R_1$ is alkyl substituted by amino or heteroaryl. Preferably, $R_1$ is —$(CH_2)_4NH_2$.

In accordance with any of the foregoing embodiments, in certain embodiments, $R_1$ is side chain of an amino acid.

In accordance with any of the foregoing embodiments, in certain embodiments, $R_2$ is side chain of an amino acid.

In accordance with any of the foregoing embodiments, in certain embodiments, $R_1$ is a side chain of Lys, Tyr, Gln, Ser, Ala, Glu, Leu, Asp or His.

In accordance with any of the foregoing embodiments, in certain embodiments, $R_1$ is a side chain of Lys, Tyr or Gln.

In accordance with any of the foregoing embodiments, in certain embodiments, $R_1$ is a side chain of Tyr.

In accordance with any of the foregoing embodiments, in certain embodiments, $R_1$ is a side chain of Lys.

In accordance with any of the foregoing embodiments, in certain embodiments, $R_1$ is a side chain of Gln.

In alternative embodiments, $R_1$ does not represent a side chain of Ser or Thr; i.e., $R_1$ is not —$CH_2OH$ or —$CH(CH_3)$OH. In further alternative embodiments, $R_1$ is not a side chain of Ser or Thr that is alkylated or acylated. For example, in certain embodiments, $R_1$ is not —$CH_2OCH_3$, —$CH_2OAc$, —$CH(CH_3)OCH_3$ or —$CH(CH_3)OAc$. In further embodiments, $R_1$ does not represent a side chain of Ser or Thr that is optionally alkylated or acylated, i.e., $R_1$ is not —$CH_2OH$, —$CH(CH_3)OH$, —$CH_2OCH_3$, —$CH_2OAc$, —$CH(CH_3)OCH_3$ or —$CH(CH_3)OAc$.

In accordance with any one of the foregoing embodiments, in certain embodiments of formula (I), (IA), (IB), (IC), (ID) or (IE), $R_2$ is alkyl substituted by amido. In certain embodiments, $R_2$ is —$(CH_2)_2C(O)NH_2$ or —$CH_2C(O)NH_2$. Preferably, $R_2$ is —$CH_2C(O)NH_2$.

In accordance with any of the foregoing embodiments, in certain embodiments, $R_2$ is a side chain of Gly, Gln, Glu, Ser, Asn, Asp, Ala or Ile.

In accordance with any of the foregoing embodiments, in certain embodiments, $R_2$ is a side chain of Gln, Glu, Asn, Asp or Ile.

In accordance with any of the foregoing embodiments, in certain embodiments, $R_2$ is a side chain of Ile.

In accordance with any of the foregoing embodiments, in certain embodiments, $R_2$ is a side chain of Ala.

In accordance with any of the foregoing embodiments, in certain embodiments, $R_2$ is a side chain of Asn.

In alternative embodiments, $R_2$ does not represent a side chain of Asn, Asp, Gln, or Glu; i.e., $R_2$ is not —$CH_2C(O)NH_2$, —$CH_2C(O)OH$, —$CH_2CH_2C(O)NH_2$ or —$CH_2CH_2C(O)OH$.

In accordance with any of the foregoing embodiments, in certain embodiments, $R_b$ and $R_2$, together with the atoms to which they are attached, may form pyrrolidine optionally substituted with hydroxyl.

In accordance with any of the foregoing embodiments, in certain embodiments, m is 1.

In accordance with any one of the foregoing embodiments, in certain embodiments [Aaa1] comprises a side chain that includes an —OH moiety.

In accordance with any of the foregoing embodiments, in certain embodiments, [Aaa1] is Ala, Thr, Ile, Glu, Lys, Asp, Tyr, Gln, Ser or Phe.

In accordance with any of the foregoing embodiments, in certain embodiments, [Aaa1] is Ser, Thr, Tyr, Glu, Ala or Ile.

In accordance with any of the foregoing embodiments, in certain embodiments, [Aaa1] is Tyr.

In accordance with any of the foregoing embodiments, in certain embodiments, [Aaa1] is Glu.

In accordance with any of the foregoing embodiments, in certain embodiments, [Aaa1] is Ala.

In accordance with any of the foregoing embodiments, in certain embodiments, [Aaa1] is Thr.

In accordance with any of the foregoing embodiments, in certain embodiments, [Aaa1] is Ile.

In alternative embodiments, $R_3$ is —CO-[Aaa1], and Aaa1 does not represent an amino acid residue of Thr or Ser.

In further alternative embodiments, $R_3$ is not H or —CO-[Aaa1].

In accordance with any of the foregoing embodiments, in certain embodiments, n is 1.

In accordance with any of the foregoing embodiments, in certain embodiments, [Aaa2] is Ala, Thr, Ile, Glu, Lys, Asp, Tyr, Gln, Ser or Phe.

In accordance with any of the foregoing embodiments, in certain embodiments, [Aaa2] is Ser, Thr, Tyr, Glu, Ala or Ile.

In accordance with any of the foregoing embodiments, in certain embodiments, p is 2.

In accordance with any of the foregoing embodiments, in certain embodiments, one, more or all amino acid residues are D amino acid residues.

In accordance with any of the foregoing embodiments, in certain embodiments, one, more than one or all amino acid residues are L amino acid residues.

In certain embodiments, the present invention provides a compound or a pharmaceutically acceptable salt or a stereoisomer thereof, selected from:

| Compound No. | Structure |
| --- | --- |
| 1 | 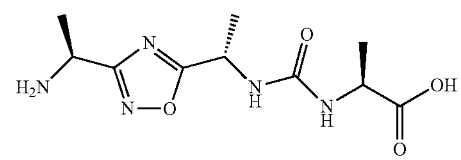 [SMILES: C[C@H](NC(=O)N[C@@H](C)c1nc([C@H](C)N)no1)C(=O)O] |
| 2 | 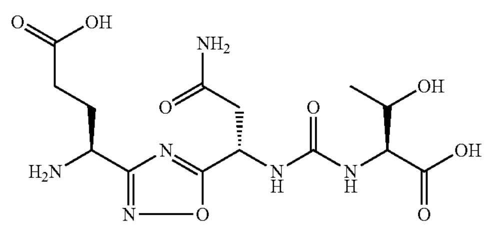 [SMILES: CC(O)[C@H](NC(=O)N[C@@H](CC(N)=O)c1nc([C@@H](N)CCC(=O)O)no1)C(=O)O] |
| 3 | 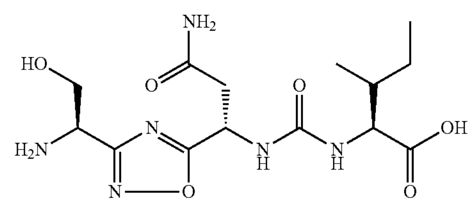 [SMILES: CCC(C)[C@H](NC(=O)N[C@@H](CC(N)=O)c1nc([C@@H](N)CO)no1)C(=O)O] |
| 4 | 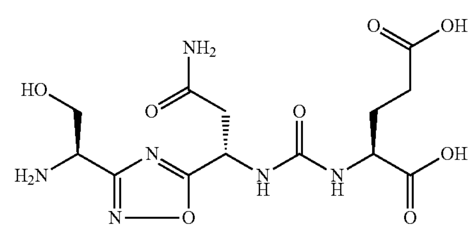 [SMILES: NC(=O)C[C@H](NC(=O)N[C@@H](CCC(=O)O)C(=O)O)c1nc([C@@H](N)CO)no1] |
| 5 | 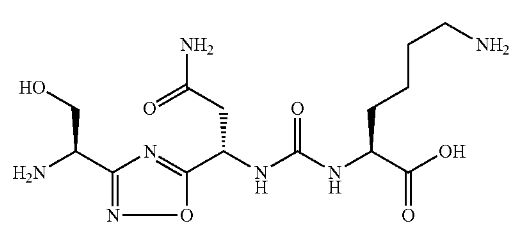 [SMILES: NCCCC[C@H](NC(=O)N[C@@H](CC(N)=O)c1nc([C@@H](N)CO)no1)C(=O)O] |

-continued

| Compound No. | Structure |
| --- | --- |
| 6 | 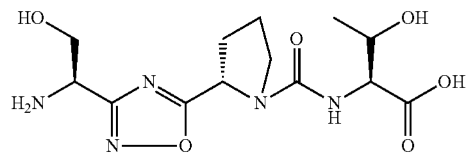 [SMILES: CC(O)[C@H](NC(=O)N1CCC[C@H]1c1nc([C@@H](N)CO)no1)C(=O)O] |
| 7 | 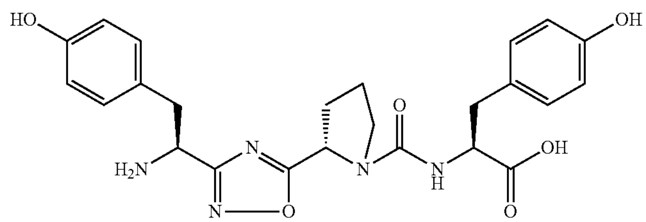 [SMILES: N[C@@H](Cc1ccc(O)cc1)c1noc([C@@H]2CCCN2C(=O)N[C@@H](Cc2ccc(O)cc2)C(=O)O)n1] |
| 8 | 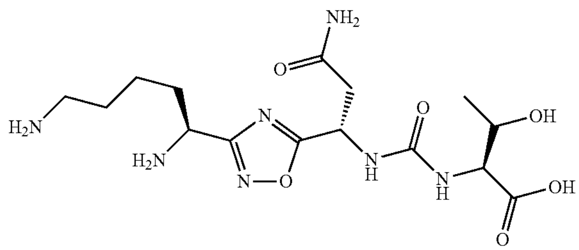 [SMILES: CC(O)[C@H](NC(=O)N[C@@H](CC(N)=O)c1nc([C@@H](N)CCCCN)no1)C(=O)O] |
| 9 | 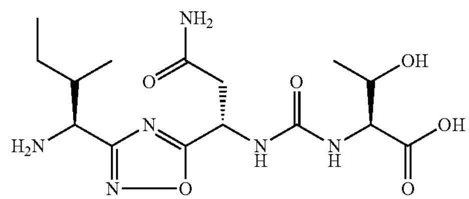 |
| 10 | 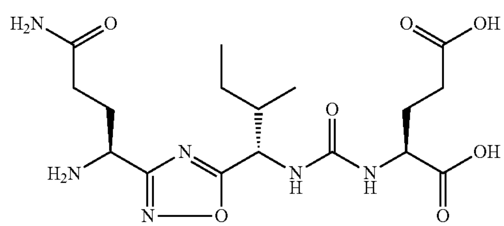 [SMILES: CCC(C)[C@H](NC(=O)N[C@@H](CCC(=O)O)C(=O)O)c1nc([C@@H](N)CCC(N)=O)no1] |
| 11 | 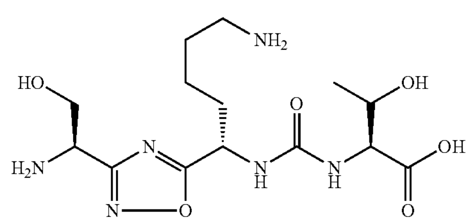 [SMILES: CC(O)[C@H](NC(=O)N[C@@H](CCCCN)c1nc([C@@H](N)CO)no1)C(=O)O] |
| 12 | 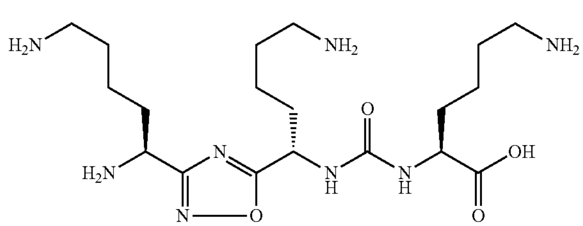 [SMILES: NCCCC[C@H](NC(=O)N[C@@H](CCCCN)c1nc([C@@H](N)CCCCN)no1)C(=O)O] |

-continued
| Compound No. | Structure |
|---|---|
| 13 | 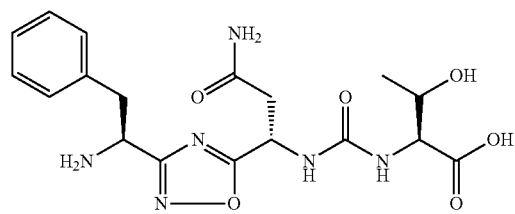 [SMILES: CC(O)[C@H](NC(=O)N[C@@H](CC(N)=O)c1nc([C@@H](N)Cc2ccccc2)no1)C(=O)O] |
| 14 | 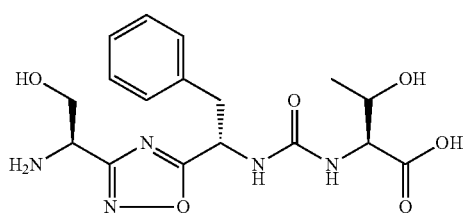 [SMILES: CC(O)[C@H](NC(=O)N[C@@H](Cc1ccccc1)c1nc([C@@H](N)CO)no1)C(=O)O] |
| 15 | 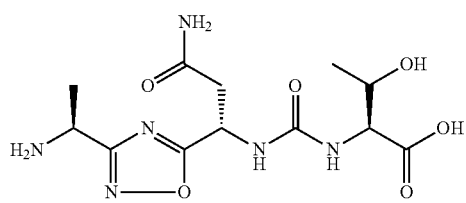 |
| 16 | 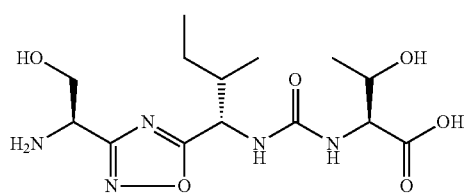 [SMILES: CCC(C)[C@H](NC(=O)N[C@H](C(=O)O)C(C)O)c1nc([C@@H](N)CO)no1] |
| 17 | 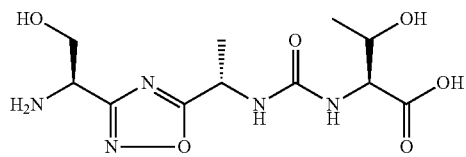 |
| 18 | 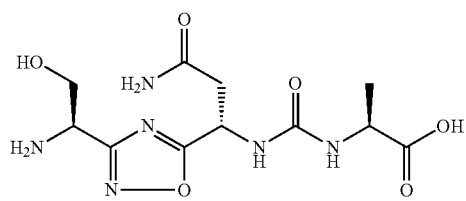 |
| 19 | 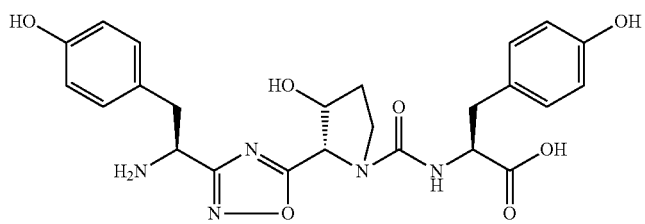 |

-continued
| Compound No. | Structure |
|---|---|
| 20 | 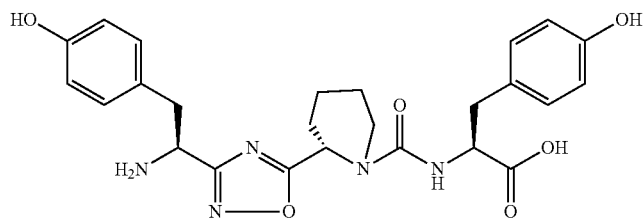 [SMILES: N[C@@H](Cc1ccc(O)cc1)c1noc([C@@H]2CCCCN2C(=O)N[C@@H](Cc2ccc(O)cc2)C(=O)O)n1] |
| 21 | 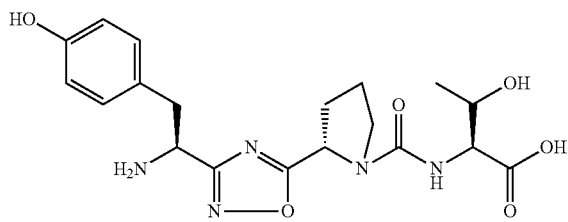 [SMILES: CC(O)[C@H](NC(=O)N1CCC[C@H]1c1nc([C@@H](N)Cc2ccc(O)cc2)no1)C(=O)O] |
| 22 | 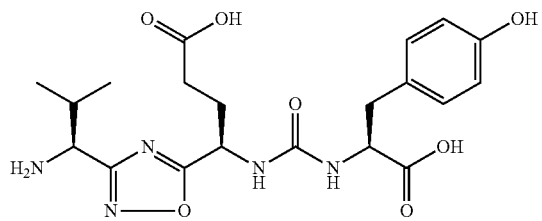 [SMILES: CC(C)[C@H](N)c1noc([C@@H](CCC(=O)O)NC(=O)N[C@@H](Cc2ccc(O)cc2)C(=O)O)n1] |
| 23 | 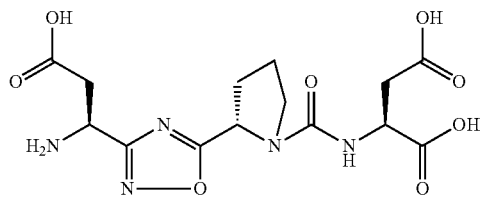 [SMILES: N[C@@H](CC(=O)O)c1noc([C@@H]2CCCN2C(=O)N[C@@H](CC(=O)O)C(=O)O)n1] |
| 24 | 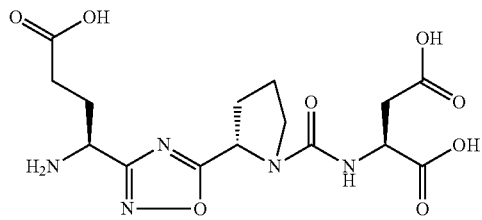 |
| 25 | 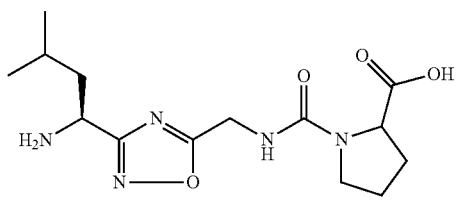 [SMILES: CC(C)C[C@H](N)c1noc(CNC(=O)N2CCCC2C(=O)O)n1] |
| 26 | 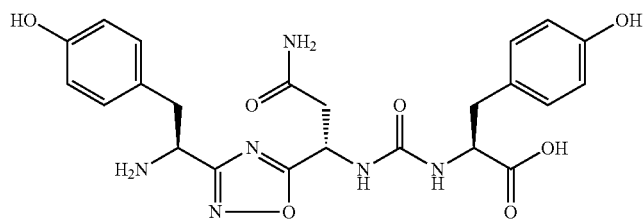 [SMILES: NC(=O)C[C@H](NC(=O)N[C@@H](Cc1ccc(O)cc1)C(=O)O)c1nc([C@@H](N)Cc2ccc(O)cc2)no1] |

-continued
| Compound No. | Structure |
|---|---|
| 27 | 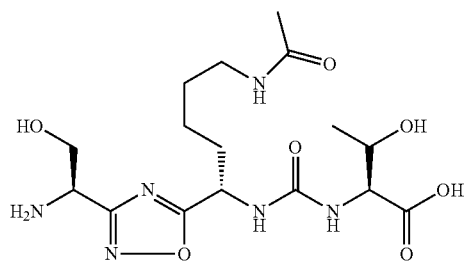 |
| 28 | 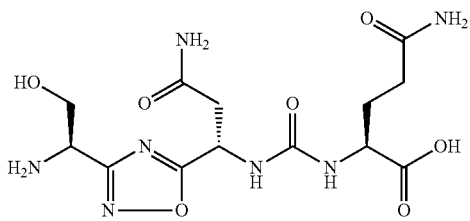 [SMILES: NC(=O)CC[C@H](NC(=O)N[C@@H](CC(N)=O)c1nc([C@@H](N)CO)no1)C(=O)O] |
| 29 | 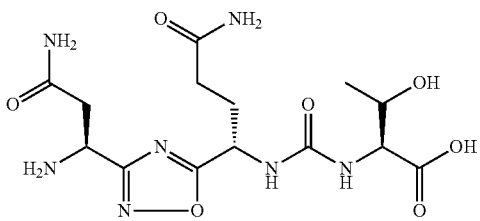 [SMILES: CC(O)[C@H](NC(=O)N[C@@H](CCC(N)=O)c1nc([C@@H](N)CC(N)=O)no1)C(=O)O] |
| 30 | 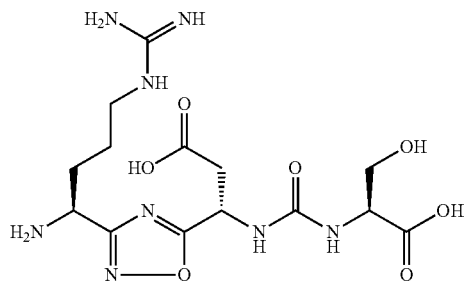 [SMILES: N=C(N)NCCC[C@H](N)c1noc([C@H](CC(=O)O)NC(=O)N[C@@H](CO)C(=O)O)n1] |
| 31 | 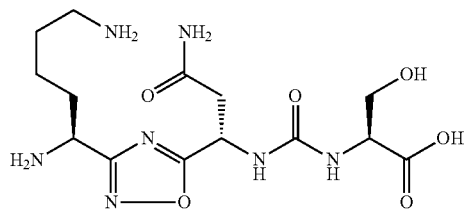 [SMILES: NCCCC[C@H](N)c1noc([C@H](CC(N)=O)NC(=O)N[C@@H](CO)C(=O)O)n1] |
| 32 | 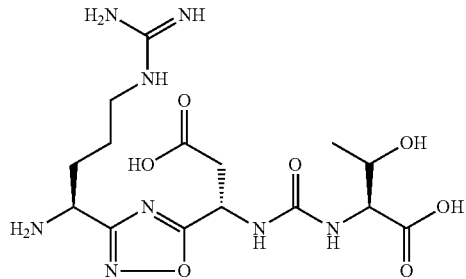 |

-continued

| Compound No. | Structure |
|---|---|
| 33 | 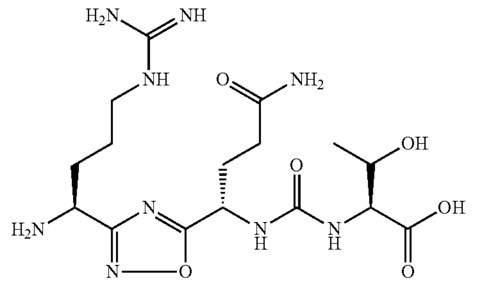 [SMILES: CC(O)[C@H](NC(=O)N[C@@H](CCC(N)=O)c1nc([C@@H](N)CCCNC(=N)N)no1)C(=O)O] |
| 34 | 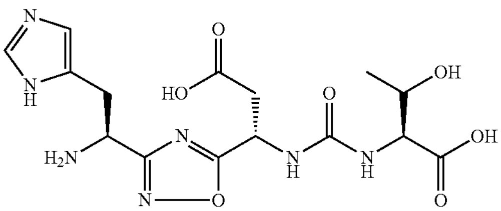 [SMILES: CC(O)[C@H](NC(=O)N[C@@H](CC(=O)O)c1nc([C@@H](N)Cc2cnc[nH]2)no1)C(=O)O] |
| 35 | 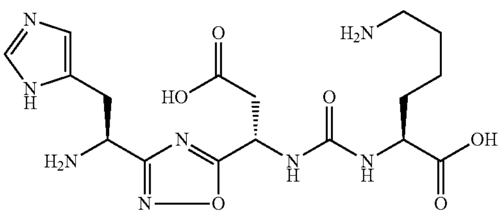 [SMILES: NCCCC[C@H](NC(=O)N[C@@H](CC(=O)O)c1nc([C@@H](N)Cc2cnc[nH]2)no1)C(=O)O] |
| 36 | 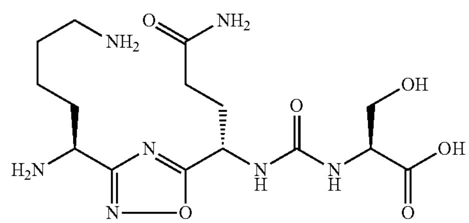 |
| 37 | 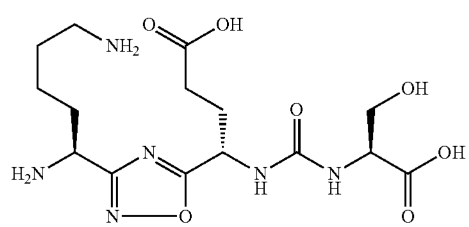 |
| 38 | 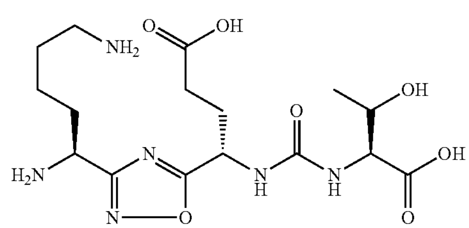 [SMILES: CC(O)[C@H](NC(=O)N[C@@H](CCC(=O)O)c1nc([C@@H](N)CCCCN)no1)C(=O)O] |
| 39 | 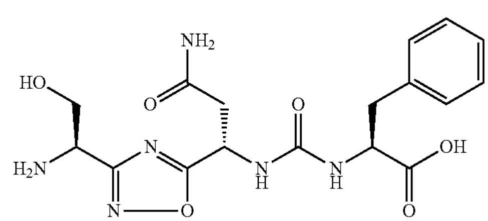 [SMILES: NC(=O)C[C@H](NC(=O)N[C@@H](Cc1ccccc1)C(=O)O)c1nc([C@@H](N)CO)no1] |

-continued
| Compound No. | Structure |
|---|---|
| 40 | 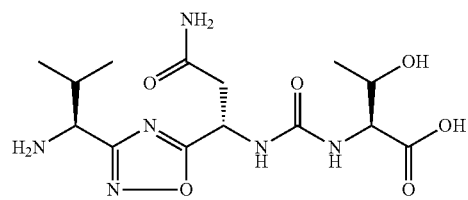 [SMILES: CC(O)[C@H](NC(=O)N[C@@H](CC(N)=O)c1nc([C@@H](N)C(C)C)no1)C(=O)O] |
| 41 | 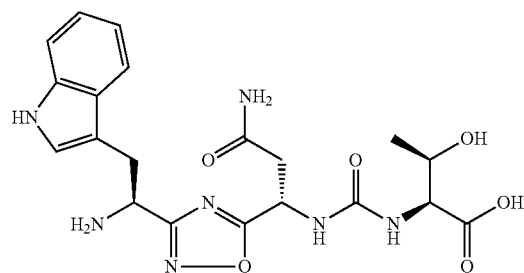 [SMILES: C[C@@H](O)[C@H](NC(=O)N[C@@H](CC(N)=O)c1nc([C@@H](N)Cc2c[nH]c3ccccc23)no1)C(=O)O] |
| 42 | 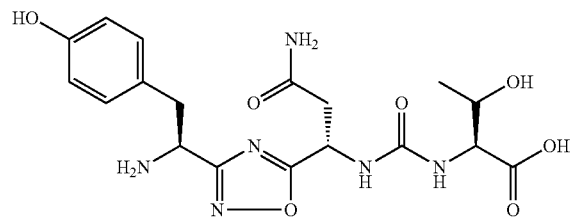 [SMILES: CC(O)[C@H](NC(=O)N[C@@H](CC(N)=O)c1nc([C@@H](N)Cc2ccc(O)cc2)no1)C(=O)O] |
| 43 | 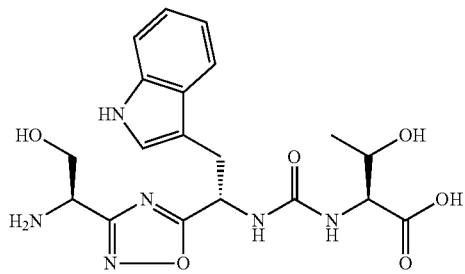 |
| 44 | 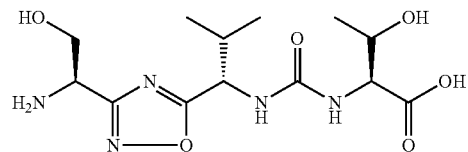 |
| 45 | 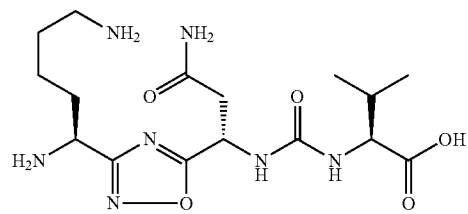 |
| 46 | 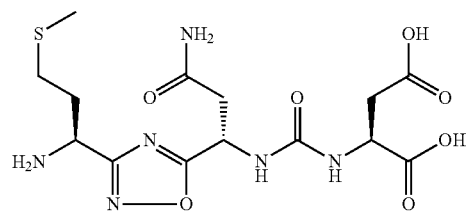 |

-continued
| Compound No. | Structure |
|---|---|
| 47 | 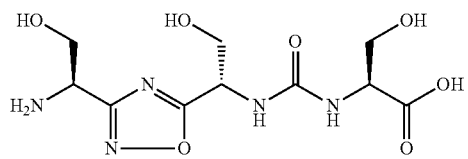 |
| 48 | 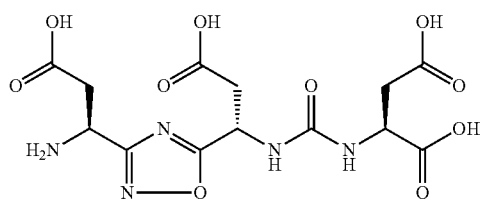 |
| 49 | 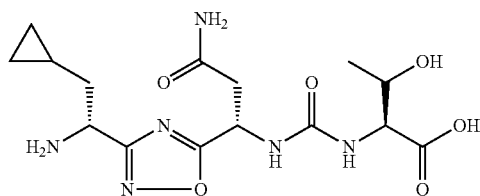 [SMILES: CC(O)[C@H](NC(=O)N[C@@H](CC(N)=O)c1nc([C@H](N)CC2CC2)no1)C(=O)O] |
| 50 | 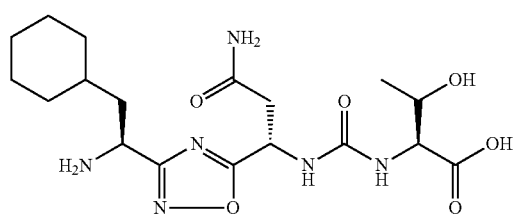 [SMILES: CC(O)[C@H](NC(=O)N[C@@H](CC(N)=O)c1nc([C@@H](N)CC2CCCCC2)no1)C(=O)O] |
| 51 | 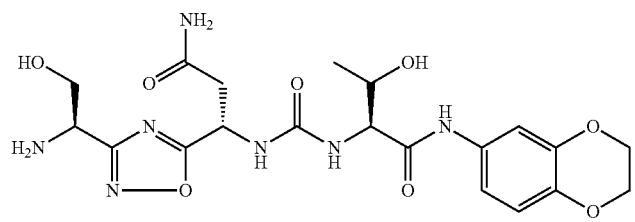 [SMILES: CC(O)[C@H](NC(=O)N[C@@H](CC(N)=O)c1nc([C@@H](N)CO)no1)C(=O)Nc1ccc2c(c1)OCCO2] |
| 52 | 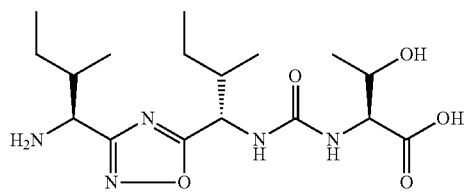 |
| 53 | 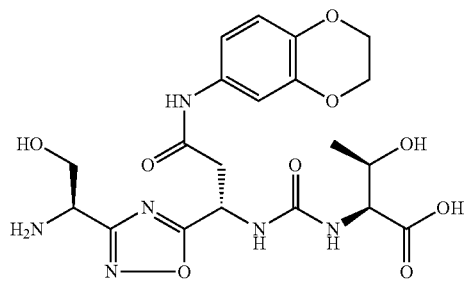 [SMILES: C[C@@H](O)[C@H](NC(=O)N[C@@H](CC(=O)Nc1ccc2c(c1)OCCO2)c1nc([C@@H](N)CO)no1)C(=O)O] |

| Compound No. | Structure |
|---|---|
| 54 | 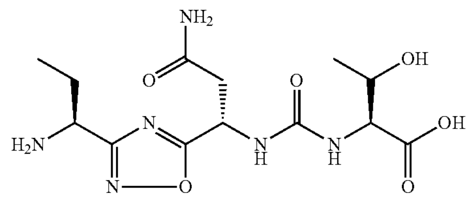 [SMILES: CC[C@H](N)c1noc([C@H](CC(N)=O)NC(=O)N[C@H](C(=O)O)C(C)O)n1] |
| 55 | 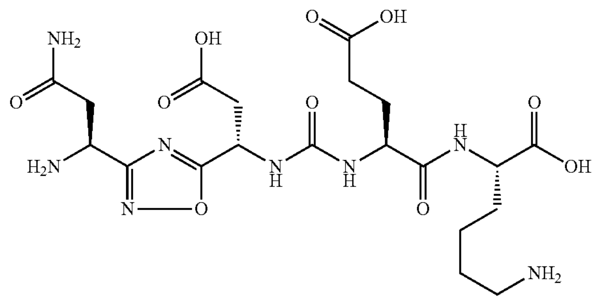 [SMILES: NCCCC[C@H](NC(=O)[C@H](CCC(=O)O)NC(=O)N[C@@H](CC(=O)O)c1nc([C@@H](N)CC(N)=O)no1)C(=O)O] |
| 56 | 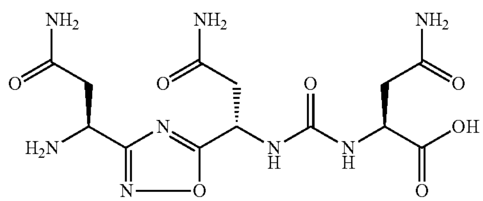 [SMILES: NC(=O)C[C@H](NC(=O)N[C@@H](CC(N)=O)c1nc([C@@H](N)CC(N)=O)no1)C(=O)O] |
| 57 | 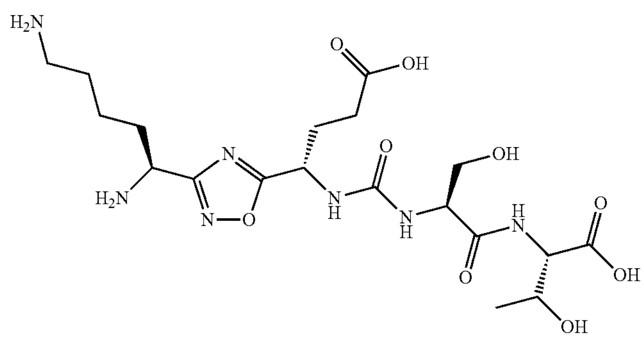 [SMILES: CC(O)[C@H](NC(=O)[C@H](CO)NC(=O)N[C@@H](CCC(=O)O)c1nc([C@@H](N)CCCCN)no1)C(=O)O] |
| 58 | 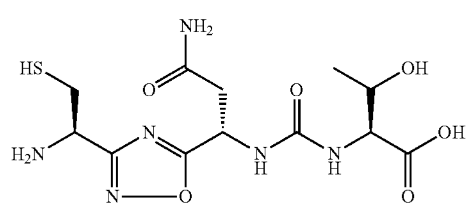 |
| 59 | 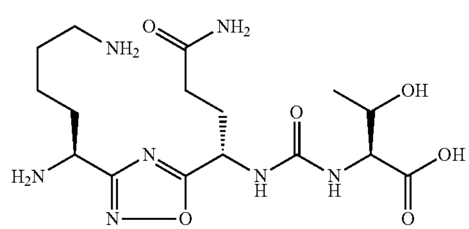 |

-continued
| Compound No. | Structure |
|---|---|
| 60 | 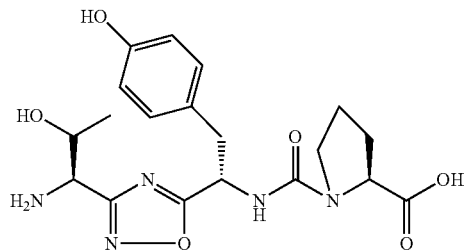 |
| 61 | 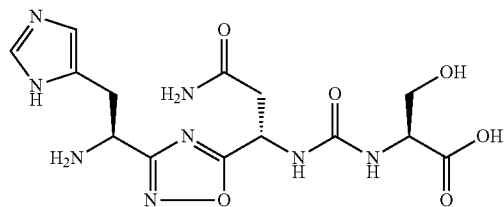 [SMILES: NC(=O)C[C@H](NC(=O)N[C@@H](CO)C(=O)O)c1nc([C@@H](N)Cc2cnc[nH]2)no1] |
| 62 | 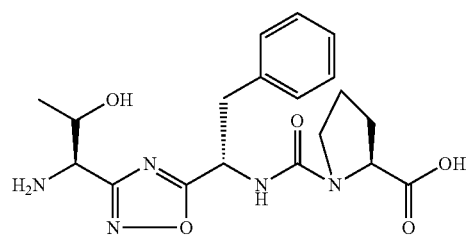 [SMILES: CC(O)[C@H](N)c1noc([C@H](Cc2ccccc2)NC(=O)N2CCC[C@H]2C(=O)O)n1] |
| 63 | 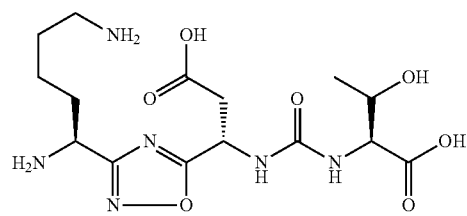 |
| 64 | 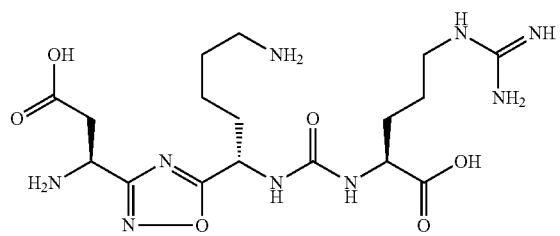 [SMILES: N=C(N)NCCC[C@H](NC(=O)N[C@@H](CCCCN)c1nc([C@@H](N)CC(=O)O)no1)C(=O)O] |
| 65 | 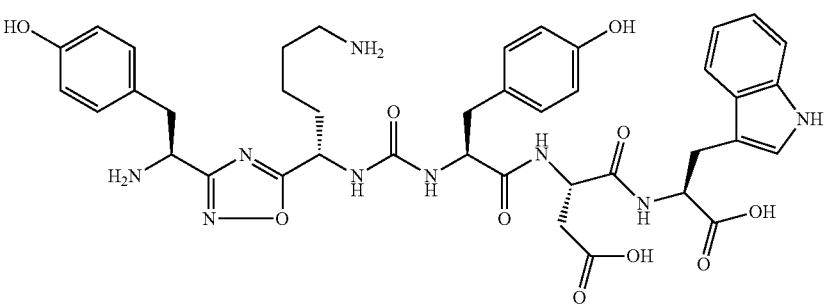 [SMILES: NCCCC[C@H](NC(=O)N[C@@H](Cc1ccc(O)cc1)C(=O)N[C@@H](CC(=O)O)C(=O)N[C@@H](Cc1c[nH]c2ccccc12)C(=O)O)c1nc([C@@H](N)Cc2ccc(O)cc2)no1] |

-continued
| Compound No. | Structure |
|---|---|
| 66 | 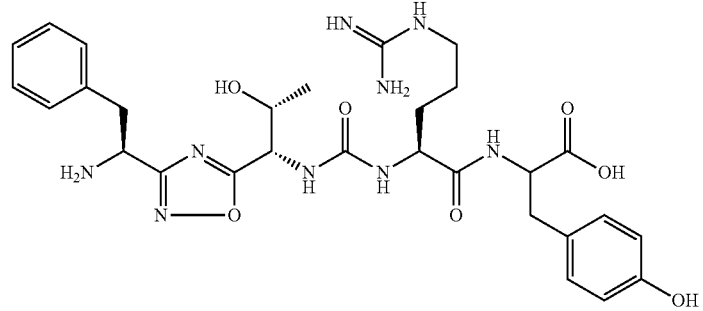 [SMILES: C[C@@H](O)[C@H](NC(=O)N[C@@H](CCCNC(=N)N)C(=O)NC(Cc1ccc(O)cc1)C(=O)O)c1nc([C@@H](N)Cc2ccccc2)no1] |
| 67 | 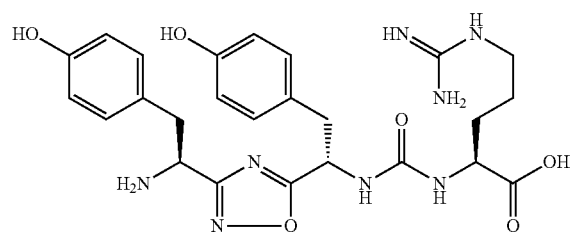 [SMILES: N=C(N)NCCC[C@H](NC(=O)N[C@@H](Cc1ccc(O)cc1)c1nc([C@@H](N)Cc2ccc(O)cc2)no1)C(=O)O] |
| 68 | 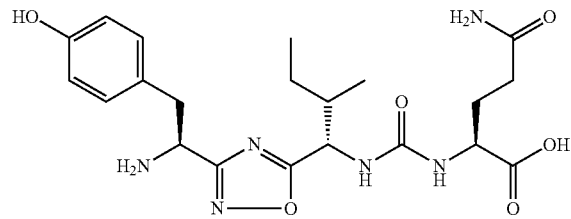 [SMILES: CCC(C)[C@H](NC(=O)N[C@@H](CCC(N)=O)C(=O)O)c1nc([C@@H](N)Cc2ccc(O)cc2)no1] |
| 69 | 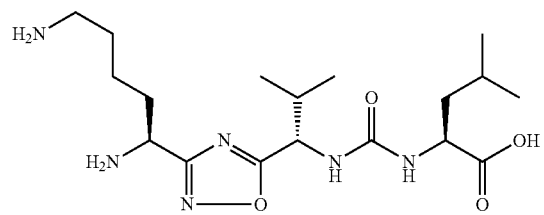 [SMILES: CC(C)C[C@H](NC(=O)N[C@H](c1nc([C@@H](N)CCCCN)no1)C(C)C)C(=O)O] |
| 70 | 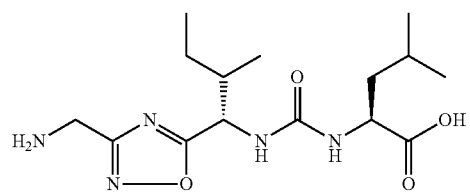 [SMILES: CCC(C)[C@H](NC(=O)N[C@@H](CC(C)C)C(=O)O)c1nc(CN)no1] |
| 71 | 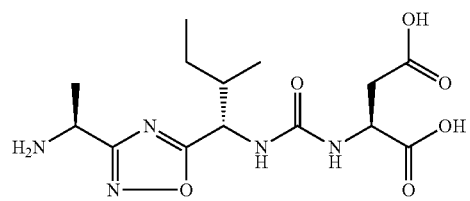 [SMILES: CCC(C)[C@H](NC(=O)N[C@@H](CC(=O)O)C(=O)O)c1nc([C@H](C)N)no1] |

-continued
| Compound No. | Structure |
|---|---|
| 72 | 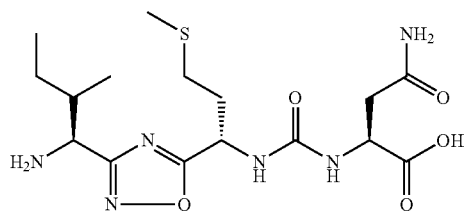 [SMILES: CCC(C)[C@H](N)c1noc([C@H](CCSC)NC(=O)N[C@@H](CC(N)=O)C(=O)O)n1] |
| 73 | 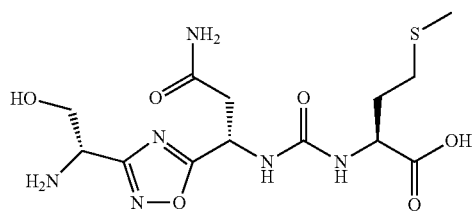 [SMILES: CSCC[C@H](NC(=O)N[C@@H](CC(N)=O)c1nc([C@H](N)CO)no1)C(=O)O] |
| 74 | 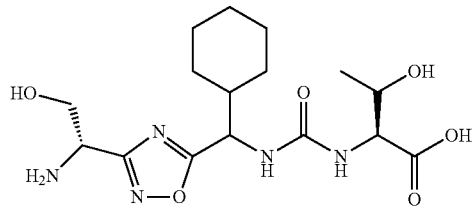 [SMILES: CC(O)[C@H](NC(=O)NC(c1nc([C@H](N)CO)no1)C1CCCCC1)C(=O)O] |
| 75 | 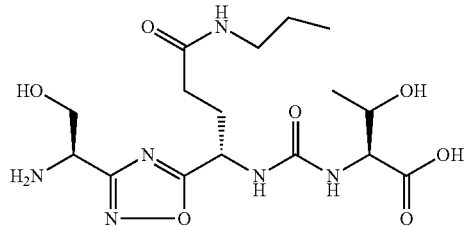 [SMILES: CCCNC(=O)CC[C@H](NC(=O)N[C@H](C(=O)O)C(C)O)c1nc([C@@H](N)CO)no1] |
| 76 | 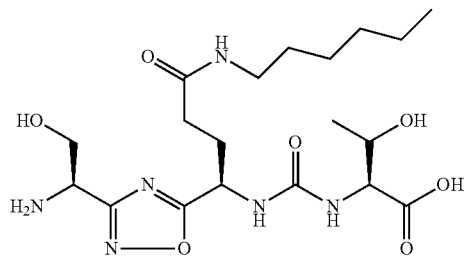 [SMILES: CCCCCCNC(=O)CC[C@@H](NC(=O)N[C@H](C(=O)O)C(C)O)c1nc([C@@H](N)CO)no1] |
| 77 | 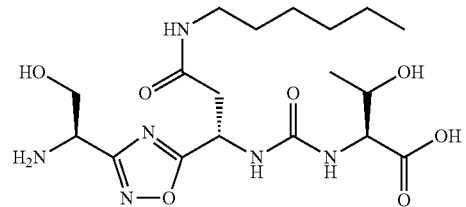 [SMILES: CCCCCCNC(=O)C[C@H](NC(=O)N[C@H](C(=O)O)C(C)O)c1nc([C@@H](N)CO)no1] |

-continued
| Compound No. | Structure |
|---|---|
| 78 | 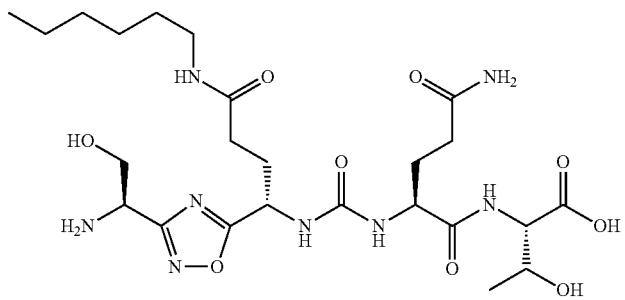 [SMILES: CCCCCCNC(=O)CC[C@H](NC(=O)N[C@@H](CCC(N)=O)C(=O)N[C@H](C(=O)O)C(C)O)c1nc([C@@H](N)CO)no1] |
| 79 | 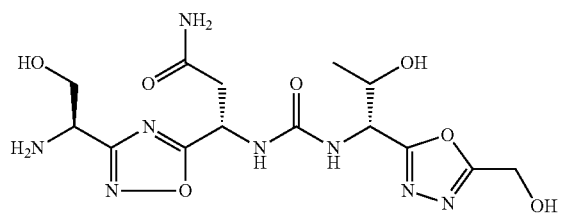 [SMILES: CC(O)[C@@H](NC(=O)N[C@@H](CC(N)=O)c1nc([C@@H](N)CO)no1)c1nnc(CO)o1] |
| 80 | 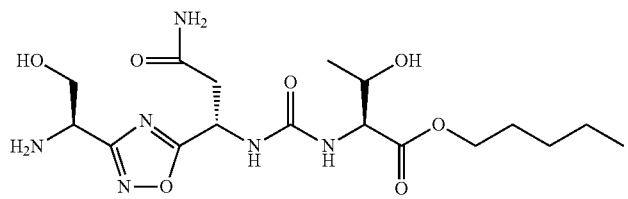 [SMILES: CCCCCOC(=O)[C@@H](NC(=O)N[C@@H](CC(N)=O)c1nc([C@@H](N)CO)no1)C(C)O] |
| 81 | 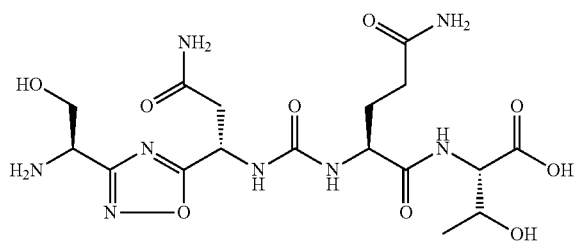 [SMILES: CC(O)[C@H](NC(=O)[C@H](CCC(N)=O)NC(=O)N[C@@H](CC(N)=O)c1nc([C@@H](N)CO)no1)C(=O)O] |
| 82 | 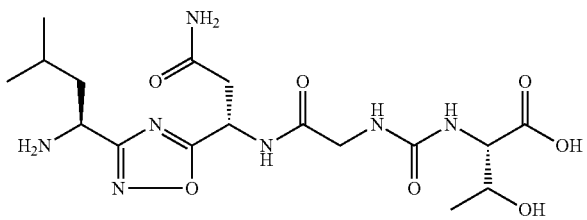 [SMILES: CC(C)C[C@H](N)c1noc([C@H](CC(N)=O)NC(=O)CNC(=O)N[C@H](C(=O)O)C(C)O)n1] |
| 83 | 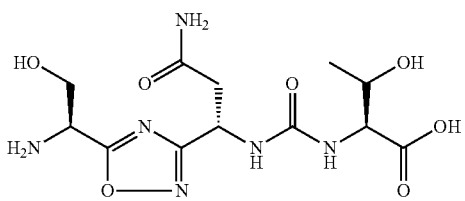 [SMILES: CC(O)[C@H](NC(=O)N[C@@H](CC(N)=O)c1noc([C@@H](N)CO)n1)C(=O)O] |
| 84 | 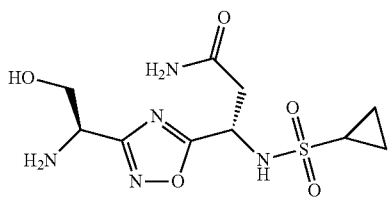 [SMILES: NC(=O)C[C@H](NS(=O)(=O)C1CC1)c1nc([C@@H](N)CO)no1] |

| Compound No. | Structure |
|---|---|
| 85 | 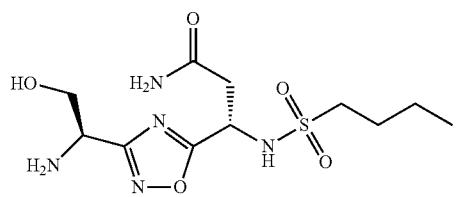 [SMILES: CCCCS(=O)(=O)N[C@@H](CC(N)=O)c1nc([C@@H](N)CO)no1] |
| 86 | 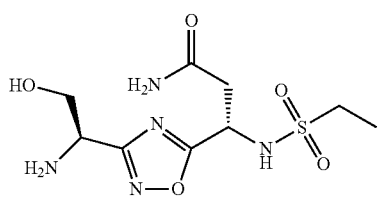 [SMILES: CCS(=O)(=O)N[C@@H](CC(N)=O)c1nc([C@@H](N)CO)no1] |
| 87 | 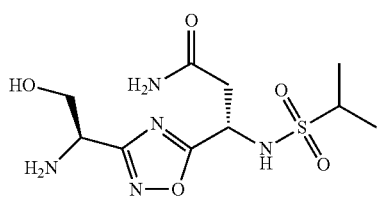 [SMILES: CC(C)S(=O)(=O)N[C@@H](CC(N)=O)c1nc([C@@H](N)CO)no1] |
| 88 | 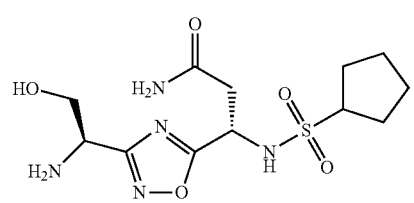 [SMILES: NC(=O)C[C@H](NS(=O)(=O)C1CCCC1)c1nc([C@@H](N)CO)no1] |
| 89 | 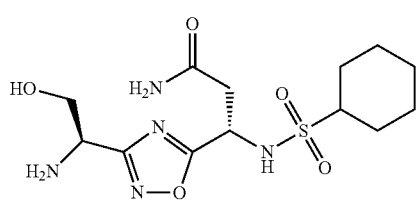 [SMILES: NC(=O)C[C@H](NS(=O)(=O)C1CCCCC1)c1nc([C@@H](N)CO)no1] |
| 90 | 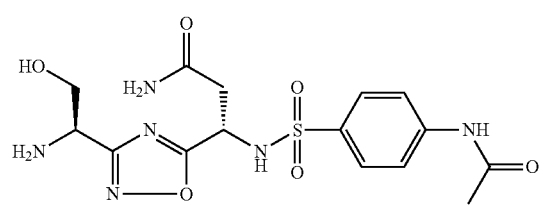 [SMILES: CC(=O)Nc1ccc(S(=O)(=O)N[C@@H](CC(N)=O)c2nc([C@@H](N)CO)no2)cc1] |
| 91 | 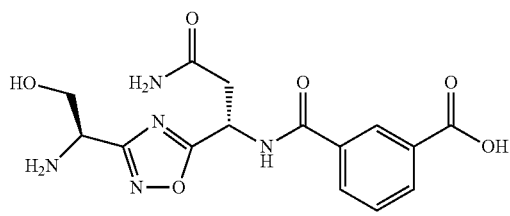 [SMILES: NC(=O)C[C@H](NC(=O)c1cccc(C(=O)O)c1)c1nc([C@@H](N)CO)no1] |

-continued

| Compound No. | Structure |
|---|---|
| 92 | 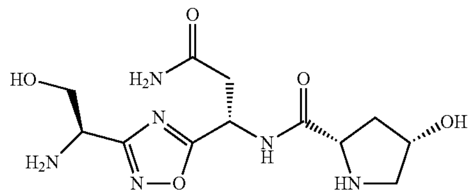 [SMILES: NC(=O)C[C@H](NC(=O)[C@@H]1C[C@H](O)CN1)c1nc([C@@H](N)CO)no1] |
| 93 | 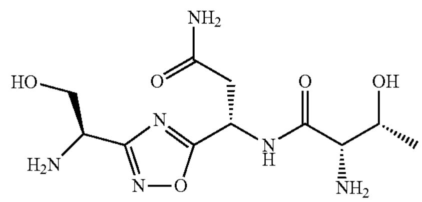 [SMILES: C[C@@H](O)[C@H](N)C(=O)N[C@@H](CC(N)=O)c1nc([C@@H](N)CO)no1] |
| 94 | 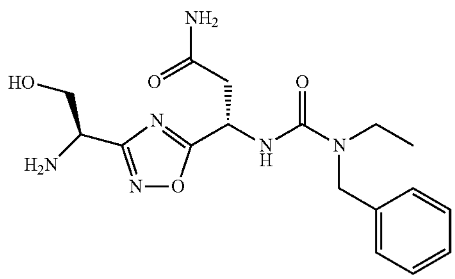 [SMILES: CCN(Cc1ccccc1)C(=O)N[C@@H](CC(N)=O)c1nc([C@@H](N)CO)no1] |
| 95 | 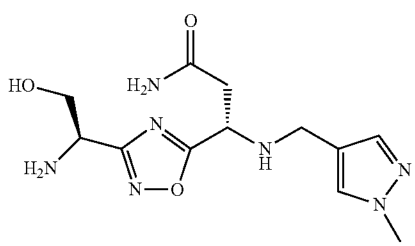 [SMILES: Cn1cc(CN[C@@H](CC(N)=O)c2nc([C@@H](N)CO)no2)cn1] |
| 96 | 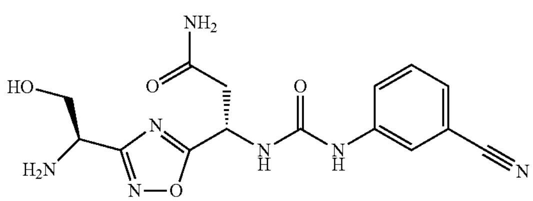 [SMILES: N#Cc1cccc(NC(=O)N[C@@H](CC(N)=O)c2nc([C@@H](N)CO)no2)c1] |
| 97 | 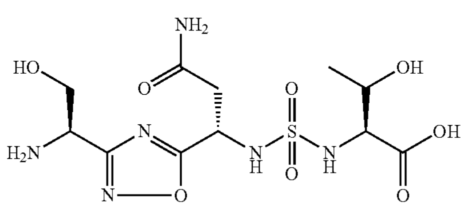 [SMILES: CC(O)[C@H](NS(=O)(=O)N[C@@H](CC(N)=O)c1nc([C@@H](N)CO)no1)C(=O)O] |
| 98 | 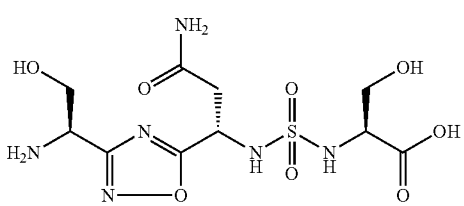 [SMILES: NC(=O)C[C@H](NS(=O)(=O)N[C@@H](CO)C(=O)O)c1nc([C@@H](N)CO)no1] |

-continued
| Compound No. | Structure |
|---|---|
| 99 | 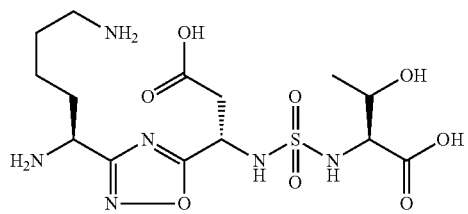 |
| 100 | 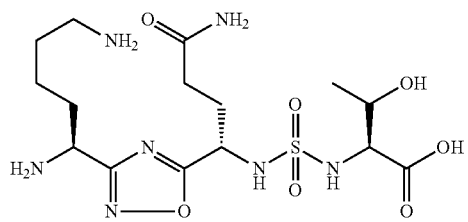 |
| 101 | 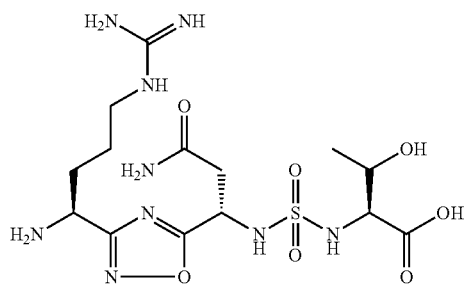 |
| 102 | 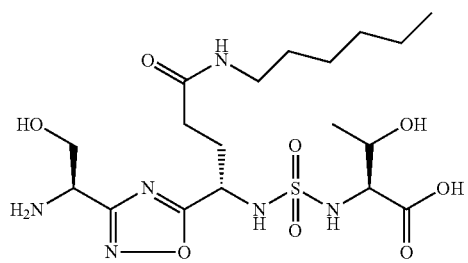 [SMILES: CCCCCCNC(=O)CC[C@H](NS(=O)(=O)N[C@H](C(=O)O)C(C)O)c1nc([C@@H](N)CO)no1] |
| 103 | 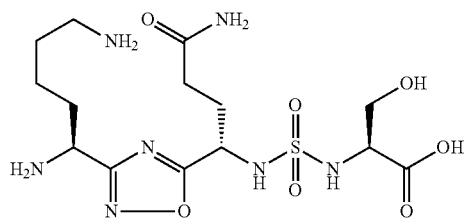 [SMILES: NCCCC[C@H](N)c1noc([C@H](CCC(N)=O)NS(=O)(=O)N[C@@H](CO)C(=O)O)n1] |
| 104 | 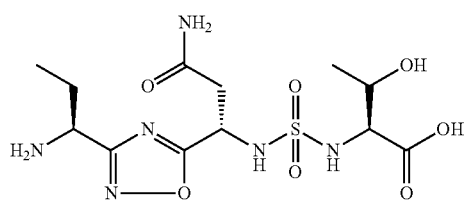 [SMILES: CC[C@H](N)c1noc([C@H](CC(N)=O)NS(=O)(=O)N[C@H](C(=O)O)C(C)O)n1] |

-continued
| Compound No. | Structure |
|---|---|
| 105 | 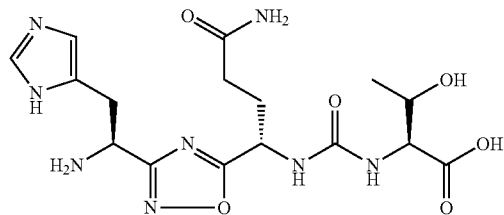 [SMILES: CC(O)[C@H](NC(=O)N[C@@H](CCC(N)=O)c1nc([C@@H](N)Cc2cnc[nH]2)no1)C(=O)O] |
| 106 | 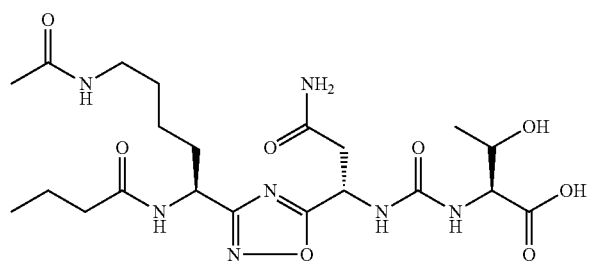 [SMILES: CCCC(=O)N[C@@H](CCCCNC(C)=O)c1noc([C@H](CC(N)=O)NC(=O)N[C@H](C(=O)O)C(C)O)n1] |
| 107 | 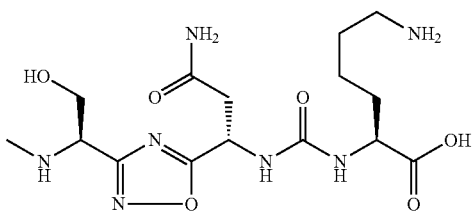 [SMILES: CN[C@@H](CO)c1noc([C@H](CC(N)=O)NC(=O)N[C@@H](CCCCN)C(=O)O)n1] |
| 108 | 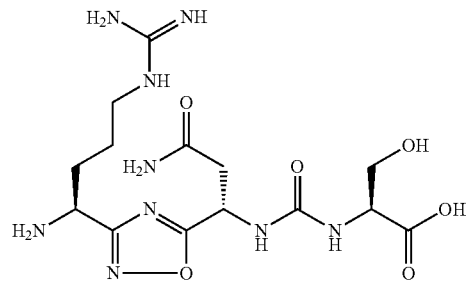 [SMILES: N=C(N)NCCC[C@H](N)c1noc([C@H](CC(N)=O)NC(=O)N[C@@H](CO)C(=O)O)n1] |
| 109 | 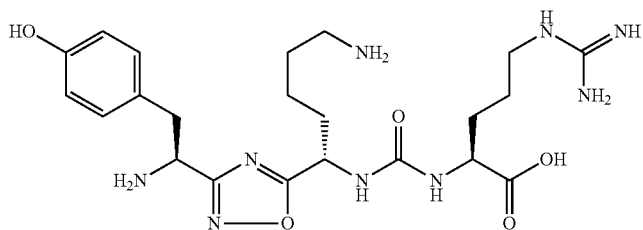 [SMILES: N=C(N)NCCC[C@H](NC(=O)N[C@@H](CCCCN)c1nc([C@@H](N)Cc2ccc(O)cc2)no1)C(=O)O] |
| 110 | 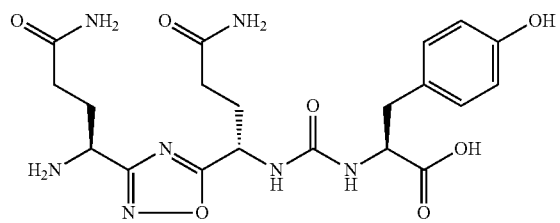 [SMILES: NC(=O)CC[C@H](NC(=O)N[C@@H](Cc1ccc(O)cc1)C(=O)O)c1nc([C@@H](N)CCC(N)=O)no1] |

-continued

| Compound No. | Structure |
|---|---|
| 111 | 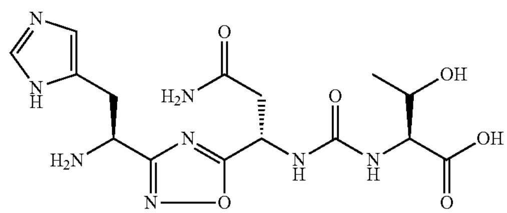 [SMILES: CC(O)[C@H](NC(=O)N[C@@H](CC(N)=O)c1nc([C@@H](N)Cc2cnc[nH]2)no1)C(=O)O] |
| 112 | 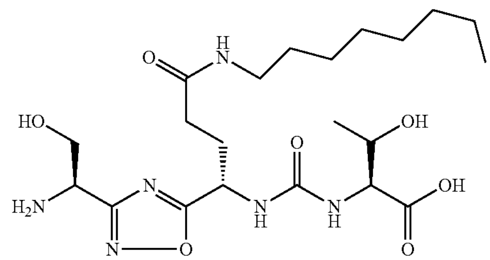 [SMILES: CCCCCCCCNC(=O)CC[C@H](NC(=O)N[C@H](C(=O)O)C(C)O)c1nc([C@@H](N)CO)no1] |
| 113 | 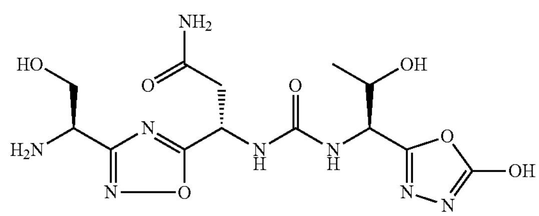 [SMILES: CC(O)[C@H](NC(=O)N[C@@H](CC(N)=O)c1nc([C@@H](N)CO)no1)c1nnc(O)o1] |
| 114 | 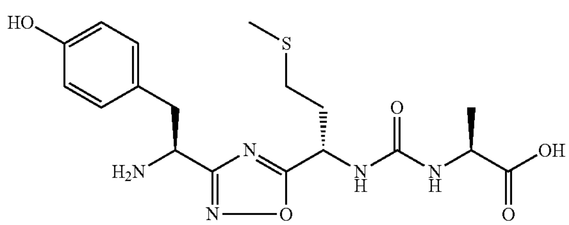 [SMILES: CSCC[C@H](NC(=O)N[C@@H](C)C(=O)O)c1nc([C@@H](N)Cc2ccc(O)cc2)no1] |
| 115 | 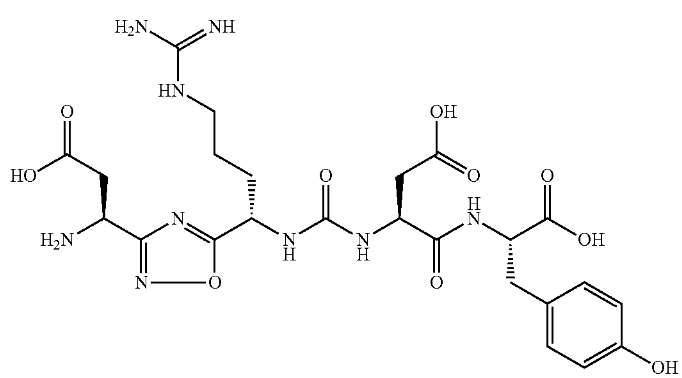 [SMILES: N=C(N)NCCC[C@H](NC(=O)N[C@@H](CC(=O)O)C(=O)N[C@@H](Cc1ccc(O)cc1)C(=O)O)c1nc([C@@H](N)CC(=O)O)no1] |
| 116 | 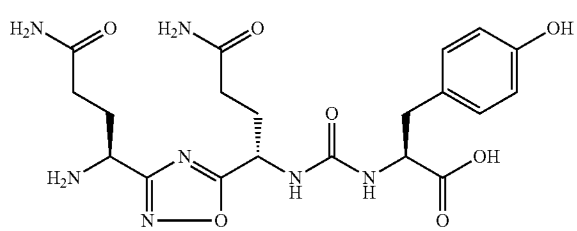 [SMILES: NC(=O)CC[C@H](NC(=O)N[C@@H](Cc1ccc(O)cc1)C(=O)O)c1nc([C@@H](N)CCC(N)=O)no1] |

-continued
| Compound No. | Structure |
|---|---|
| 117 | 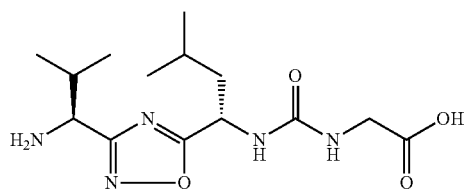 |
| 118 | 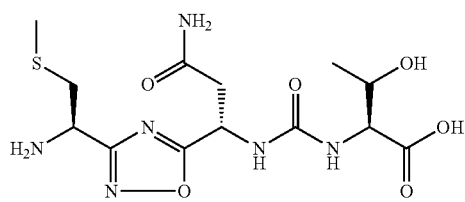 |
| 119 | 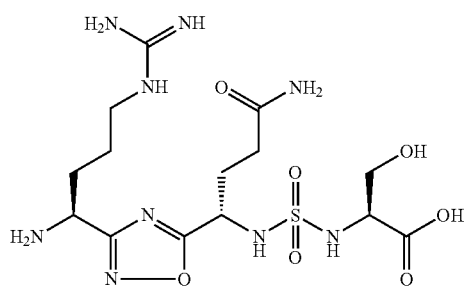 |
| 120 | 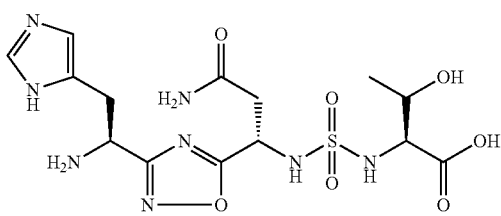 [SMILES: CC(O)[C@H](NS(=O)(=O)N[C@@H](CC(N)=O)c1nc([C@@H](N)Cc2cnc[nH]2)no1)C(=O)O] |
| 121 | 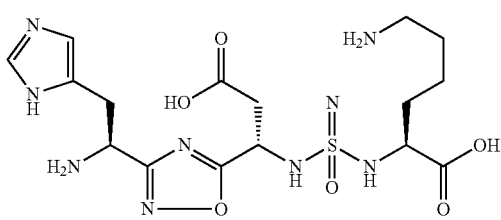 [SMILES: N=S(=O)(N[C@@H](CCCCN)C(=O)O)N[C@@H](CC(=O)O)c1nc([C@@H](N)Cc2cnc[nH]2)no1] |
| 122 | 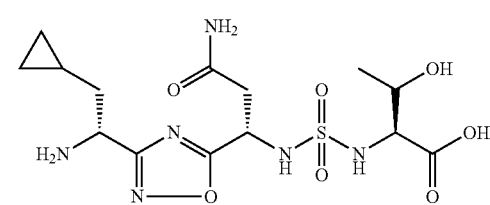 [SMILES: CC(O)[C@H](NS(=O)(=O)N[C@@H](CC(N)=O)c1nc([C@H](N)CC2CC2)no1)C(=O)O] |
| 123 | 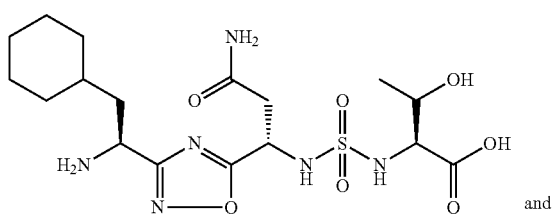 [SMILES: CC(O)[C@H](NS(=O)(=O)N[C@@H](CC(N)=O)c1nc([C@@H](N)CC2CCCCC2)no1)C(=O)O] and |

| Compound No. | Structure |
|---|---|
| 124 | 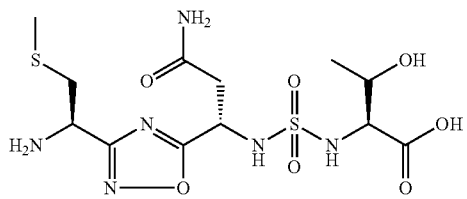 [SMILES: CSC[C@H](N)c1noc([C@H](CC(N)=O)NS(=O)(=O)N[C@H](C(=O)O)C(C)O)n1] | or a pharmaceutically acceptable salt thereof or a stereoisomer thereof.

In certain embodiments, compounds of the invention may be prodrugs of the compounds of formula (I), e.g., wherein a hydroxyl in the parent compound is presented as an ester or a carbonate or carboxylic acid present in the parent compound is presented as an ester. In a further embodiment, the prodrug is metabolized to the active parent compound in vivo (e.g., the ester is hydrolyzed to the corresponding hydroxyl or carboxylic acid).

In certain embodiments, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$ and $^{125}$. Isotopically labeled compounds of the present inventions can generally be prepared by following procedures analogous to those disclosed in the schemes and/or in the examples herein below, by substituting an isotopically labeled reagent for a non-isotopically labeled reagent.

Pharmaceutical Compositions

In certain embodiments, the present invention provides a pharmaceutical composition comprising a compound as disclosed herein, optionally admixed with a pharmaceutically acceptable carrier or diluent.

The present invention also provides methods for formulating the disclosed compounds for pharmaceutical administration.

The compositions and methods of the present invention may be utilized to treat an individual in need thereof. In certain embodiments, the individual is a mammal such as a human or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers or finely divided solid carriers or both and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate and/or any of the following: (1) fillers or extenders, such as starches, lactose, sucrose, glucose, mannitol and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions for rectal, vaginal or urethral administration may be presented as a suppository, which may be prepared by mixing one or more active compounds with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Formulations of the pharmaceutical compositions for administration to the mouth may be presented as a mouthwash or an oral spray or an oral ointment.

Alternatively or additionally, compositions can be formulated for delivery via a catheter, stent, wire or other intraluminal device. Delivery via such devices may be especially useful for delivery to the bladder, urethra, ureter, rectum or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier and with any preservatives, buffers or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to an active compound, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops or administration via an implant).

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents, such as sugars, sodium chloride and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound or combination of compounds employed or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age and medical history of the subject. Other factors which influence the effective amount may include, but are not limited to, the severity of the patient's condition, the disorder being treated, the stability of the compound and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol and the like; and (3) metal-chelating agents, such as citric acid, ethylenediamine tetraacetic acid (EDTA), sorbitol, tartaric acid, phosphoric acid and the like.

Methods of Treatment

The programmed cell death protein 1 pathway (PD-1) pathway has been implicated in a number of diseases and conditions and the pathway is known to regulate various immune responses. Numerous studies have sought to activate immune response by targeting the PD-1 pathway, thereby providing a therapy for certain conditions, such as cancers. In fact, studies indicate that blockade of the PD-1 pathway, for example by inhibiting an immunosuppressive signal induced by PD-1, PD-L1 or PD-L2, leads to anti-tumor activity in various cancers, including lung, breast, colon, renal, bladder, thyroid, prostate, osteosarcoma and Hodgkin's lymphoma.

Furthermore, PD-1 activity has also been associated with autoimmune conditions, such as lupus erythematosus, juvenile idiopathic arthritis and allergic encephalomyelitis.

In certain embodiments, the present invention provides uses of a compound of the present invention for the preparation of a medicament, e.g., for the treatment of cancer.

In certain embodiments, the present invention provides methods for treating cancer, wherein the method comprises administration of a therapeutically effective amount of a compound of the present invention to the subject in need thereof.

In certain embodiments, the present invention provides methods for inhibiting growth of tumour cells and/or metastasis by administering a therapeutically effective amount of compounds of the present invention to the subject in need thereof.

In certain embodiments, the present invention provides methods for inhibiting growth of tumour cells and/or metastasis by administering a therapeutically effective amount of compound of formula (I) to the subject in need thereof.

In certain embodiments, the present invention provides methods for treating cancer, by administering a therapeutically effective amount of compound of formula (I) to the subject in need thereof.

Representative tumour cells include cells of a cancer such as but are not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), non-small cell lung cancer (NSCLC), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos and combinations of said cancers.

In certain embodiments, the present invention provides methods for treating cancer, wherein the cancer is selected from lung cancer, breast cancer, colon cancer, renal cancer, bladder cancer, thyroid cancer, prostate cancer, osteosarcoma and Hodgkin's lymphoma.

In certain embodiments, the present invention provides methods for treating bacterial, viral or fungal infection or an immunological condition, by administering a therapeutically effective amount of compound of formula (I) or a pharmaceutically acceptable salt thereof and a stereoisomer thereof to the subject in need thereof.

In certain embodiments, the present invention provides uses of a compound of the present invention for the preparation of a medicament for the treatment of bacterial, viral and fungal infection, as well as methods of administering a therapeutically effective amount of a compound of the present invention for the treatment of a bacterial, viral or fungal infection.

In certain embodiments, the present invention provides uses of a compound of formula (I) for the preparation of a medicament for the treatment of bacterial, viral and fungal infection, as well as methods of administering a therapeutically effective amount of compound of formula (I) or a pharmaceutically acceptable salt thereof and a stereoisomer thereof for the treatment of a bacterial, viral or fungal infection.

Still yet other embodiments of the present invention provides a method of treatment of infection by blockade of the PD-1 pathway, for example inhibiting an immunosuppressive signal induced by PD-1, PD-L1 or PD-L2, wherein the method comprises administration of a therapeutically effective amount of a compound of the present invention to the subject in need thereof.

In certain embodiments, the invention provides uses of a compound of the present invention in inhibiting the PD-1 pathway (e.g., PD-1, PD-L1 or PD-L2).

In certain embodiments, the present invention provides methods for treating infectious disease in a subject comprising administering a therapeutically effective amount of a compound of the present invention for the treatment of the infectious disease.

In certain embodiments, the present invention provides compound of formula (I) or a pharmaceutically acceptable salt thereof and a stereoisomer thereof for use as a medicament.

In certain embodiments, the present invention provides compound of formula (I) or a pharmaceutically acceptable salt thereof and a stereoisomer thereof for use in the treatment of cancer.

In certain embodiments, the present invention provides compound of formula (I) or a pharmaceutically acceptable salt thereof and a stereoisomer thereof for use in the treatment of lung cancer, breast cancer, colon cancer, renal cancer, bladder cancer, thyroid cancer, prostate cancer, osteosarcoma and Hodgkin's lymphoma.

In certain embodiments, the present invention provides compound of formula (I) or a pharmaceutically acceptable salt thereof and a stereoisomer thereof for use in the treatment of bacterial, viral or fungal infection or an immunological condition.

Representative infectious disease include but are not limited to HIV, Influenza, Herpes, Giardia, Malaria, Leishmania, the pathogenic infection by the virus Hepatitis (A, B, & C), herpes virus (e.g., VZV, HSV-1, HAV-6, HSV-II and CMV, Epstein Barr virus), adenovirus, influenza virus, flaviviruses, echovirus, rhinovirus, coxsackie virus, cornavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumococci, meningococci and conococci, klebsiella, proteus, serratia, pseudomonas, *E. coli*, legionella, diphtheria, salmonella, bacilli, cholera, tetanus, botulism, anthrax, plague, leptospirosis and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum* and pathogenic infection by the parasites *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

The compounds of the present invention may be used as single drugs (monotherapy) or conjointly with one or more other agents (conjoint therapy). The compounds may be used by themselves or, preferably, in a pharmaceutical composition in which the compound is mixed with one or more pharmaceutically acceptable materials.

The pharmaceutical composition may be administered by oral or inhalation routes or by parenteral administration route. For example, compositions can be administered orally, by intravenous infusion, topically, intraperitoneally, intravesically or intrathecally. Examples of parenteral administration includes but are not limited to intraarticular (in the joints), intravenous, intramuscular, intradermal, intraperitoneal and subcutaneous routes. Suitable liquid compositions may be aqueous or non-aqueous, isotonic sterile injection solutions and may contain antioxidants, buffers, bacteriostats and solutes that render the formulation isotonic with the blood of the intended recipient and aqueous and non-aqueous sterile suspensions that can include suspending agents, solubilizers, thickening agents, stabilizers and preservatives. Oral administration, parenteral administration, subcutaneous administration and intravenous administration are preferred methods of administration.

The dosage of the compounds of the present invention varies depending on a patient's age, weight or symptoms, as well as the compound's potency or therapeutic efficacy, the dosing regimen and/or treatment time. Generally, suitable routes of administration may, for example, include oral, eyedrop, rectal, transmucosal, topical or intestinal administration; parenteral delivery, including intramuscular, subcutaneous, intramedullary injections, as well as intrathecal, direct intraventricular, intravenous, intraperitoneal, intranasal or intraocular injections. The compounds of the invention may be administered in an amount of 0.5 mg or 1 mg up to 500 mg, 1 g or 2 g per dosage regimen. The dosage may be administered once per week, once per three days, once per two days, once per day, twice per day, three times per day or more often. In alternative embodiments, in certain adults the compound can be continuously administered by intravenous administration for a period of time designated by a physician. Since the dosage is affected by various conditions, an amount less than or greater than the dosage ranges contemplated about may be implemented in certain cases. A physician can readily determine the appropriate dosage for a patient undergoing therapeutic treatment.

The compounds of the present invention may be administered in combination with one or more other drugs (1) to complement and/or enhance effect of the compound of the present invention, (2) to modulate pharmacodynamics, improve absorption or reduce dosage of the compound of the present invention and/or (3) to reduce or ameliorate the side effects of the compound of the present invention. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours or a week of one another. Thus, an individual who receives such treatment can benefit from a combined effect of different therapeutic compounds. The respective compounds may be administered by the same or different route and the same or different method.

The dosage of the other drug can be a dosage that has been clinically used or may be a reduced dosage that is effective when administered in combination with a compound of the present invention. The ratio of the compound of the present invention and the other drug can vary according to age and weight of a subject to be administered, administration method, administration time, disorder to be treated, symptom and combination thereof. For example, the other drug may be used in an amount of 0.01 to 100 parts by mass, based on 1 part by mass of the compound of the present invention.

Conjoint therapy can be employed to treat any diseases discussed herein. For example, in the methods of the invention directed to the treatment of cancer, the compound of the present invention can be used with an existing chemotherapeutic conjointly using a single pharmaceutical composition or a combination of different pharmaceutical compositions. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, a compound of the invention can be administered conjointly with a cancer treatment adjunct, such as a leucopenia (neutropenia) treatment drug, thrombocytopenia treatment drug, antiemetic and cancer pain intervention drug, concomitantly or in a mixture form. Chemotherapeutic agents that may be conjointly administered with compounds of the invention include: aminoglutethimide, amsacrine, anastrozole, asparaginase, bcg, bicalutamide, bleomycin, bortezomib, buserelin, busulfan, camptothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, pomalidomide, porfimer, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine and vinorelbine.

In certain embodiments, a compound of the invention may be conjointly administered with non-chemical methods of cancer treatment. In a further embodiment, a compound of the invention may be conjointly administered with radiation therapy. In a further embodiment, a compound of the invention may be conjointly administered with surgery, with thermoablation, with focused ultrasound therapy, with cryotherapy or with any combination of these.

In certain embodiments, different compounds of the invention may be conjointly administered with one or more other compounds of the invention. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of the invention provides a synergistic effect. In certain embodiments, conjointly administering one or more additional chemotherapeutics agents provides an additive effect.

The compound of the present invention can be used with one or more other immunomodulators and/or potentiating agents conjointly using a single pharmaceutical composition or a combination of different pharmaceutical compositions. Suitable immunomodulators include various cytokines, vaccines and adjuvants. Examples of cytokines, vaccines and adjuvants that stimulate immune responses include GM-CSF, M-CSF, G-CSF, interferon-$\alpha$, $\beta$ or $\gamma$, IL-1, IL-2, IL-3, IL-12, Poly(I:C) and $C_pG$.

In certain embodiments, the potentiating agents includes cyclophosphamide and analogs of cyclophosphamide, anti-TGF$\beta$ and Imatinib (Gleevec), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists and IL-18 antagonists.

Definitions and Abbreviations

Unless defined otherwise, all technical and scientific terms used herein have the same meaning and the meaning of such terms is independent at each occurrence thereof and is as commonly understood by one of skill in art to which the subject matter herein belongs. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

The term "compounds of the present invention" comprises compounds of formula (I), pharmaceutical acceptable salts thereof and stereoisomers thereof.

The term "acyl" is art-recognized and refers to a group represented by the general formula hydrocarbylC(O)—, preferably alkylC(O)—.

The term "acylamino" refers to an amino group substituted with acyl.

The term "alkoxy" refers to an alkyl group, preferably a lower alkyl group, having an oxygen attached thereto. Representative alkoxy groups include methoxy, ethoxy, propoxy, tert-butoxy and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group. An alkyl group may be optionally substituted at one or more positions as permitted by valence. Such optional substituents include, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl or heteroaryl groups is contemplated.

The term "amide" or "amido" as used herein, refers to a group

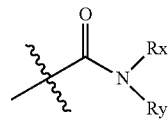

wherein each $R^x$ any $R^y$ independently represent a hydrogen or hydrocarbyl group or both $R^x$ any $R^y$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

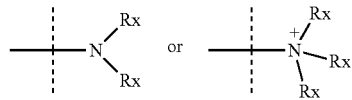

wherein each $R^x$ independently represents a hydrogen or a hydrocarbyl group or two $R^x$ are taken together with the N atom to which they are attached complete a heterocycle having from 4 to 8 atoms in the ring structure.

The term "aminoalkyl", as used herein, refers to an alkyl group substituted with an amino group.

The term "aralkyl" or "arylalkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls and/or heterocyclyls. Aryl groups include benzene, naphthalene, phenanthrene, phenol, aniline and the like.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds. A cycloalkyl group may be substituted at one or more positions, as permitted by valence, with any optional substituents described herein. Cycloalkyl groups include but are not limited to cyclopropyl, cyclobutyl, cyclopentyl and cyclohexyl.

As used herein, the term "cyano" refers to —CN group.

The term "carboxy" or "carboxylic acid", as used herein, refers to a group represented by the formula —$CO_2H$.

The term "carboxylate" refers to a group represented by the formula —$(CO_2)^-$.

The term "ester", as used herein, refers to a group —C(O)OR$^x$ wherein R$^x$ represents a hydrocarbyl group.

As used herein, the term "guanidino" refers to —NH—C(=NH)—$NH_2$ group.

The terms "halo" and "halogen" as used herein means halogen and includes chloro, fluoro, bromo and iodo.

The term "haloalkyl", as used herein, refers to an alkyl group substituted with a halogen group.

As used herein, the term "carbocycle", "carbocyclic" or "carbocyclyl" is intended to mean any stable 3-, 4-, 5-, 6- or 7-membered monocyclic or bicyclic or 7-, 8-, 9-, 10-, 11-, 12- or 13-membered bicyclic or tricyclic hydrocarbon ring, any of which may be saturated, partially unsaturated, unsaturated or aromatic. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl and indanyl. When the term "carbocycle" or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls and/or heterocyclyls. Heteroaryl groups include, for example, pyrrole, furan, thiophene, imidazole, oxazole, thiazole, pyrazole, pyridine, pyrazine, pyridazine, indole, 1,3,4-oxadiazole, pyrimidine and the like. A heteroaryl group may be substituted at one or more positions, as permitted by valence, with any optional substituents described herein.

The term "heteroatom" as used herein means an atom of any element other than carbon or hydrogen. Preferred heteroatoms are nitrogen, oxygen and sulfur.

The terms "heterocyclyl", "heterocycle" and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls and/or heterocyclyls. Heterocyclyl groups include, for example, piperidine, piperazine, pyrrolidine, morpholine, 2,3-dihydrobenzo[b][1,4]dioxine, lactones, lactams and the like. Heterocyclyl groups may be optionally substituted as permitted by valence.

The term "heterocyclylalkyl" or "(heterocyclyl)alkyl", as used herein, refers to an alkyl group substituted with a heterocycle group.

The term "hydroxyalkyl", as used herein, refers to an alkyl group substituted with a hydroxy group.

As used herein, the term "hydroxy" or "hydroxyl" refers to —OH group.

As used herein, the term "nitro" refers to —$NO_2$ group.

The term "lower" when used in conjunction with a chemical moiety, such as, acyl, acyloxy, alkyl, alkenyl, alkynyl or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl or alkoxy substituents defined herein are respectively lower acyl, lower acyloxy, lower alkyl, lower alkenyl, lower alkynyl or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl or an acyl), a thiocarbonyl (such as a thioester, a thioacetate or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "thioalkyl", as used herein, refers to an alkyl group substituted with a thiol group.

The term "thioester", as used herein, refers to a group —C(O)SR$^x$ or —SC(O)R$^x$ wherein R$^x$ represents a hydrocarbyl.

The term "thioacid", "thiocarboxy" or "thiocarboxylic acid", as used herein, refers to a group represented by the formula —C(O)SH.

The term "thiocarboxylate" refers to a group represented by the formula —(C(O)S)$^-$.

As used herein, a therapeutic that "prevents" a disorder or condition refers to a compound that, in a statistical sample, reduces the occurrence of the disorder or condition in the treated sample relative to an untreated control sample or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate or stabilize the existing unwanted condition or side effects thereof).

The term "prodrug" is intended to encompass compounds which, under physiologic conditions, are converted into the therapeutically active agents of the present invention (e.g., a compound of formula (I)). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula (I) in a formulation represented above can be replaced with the corresponding suitable prodrug, e.g., wherein a hydroxyl in the parent compound is presented as an ester or a carbonate or carboxylic acid present in the parent compound is presented as an ester.

As used herein, the term "comprise" or "comprising" is generally used in the sense of include, that is to say permitting the presence of one or more additional (unspecified) features or components.

As used herein, the term "including" as well as other forms, such as "include", "includes," and "included," is not limiting.

As used herein, the term "amino acid" means a molecule containing both an amino group and a carboxyl group and includes its salts, esters, combinations of its various salts, as well as tautomeric forms. In solution, at neutral pH, amino and acid groups of an amino acid can exchange a proton to form a doubly ionized, through overall neutral, entity identified as a zwitterion. In some embodiments, the amino acids are α-, β-, γ- or δ-amino acids, including their stereoisomers and racemates. As used herein, the term "L-amino acid" denotes an α-amino acid having the levorotatory configuration around the α-carbon, that is, a carboxylic acid of general formula CH(COOH)(NH$_2$)-(side chain), having the L-configuration. The term "D-amino acid" similarly denotes a carboxylic acid of general formula CH(COOH)(NH$_2$)-(side chain), having the dextrorotatory-configuration around the α-carbon. Side chains of L-amino acids can include naturally occurring and non-naturally occurring moieties. Non-naturally occurring (i.e., unnatural) amino acid side chains are moieties that are used in place of naturally occurring amino acid side chains in, for example, amino acid analogs.

An "amino acid residue" as used herein, means a moiety sharing structural similarity to the parent amino acid. An amino acid residue may be covalently bonded to another chemical moiety via the amino group of the residue or the carboxylate group of the residue (i.e., a hydrogen atom of —NH$_2$ or —OH is replaced by a bond to another chemical moiety).

As used herein, the phrase "side chain of amino acid" means a moiety that is covalently attached to D or L-amino acid structure and can be represented as CH(COOH)(NH$_2$)—R. For example, in case of alanine CH(COOH)(NH$_2$)(CH$_3$), side chain of amino acid (R) is —CH$_3$. Examples of "side chain of amino acid" include, but are not limited to, (C$_1$-C$_6$)alkyl, (C$_2$-C$_6$)alkenyl or (C$_2$-C$_6$)alkynyl. The side chain of amino acid may be substituted by one or more, same or different substituents selected from, but are not limited to, amino, amido, alkylamino, acylamino, carboxylic acid, carboxylate, thiocarboxylate, thioacid, -hydroxy, cycloalkyl, (cycloalkyl)alkyl, aryl, heterocyclyl, heteroaryl, guanidino, —SH, —S(alkyl); optionally wherein cycloalkyl, aryl, heterocyclyl and heteroaryl are further substituted by one or more substituents such as hydroxy, alkoxy, halo, amino, nitro, cyano or alkyl.

Amino acids include the twenty standard amino acids used by most biological organisms in protein synthesis. Unnatural amino acid residues may be selected from, but are not limited to, alpha and alpha-disubstituted amino acids, N-alkyl amino acids and natural amino acids substituted with lower alkyl, aralkyl, hydroxyl, aryl, aryloxy, haloalkyl or acyl.

For example, lysine can be substituted to form an unnatural amino acid, e.g., at a carbon atom of its side chain or alternatively by mono- or dialkylation of its terminal NH$_2$ group (e.g., wherein the amino group of the lysine sidechain is taken together with its substituents to form a heterocyclic ring such as piperidine or pyrrolidine). In another example, the terminal amino group of the lysine sidechain can form a ring with the amino acid backbone, as in capreomycidine. Further unnatural derivatives of lysine include homolysine and norlysine. The sidechain of lysine can alternatively be substituted by a second amino group. In another example, the alkyl portion of the lysine side chain can be incorporated into a carbocyclic ring structure to form a semirigid analog, such as, e.g., cyclohexyl or cyclopentyl.

Throughout this specification and claims, the 'L-threonine residue' and/or 'side chain of L-threonine' mentioned in compound of formula (I), and/or preparation thereof can be represented by any one of the following formulae.

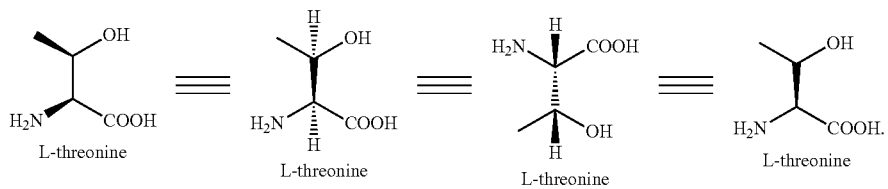

In certain embodiments, the unnatural amino acid can be a derivative of a natural amino acid having one or more double bonds.

In other example embodiments, in threonine, the beta-methyl group can be replaced with an ethyl, phenyl or other higher alkyl group. In histidine, the imidazole moiety can be substituted or alternatively, the alkylene backbone of the side chain can be substituted.

Further examples of unnatural amino acids include homoserine and homologs of natural amino acids.

In further example embodiments, an unnatural amino acid can be alkylated (e.g., methylated) at the alpha position.

Further examples of unnatural amino acids include alpha, beta- and beta, gamma-dehydroamino amino acid analogs.

Further exemplary amino acids include penicillamine and betamethoxyvaline.

Further examples of unnatural amino acids include the amino acids wherein the side chain comprises amino, alkylamino, acylamino, —COO-alkyl, cycloalkyl, heterocyclyl, heteroaryl, guanidino, (cycloalkyl)alkyl, (heterocyclyl)alkyl and (heteroaryl)alkyl.

"Modified N-terminal amino group" and "modified C-terminal carboxyl group" mean that the amino group or carboxyl group is altered.

Modification of the N-terminal amino group is preferably with the general formula —$NR_xR_y$; wherein $R_x$ is hydrogen or alkyl and $R_y$ is alkyl, alkenyl, —C(=NH)$NH_2$, alkynyl, acyl, cycloalkyl, aryl or heterocyclyl.

Examples of N-terminal modifications include, but are not limited to, are acetylated, formylated or guanylated N-termini.

Modification of the C-terminal carboxyl group is preferably with the general formula $COR_z$ ($R_z$ replaces the hydroxyl group of the last amino acid); wherein $R_z$ is —$NR_7R_8$, alkoxy, amino or an imide. The C-terminal carboxyl group may also be transformed into a heterocyclic ring (such as a 1,2,4-oxadiaxole or 1,3,4-oxadiaxole ring) optionally substituted by hydroxy, alkyl, hydroxyalkyl, alkoxyalkyl or cycloalkyl.

This invention includes pharmaceutically acceptable salts of compounds of the invention and their use in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide and the like. Mixtures of such solvates can also be prepared. The source of such solvate can be from the solvent of crystallization, inherent in the solvent of preparation or crystallization or adventitious to such solvent.

"Pharmaceutically acceptable" means that which is useful in preparing a pharmaceutical composition that is generally safe, non-toxic and neither biologically nor otherwise undesirable and includes that which is acceptable for veterinary as well as human pharmaceutical use.

The term "stereoisomers" refers to any enantiomers, diastereoisomers or geometrical isomers, such as of the compounds of the invention. When compounds of the invention are chiral, they can exist in racemic or in optically active form. Since the pharmaceutical activity of the racemates or stereoisomers of the compounds according to the invention may differ, it may be desirable to use compounds that are enriched in one of the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline) or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de or even 95% or greater de.

The term "subject" includes mammals (especially humans) and other animals, such as domestic animals (e.g., household pets including cats and dogs) and non-domestic animals (such as wildlife).

Naturally-occurring amino acids are identified throughout the description and claims by the conventional three-letter abbreviations indicated in the below table.

TABLE

(Amino acid codes)

| Name | 3-letter code |
|---|---|
| Alanine | Ala |
| Arginine | Arg |
| Asparagine | Asn |
| Aspartic acid | Asp |
| Glutamic acid | Glu |
| Glutamine | Gln |
| Histidine | His |
| Isoleucine | Ile |
| Lysine | Lys |
| Methionine | Met |
| Phenylalanine | Phe |
| Proline | Pro |
| Serine | Ser |
| Threonine | Thr |
| Tyrosine | Tyr |
| Valine | Val |

The abbreviations used in the entire specification may be summarized herein below with their particular meaning.

° C. (degree Celsius); % (percentage); brine (NaCl solution); $CH_2Cl_2$/DCM (Dichloromethane); Boc (Tert-butyloxycarbonyl); Bzl (Benzyloxy-carbonyl); $Cs_2CO_3$ (Caesium carbonate); DIC: N,N'-Diisopropylcarbodiimide; DIPEA (N,N-Diisopropylethylamine); DMF (Dimethyl formamide); EtOH (Ethanol); $Et_2NH$ (Diethylamine); Fmoc (9-Fluorenylmethyloxycarbonyl); g or gr (gram); HOBt (1-Hydroxy benzotriazole); h or hr (Hours); HPLC (High-performance liquid chromatography); $K_2CO_3$ (Potassium carbonate); LCMS (Liquid chromatography mass spectroscopy); $Liq.NH_3$ (Liquid ammonia); mmol (Millimoles); M (Molar); µl (Microlitre); mL (Millilitre); mg (Milligram); MS (ES) (Mass spectroscopy-electro spray); min (Minutes); Na (Sodium); $NaHCO_3$ (Sodium bicarbonate); $NH_2NH_2.H_2O$ (Hydrazine hydrate); NMM (N-Methylmorpholine); $Na_2SO_4$ (Sodium sulphate); $NH_2OH.HCl$ (Hydroxylamine hydrochloride); PD1/PD-1 (Programmed cell death 1); PD-L1 (Programmed death-ligand 1); PD-L2 (Programmed cell death 1 ligand 2); prep-HPLC/preparative HPLC (Preparative High-performance liquid chromatography); $TEA/Et_3N$ (Triethylamine); TFAA: Tifluoroacetic anhydride; TLC (Thin Layer Chromatography); THF (Tetrahydrofuran); TIPS (Triisopropylsilane); TFA (Trifluoroacetic acid); $t_R$ (Retention time); Trt (Trityl or Triphenylmethyl), etc.

Experimental

The present invention provides methods for the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention.

The intermediates or starting materials required for the synthesis are commercially available (commercial sources such as Sigma-Aldrich, USA or Germany; Chem-Impex USA; G.L. Biochem, China and Spectrochem, India) or alternatively, these intermediates or starting materials can be prepared using known literature methods. The invention is described in greater detail by way of specific examples.

Purification and Characterization of Compounds
Analytical HPLC Method:

Analytical HPLC was performed on ZIC HILIC 200 A° column (4.6 mm×250 mm, 5 µm), Flow rate: 1.0 mL/min. The elution conditions used are: Buffer A: 5 mmol ammonium acetate, Buffer B: Acetonitrile, Equilibration of the column with 90% buffer B and elution by a gradient of 90% to 40% buffer B during 30 min.

Preparative HPLC Method:

Preparative HPLC was performed on SeQuant ZIC HILIC 200 A° column (10 mm×250 mm, 5 µm), Flow rate: 5.0 mL/min. The elution conditions used are: Buffer A: 5 mmol ammonium acetate (adjust to pH-4 with Acetic Acid), Buffer B: Acetonitrile, Equilibration of the column with 90% buffer B and elution by a gradient of 90% to 40% buffer B during 20 min.

LCMS was performed on AP1 2000 LC/MS/MS triple quad (Applied biosystems) with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

EXAMPLES

Example 1: Synthesis of Compound 1

Step 1a

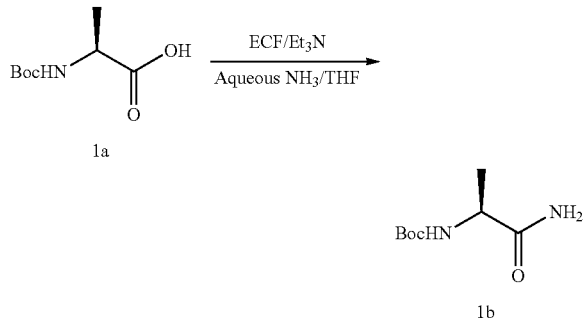

Ethylchloroformate (3.4 g, 31.3 mmol) and $Et_3N$ (7.0 mL, 52.8 mmol) were added to a solution of compound 1a (5.0 g, 26.4 mmol) in THF (20 mL) and stirred at −20° C. for 20 min. After 20 minutes 25% of aqueous ammonia (10 mL, 132.0 mmol) was added to the active mixed anhydride and stirred at 0-5° C. for 30 min. The completeness of the reaction was confirmed by TLC analysis. The volatiles were evaporated under reduced pressure and partitioned between water and ethyl acetate. The organic layer was washed with $NaHCO_3$ solution followed by citric acid solution and brine solution. The separated organic layer was dried over $Na_2SO_4$, filtered and evaporated under reduced pressure to yield 4.0 g of compound 1b. LCMS: 89.3 (M-Boc+H)$^+$.

Step 1b

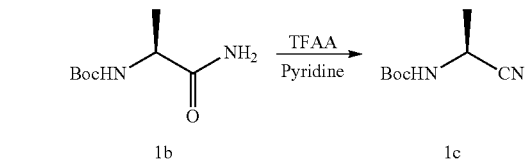

Trifluroacetic anhydride (8.4 g, 39.9 mmol) was added to a solution of compound 1b (5 g, 26.6 mmol) in pyridine (21.0 mL, 26.6 mmol) and stirred at room temperature for 2 h. The completeness of the reaction was confirmed by TLC analysis. The volatiles were evaporated under reduced pressure and partitioned between water and ethyl acetate. The organic layer was washed with NaHCO₃ solution followed by citric acid solution and brine solution. The separated organic layer was dried over Na₂SO₄, filtered and evaporated under reduced pressure to yield 3.5 g of compound 1c, which was used for next step directly.

Step 1c:

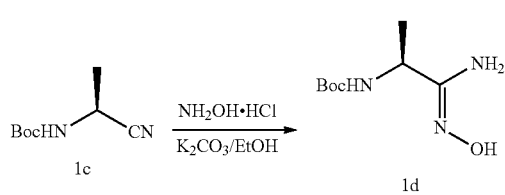

Hydroxylamine hydrochloride (0.92 g, 13.2 mmol), water (0.5 mL) and potassium carbonate (1.8 g, 13.2 mmol) were added to a solution of compound 1c (1.5 g, 8.8 mmol) in EtOH (20 mL) and stirred at 86° C. for 4 h. The completeness of the reaction was confirmed by TLC analysis. The volatiles were evaporated under reduced pressure and partitioned between water and ethyl acetate. The organic layer was washed with brine solution, dried over Na₂SO₄ then filtered and evaporated under reduced pressure to yield 0.9 g of compound 1d. LCMS: 104.3 (M-Boc+H)⁺.

Step 1d:

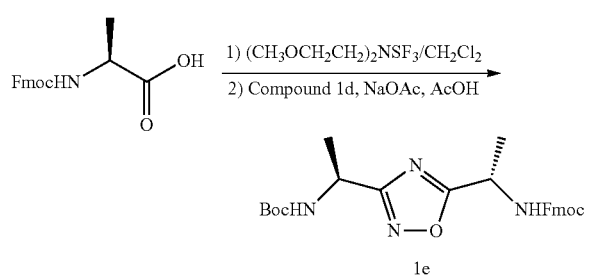

Deoxo-Fluor (3.7 g, 16.1 mmol) was added to a solution of Fmoc-Ala-OH (5.0 g, 15.0 mmol) in CH₂Cl₂ (50 mL) and stirred at 0° C. for 1 h. Then CH₂Cl₂ was evaporated and triturated with hexane. Sodium acetate (0.2 g, 2.4 mmol) and compound d (0.5 g, 2.4 mmol) in acetic acid were taken in a round neck flask and stirred for 30 minutes. To this mixture, was added Fmoc-Ala-COF (0.996 g, 3.1 mmol) and stirred at room temperature for 30 min. The reaction mixture was stirred at 90° C. for 3 h. The completeness of the reaction was confirmed by TLC analysis. The volatiles were evaporated under reduced pressure and partitioned between water and ethyl acetate. The organic layer was washed with NaHCO₃ solution followed by citric acid solution and brine solution. The separated organic layer was dried over Na₂SO₄, filtered and evaporated under reduced pressure to get residue. The residue was purified by silica gel column chromatography (eluent: 0-5% ethyl acetate in hexane) to yield 0.3 g of compound e. LCMS: 379.0 (M-Boc+H)⁺, 501.3 (M+Na)⁺.

Step 1e:

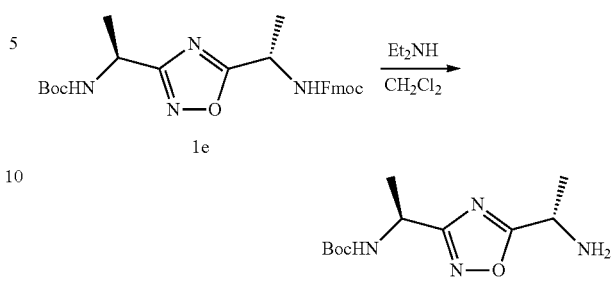

Diethylamine (1.0 mL) was added to a solution of compound 1e (0.35 g, 0.73 mmol) in CH₂Cl₂ (10 mL). The mixture was stirred at room temperature for 3 h and then the resulting solution was concentrated under nitrogen atmosphere and washed with diethyl ether and centrifuged to yield 0.18 g compound 1f, which was used for next step directly.

Step 1f:

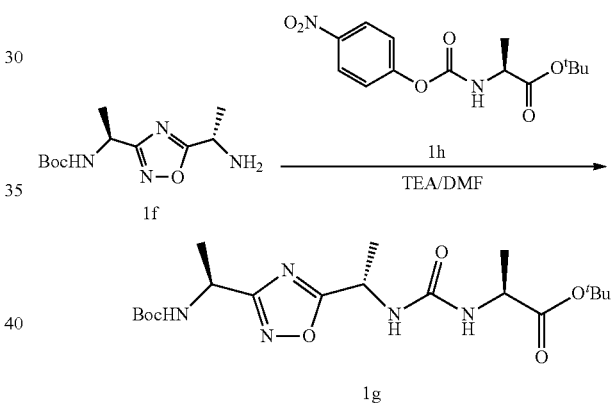

The urea linkage was carried out using coupling of compound 1f (0.18 g, 0.71 mmol) in DMF (5.0 mL) with compound 1h (0.24 g, 0.77 mmol) at room temperature. The coupling was initiated by the addition of TEA (0.2 mL g, 1.4 mmol) and the resultant mixture was stirred at room temperature. After the completion of 3 h, the reaction mass was partitioned between water and ethyl acetate. The organic layer was washed with water followed by brine solution and dried over Na₂SO₄. The separated organic layer was filtered and evaporated under reduced pressure to yield 0.2 g of compound 1g. LCMS: 450.1 (M+Na)⁺.

Step 1g:

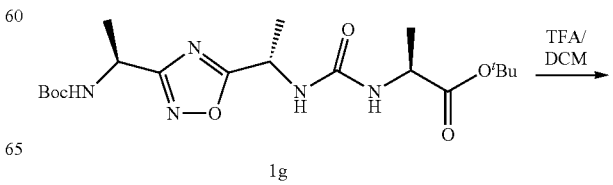

77
-continued

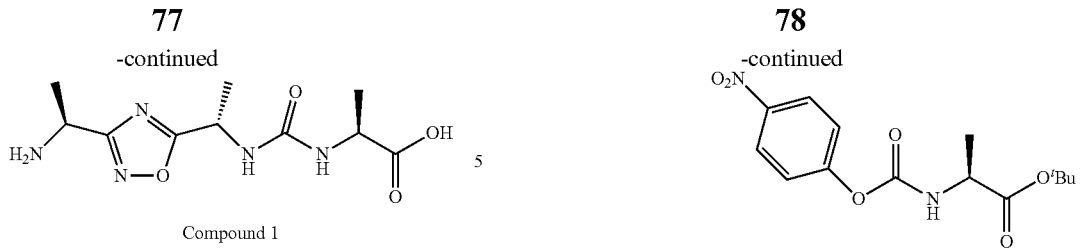

Compound 1

To a solution of compound 1g (0.15 g, 0.35 mmol) in CH$_2$Cl$_2$ (1 mL) were added trifluoroacetic acid (0.5 mL) and catalytic amount of triisopropylsilane and stirred at room temperature for 3 h. The resulting solution was concentrated under reduced pressure to yield 0.10 g of crude compound. The crude solid material was purified as prep HPLC method described under experimental conditions. LCMS: 272.2 (M+H)$^+$; HPLC (t$_R$): 6.2 min.

Synthesis of Compound 1h:

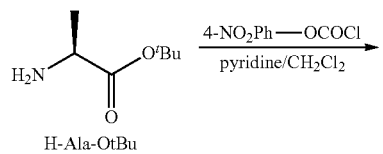

78
-continued

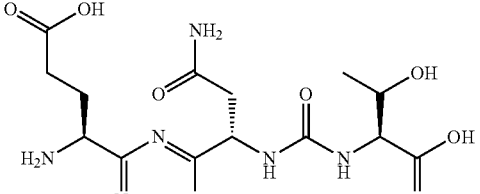

1h

Pyridine (12.0 g, 25.2 mmol) was added to a solution of H-Ala-OtBu (2.3 g, 12.6 mmol) in CH$_2$Cl$_2$ (20 mL) and the resulting solution was stirred at room temperature for 5-10 min. Solution of 4-Nitrophenyl chloroformate (2.8 g, 13.8 mmol) in CH$_2$Cl$_2$ (20 mL) was added to the above reaction mixture and stirring was continued at room temperature for 1 h. The completeness of the reaction was confirmed by TLC analysis. After completion of reaction it was diluted with CH$_2$Cl$_2$ (50 mL) and washed with 1.0 M of sodium bisulphate solution (50 mL×2) followed by 1.0 M sodium carbonate solution (50 mL×2). The organic layer was dried over Na$_2$SO$_4$, filtered and evaporated under reduced pressure to yield crude compound, which was purified by silica gel column chromatography (eluent: 0-20% ethyl acetate in hexane) to yield 2.0 g of compound 1h.

The below compounds were prepared by procedure similar to the one described in Example 1 (compound 1) with appropriate variations in reactants or amino acids, solvents, quantities of reagents and reaction conditions. The analytical data of the compounds are summarized herein below table.

| Compound No. | Structure | LCMS (M + H)$^+$ | HPLC (t$_R$ in min) |
|---|---|---|---|
| 2. | 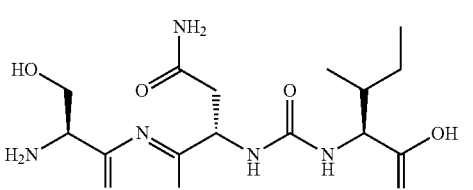 | 403.2 | 12.6 |
| 3. | 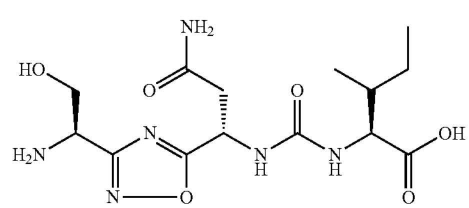 [SMILES: CCC(C)[C@H](NC(=O)N[C@@H](CC(N)=O)c1nc([C@@H](N)CO)no1)C(=O)O] | 373.1 | 9.4 |
| 4. | 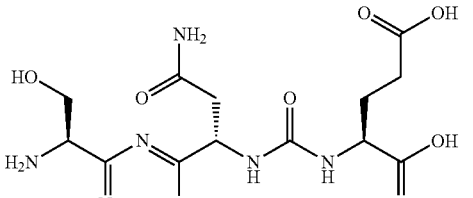 | 389.1 | 13.1 |

| Compound No. | Structure | LCMS (M + H)+ | HPLC (tR in min) |
|---|---|---|---|
| 5. | 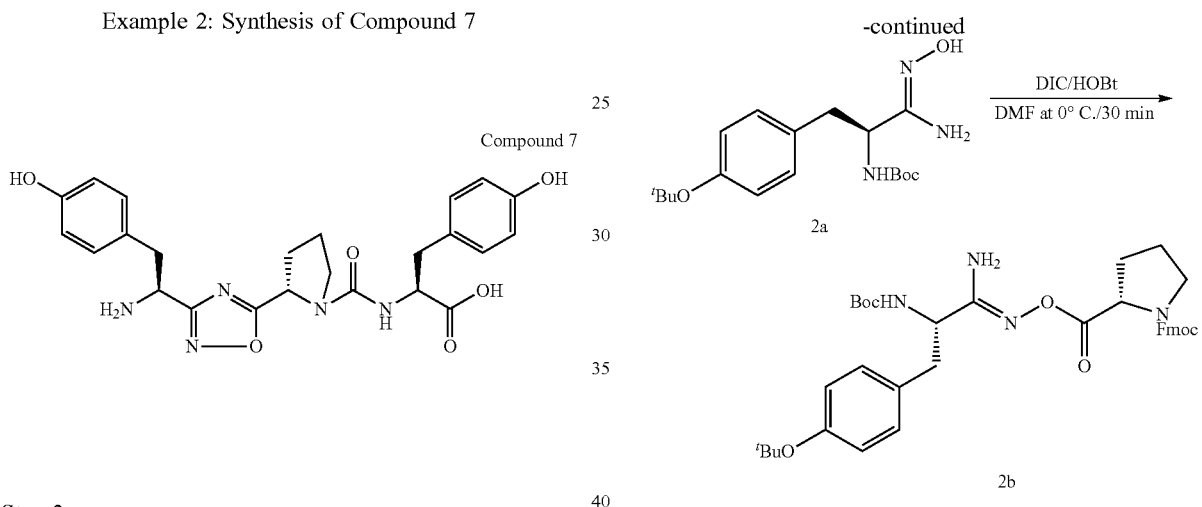 | 388.1 | 21.9 |
| 6. | 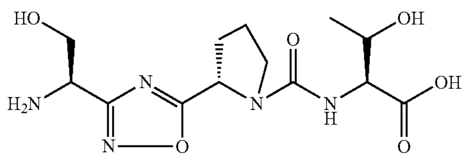 [SMILES: CC(O)[C@H](NC(=O)N1CCC[C@H]1c1nc([C@@H](N)CO)no1)C(=O)O] | 344.2 | 12.4 |

Example 2: Synthesis of Compound 7

Compound 7

Step-2a:

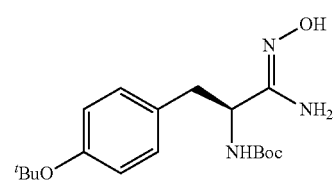

2a

Compound 2a was synthesized using similar procedure as depicted in step 1a to 1c of Example 1 (Compound 1) by using Boc-Tyr(tBu)-OH instead of Boc-Ala-OH to yield 9 g compound 2a.

Step-2b:

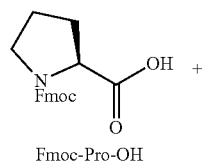

Fmoc-Pro-OH

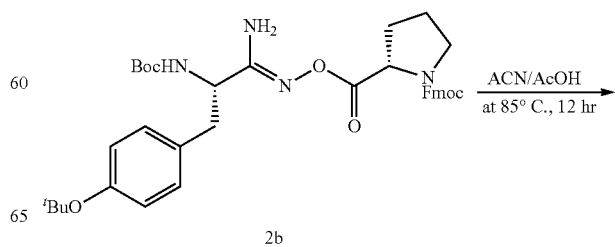

HOBt (3.45 g, 30.8 mmol) and DIC (4.5 mL, 30.8 mmol) were added to a solution of Fmoc-Pro-OH (8.6 g, 25.6 mmol) in DMF (250 mL) at 0° C. and stirred for 30 minutes. Compound 2a (9 g, 25.6 mmol) was further added to the above reaction mixture at the same temperature and continued stirring for 2 h at 0° C. followed by 2 h at room temperature. The completeness of the reaction was confirmed by TLC analysis. The reaction mixture was quenched with ice water, the precipitated white solid was filtered, washed with water (1 L) and dried under high under reduced pressure. The solid was stirred with diethyl ether (500 mL) for 15 min, filtered and dried to yield 14 g of compound 2b. LCMS: 671.3 (M+H)+, 693.3 (M+Na)+.

Step 2c:

-continued

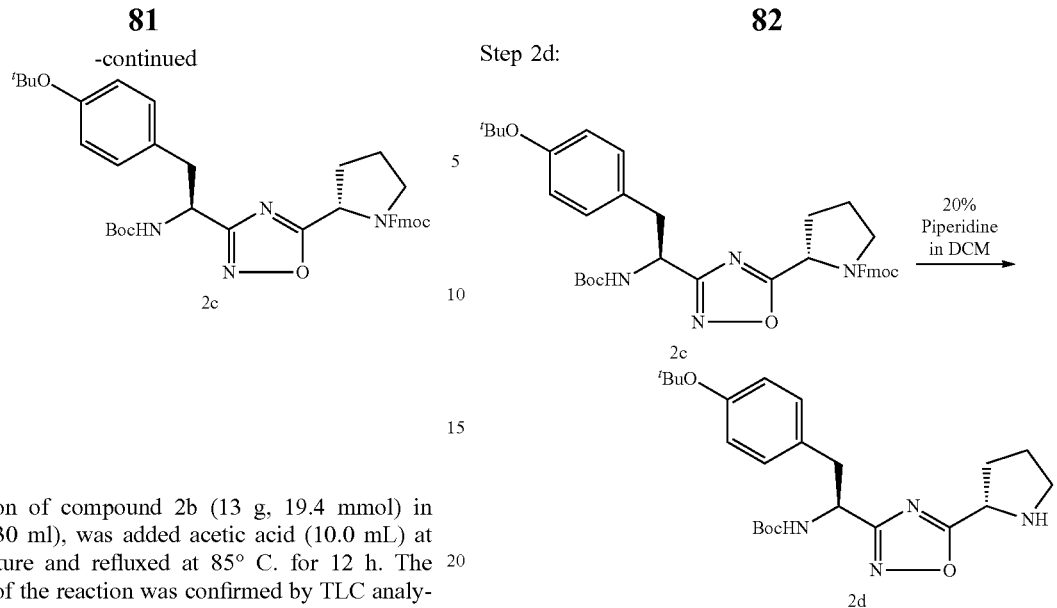

Step 2d:

To a solution of compound 2b (13 g, 19.4 mmol) in acetonitrile (130 ml), was added acetic acid (10.0 mL) at room temperature and refluxed at 85° C. for 12 h. The completeness of the reaction was confirmed by TLC analysis. The volatiles were evaporated under reduced pressure to obtain crude semi solid which was diluted with water and ethyl acetate. The organic layer was washed with NaHCO$_3$ solution followed by citric acid solution and brine solution. The organic layer was dried over Na$_2$SO$_4$, filtered and evaporated under reduced pressure to yield crude solid which was diluted with 10% acetonitrile in hexane (500 ml) and stirred for 2 h to obtain white solid. The white solid was filtered and washed with n-pentane (500 L) and dried to yield 13 g of compound 2c. LCMS: 653.4 (M+H)$^+$, 675.6 (M+Na)$^+$.

Compound 2c (13 g, 19.9 mmol) was added to a solution of 20% piperidine in DCM (150 mL) at 0° C. and stirred at 0° C. for 1 h. The completeness of the reaction was confirmed by TLC analysis. The reaction mixture was concentrated under reduced pressure and diluted with hexane, stirred and filtered. The filtered solid was dissolved in EtOAc and washed with sat. NaHCO$_3$ solution, brine solution, dried over Na$_2$SO$_4$ filtered and evaporated to yield white compound 2d. LCMS 431.1 (M+H)$^+$; 453.4 (M+Na)$^+$.

Step 2e:

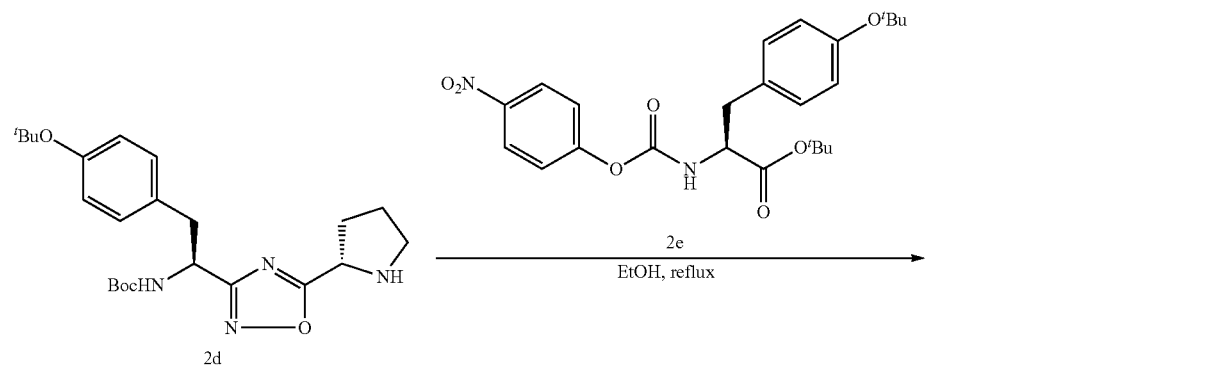

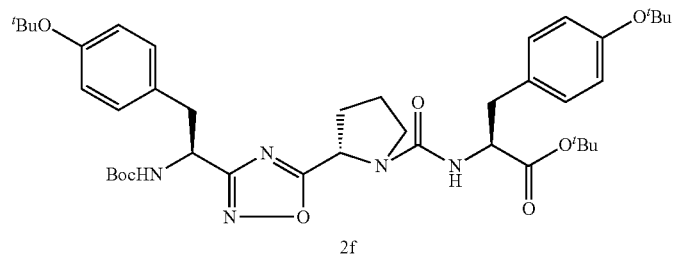

DIPEA was added to a solution of compound 2e (5 g, 11.6 mmol) and compound 2d (5.3 g, 11.6 mmol) in dry THF (50 mL) at 0° C. and stirred for 2 h. The reaction mixture was allowed to stir at ambient temperature for an additional 4 h. The volatiles were evaporated and portioned between ethyl acetate and water. The organic layer was washed with saturated NaHCO₃ 10% citric acid, brine solution, dried over Na₂SO₄ and concentrated under reduced pressure. The crude compound was purified by column chromatography over neutral alumina using 25% ethyl acetate in hexane to yield compound 2f. LCMS: 772.5 (M+Na)⁺.

Step 2f:

A solution of compound 2f (6.5 g, 8.7 mmol) and trifluoroacetic acid (16 mL) in DCM (16 mL) were stirred at 0° C. for one hour. The resulting reaction mixture was evaporated under reduced pressure, diluted with diethyl ether and filtered to yield 4 g of crude compound. The crude solid material was purified by preparative HPLC method described under experimental conditions. LCMS: 482.3 (M+H)⁺; HPLC: $t_R$=12.92 min.

Synthesis of Compound 2e:

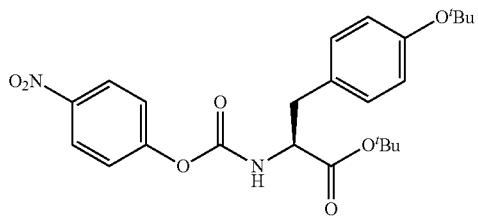 [SMILES: CC(C)(C)OC(=O)[C@H](Cc1ccc(OC(C)(C)C)cc1)NC(=O)Oc1ccc([N+](=O)[O-])cc1]

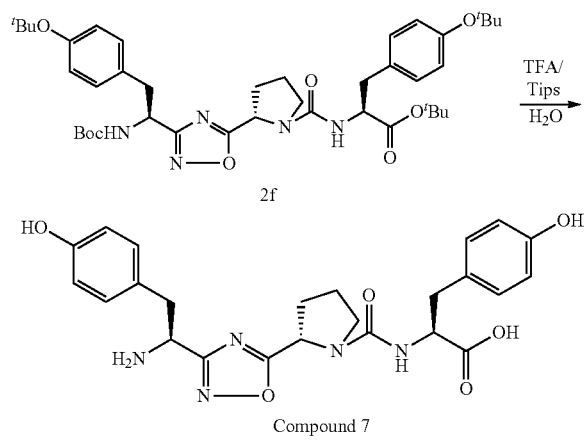

The compound was synthesized using similar procedure as depicted for compound 1h in Example 1, by using H-Tyr(tBu)-OtBu instead of H-Ala-OtBu.

The below compounds were prepared by procedure similar to the one described in Example 2 (Compound 7) with appropriate variations in reactants or amino acids, solvents, quantities of reagents and reaction conditions. The analytical data of the compounds are summarized herein below table.

| Compound No. | Structure | LCMS (M + H)⁺ | HPLC ($t_R$, min) |
|---|---|---|---|
| 8. | 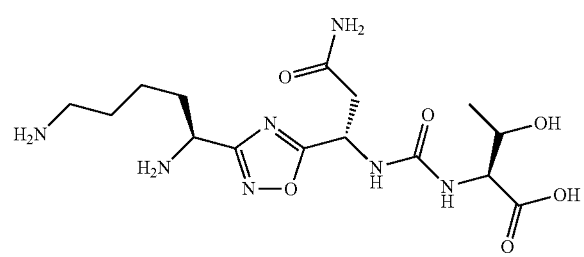 [SMILES: CC(O)[C@H](NC(=O)N[C@@H](CC(N)=O)c1nc([C@@H](N)CCCCN)no1)C(=O)O] | 402.3 | 11.87 |
| 9. | 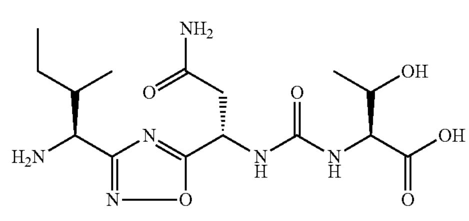 [SMILES: CCC(C)[C@H](N)c1noc([C@H](CC(N)=O)NC(=O)N[C@H](C(=O)O)C(C)O)n1] | 387.0 | 11.8 |
| 10. | 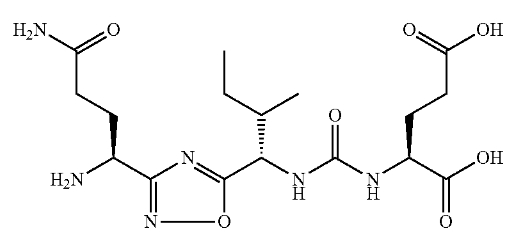 [SMILES: CCC(C)[C@H](NC(=O)N[C@@H](CCC(=O)O)C(=O)O)c1nc([C@@H](N)CCC(N)=O)no1] | 428.9 | 9.2 |

-continued

| Compound No. | Structure | LCMS (M + H)⁺ | HPLC (t_R, min) |
|---|---|---|---|
| 11. | 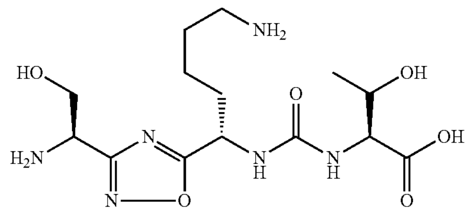 [SMILES: CC(O)[C@H](NC(=O)N[C@@H](CCCCN)c1nc([C@@H](N)CO)no1)C(=O)O] | 375.1 | 10.6 |
| 12. | 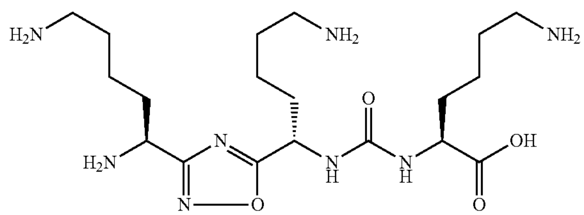 [SMILES: NCCCC[C@H](NC(=O)N[C@@H](CCCCN)c1nc([C@@H](N)CCCCN)no1)C(=O)O] | 443.2 | — |
| 13. | 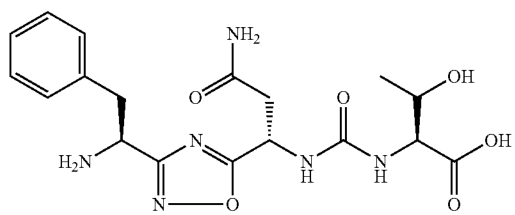 [SMILES: CC(O)[C@H](NC(=O)N[C@@H](CC(N)=O)c1nc([C@@H](N)Cc2ccccc2)no1)C(=O)O] | 421 | 11.0 |
| 14. | 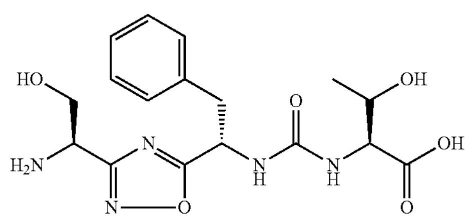 [SMILES: CC(O)[C@H](NC(=O)N[C@@H](Cc1ccccc1)c1nc([C@@H](N)CO)no1)C(=O)O] | 394.3 | 7.6 |
| 15. | 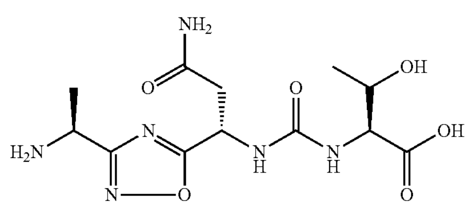 [SMILES: CC(O)[C@H](NC(=O)N[C@@H](CC(N)=O)c1nc([C@H](C)N)no1)C(=O)O] | 345.3 | 12.7 |
| 16. | 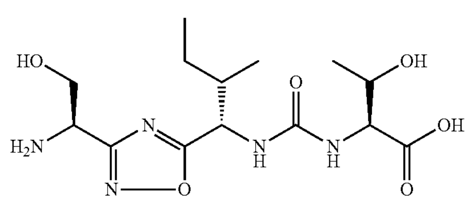 [SMILES: CCC(C)[C@H](NC(=O)N[C@H](C(=O)O)C(C)O)c1nc([C@@H](N)CO)no1] | 360.3 | 8.4 |
| 17. | 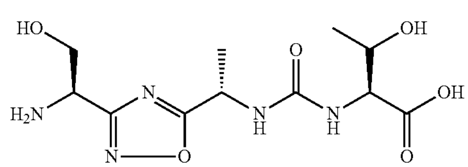 [SMILES: CC(O)[C@H](NC(=O)N[C@@H](C)c1nc([C@@H](N)CO)no1)C(=O)O] | 318.0 | 11.3 |

-continued

| Compound No. | Structure | LCMS (M + H)+ | HPLC (t_R, min) |
|---|---|---|---|
| 18. | 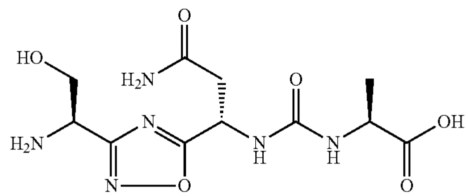 [SMILES: C[C@H](NC(=O)N[C@@H](CC(N)=O)c1nc([C@@H](N)CO)no1)C(=O)O] | 331.0 | 12.5 |
| 19. | 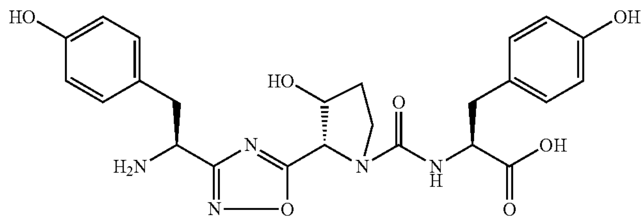 | 498.4 | 7.6 |
| 20. | 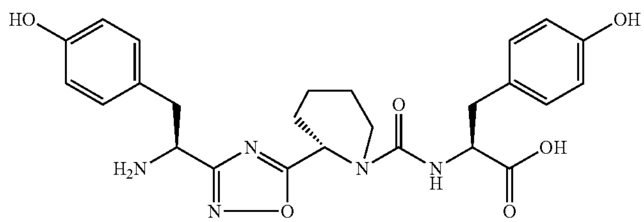 [SMILES: N[C@@H](Cc1ccc(O)cc1)c1noc([C@@H]2CCCCN2C(=O)N[C@@H](Cc2ccc(O)cc2)C(=O)O)n1] | 496.3 | 5.6 |
| 21. | 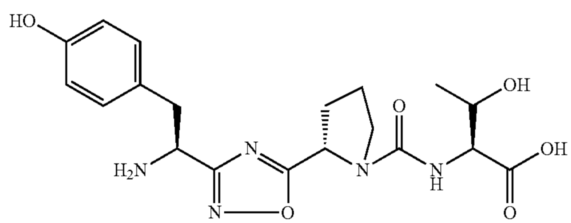 [SMILES: CC(O)[C@H](NC(=O)N1CCC[C@H]1c1nc([C@@H](N)Cc2ccc(O)cc2)no1)C(=O)O] | 420.3 | 7.7 |
| 22. | 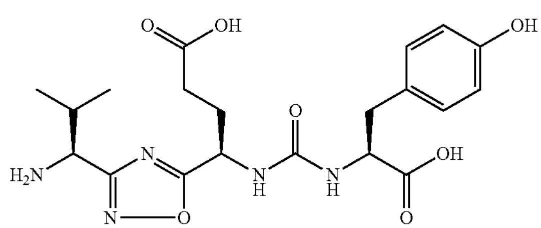 [SMILES: CC(C)[C@H](N)c1noc([C@@H](CCC(=O)O)NC(=O)N[C@@H](Cc2ccc(O)cc2)C(=O)O)n1] | 450.4 | 11.4 |
| 23. | 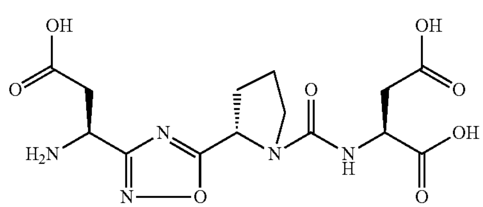 [SMILES: N[C@@H](CC(=O)O)c1noc([C@@H]2CCCN2C(=O)N[C@@H](CC(=O)O)C(=O)O)n1] | 386.1 | 14.5 |
| 24. | 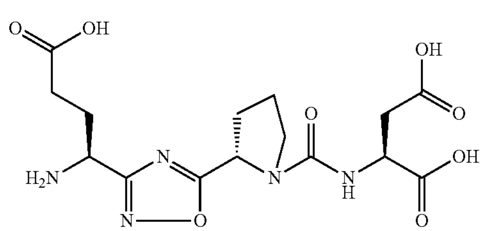 [SMILES: N[C@@H](CCC(=O)O)c1noc([C@@H]2CCCN2C(=O)N[C@@H](CC(=O)O)C(=O)O)n1] | 400.0 | 14.0 |

-continued

| Compound No. | Structure | LCMS (M + H)+ | HPLC (t_R, min) |
|---|---|---|---|
| 25. | 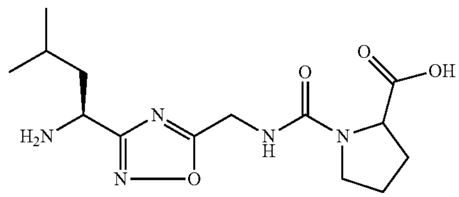 [SMILES: CC(C)C[C@H](N)c1noc(CNC(=O)N2CCCC2C(=O)O)n1] | 325.7 | 10.3 |
| 26. | 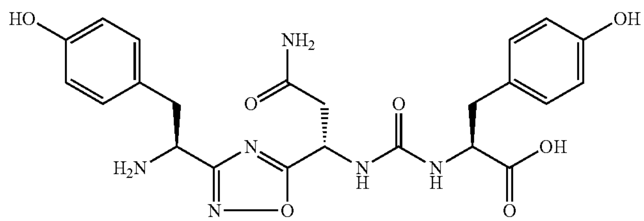 [SMILES: NC(=O)C[C@H](NC(=O)N[C@@H](Cc1ccc(O)cc1)C(=O)O)c1nc([C@@H](N)Cc2ccc(O)cc2)no1] | 499.3 | 9.4 |
| 27. | 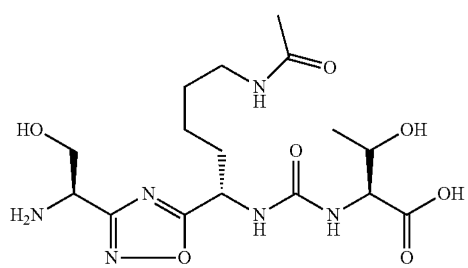 [SMILES: CC(=O)NCCCC[C@H](NC(=O)N[C@H](C(=O)O)C(C)O)c1nc([C@@H](N)CO)no1] | 417.3 | 13.1 |
| 28. | 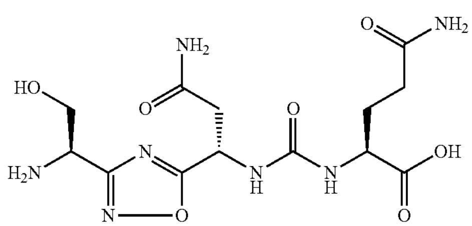 [SMILES: NC(=O)CC[C@H](NC(=O)N[C@@H](CC(N)=O)c1nc([C@@H](N)CO)no1)C(=O)O] | 387.9 | 14.9 |
| 29. | 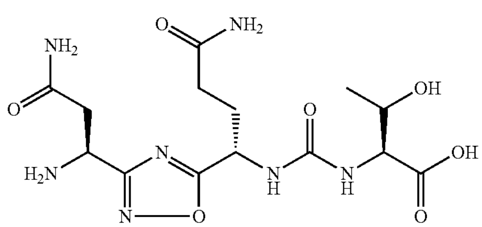 [SMILES: CC(O)[C@H](NC(=O)N[C@@H](CCC(N)=O)c1nc([C@@H](N)CC(N)=O)no1)C(=O)O] | 401.3 | 14.0 |
| 30. | 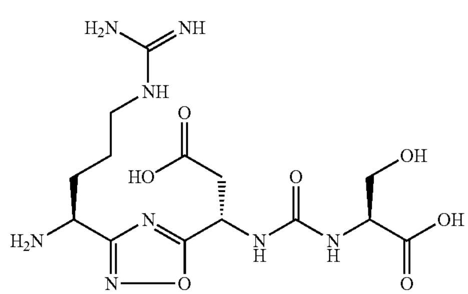 [SMILES: N=C(N)NCCC[C@H](N)c1noc([C@H](CC(=O)O)NC(=O)N[C@@H](CO)C(=O)O)n1] | 416.2 | 13.4 |

-continued

| Compound No. | Structure | LCMS (M + H)+ | HPLC (t_R, min) |
|---|---|---|---|
| 31. | 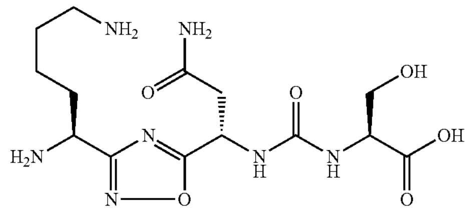 | 388.1 | 11.2 |
| 32. | 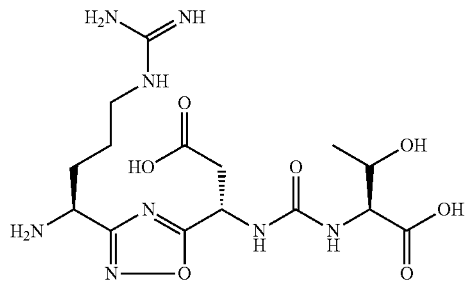 [SMILES: CC(O)[C@H](NC(=O)N[C@@H](CC(=O)O)c1nc([C@@H](N)CCCNC(=N)N)no1)C(=O)O] | 431.2 | 18.9 |
| 33. | 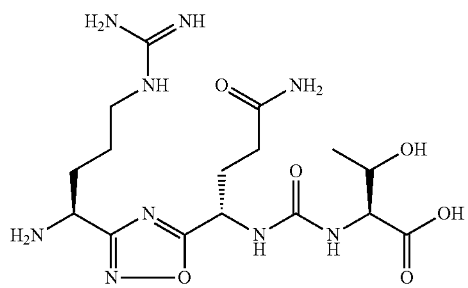 [SMILES: CC(O)[C@H](NC(=O)N[C@@H](CCC(N)=O)c1nc([C@@H](N)CCCNC(=N)N)no1)C(=O)O] | 444.4 | 12.2 |
| 34. | 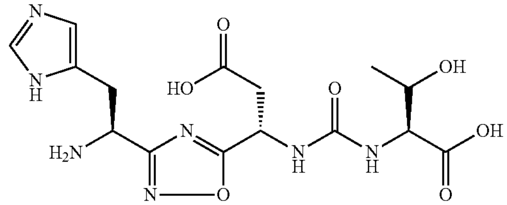 [SMILES: CC(O)[C@H](NC(=O)N[C@@H](CC(=O)O)c1nc([C@@H](N)Cc2cnc[nH]2)no1)C(=O)O] | 412.2 | 15.4 |
| 35. | 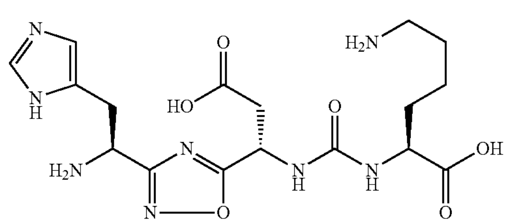 [SMILES: NCCCC[C@H](NC(=O)N[C@@H](CC(=O)O)c1nc([C@@H](N)Cc2cnc[nH]2)no1)C(=O)O] | 439.3 | 11.5 |
| 36. | 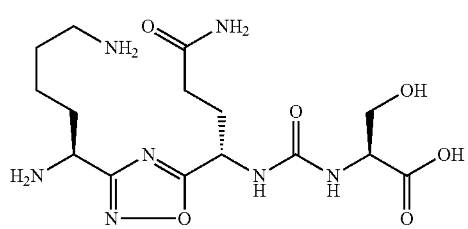 | 402.4 | 11.9 |

-continued

| Compound No. | Structure | LCMS (M + H)+ | HPLC (t_R, min) |
|---|---|---|---|
| 37. | 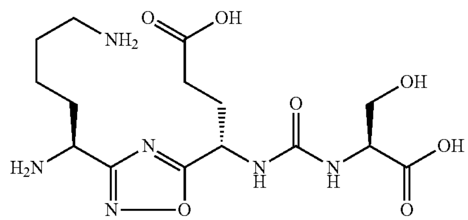 | 403.1 | 8.5 |
| 38. | 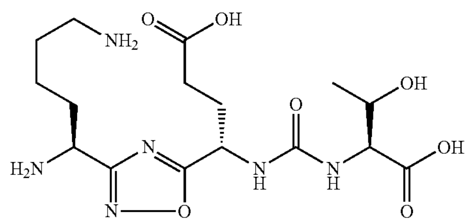 [SMILES: CC(O)[C@H](NC(=O)N[C@@H](CCC(=O)O)c1nc([C@@H](N)CCCCN)no1)C(=O)O] | 417.0 | 8.4 |
| 39. | 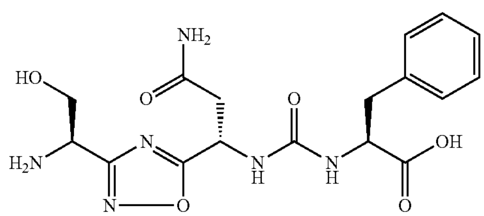 [SMILES: NC(=O)C[C@H](NC(=O)N[C@@H](Cc1ccccc1)C(=O)O)c1nc([C@@H](N)CO)no1] | 407.5 | 12.2 |
| 40. | 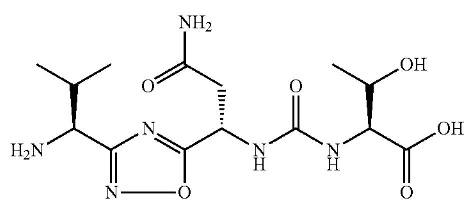 [SMILES: CC(O)[C@H](NC(=O)N[C@@H](CC(N)=O)c1nc([C@@H](N)C(C)C)no1)C(=O)O] | 373.1 | 12.7 |
| 41. | 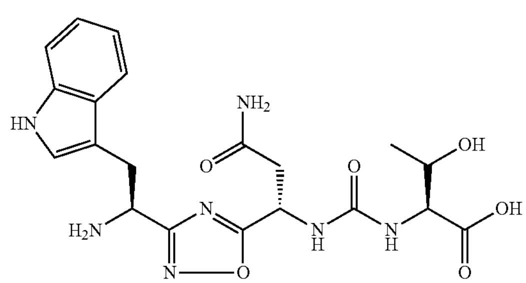 [SMILES: CC(O)[C@H](NC(=O)N[C@@H](CC(N)=O)c1nc([C@@H](N)Cc2c[nH]c3ccccc23)no1)C(=O)O] | 460.2 | 11.9 |
| 42. | 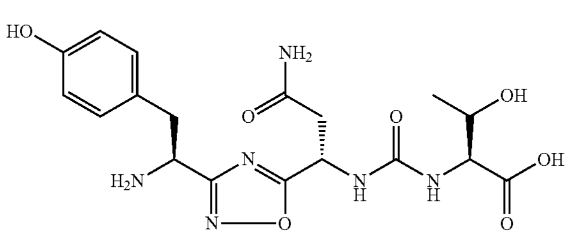 [SMILES: CC(O)[C@H](NC(=O)N[C@@H](CC(N)=O)c1nc([C@@H](N)Cc2ccc(O)cc2)no1)C(=O)O] | 437.2 | 12.9 |

-continued

| Compound No. | Structure | LCMS (M + H)+ | HPLC (t_R, min) |
|---|---|---|---|
| 43. | 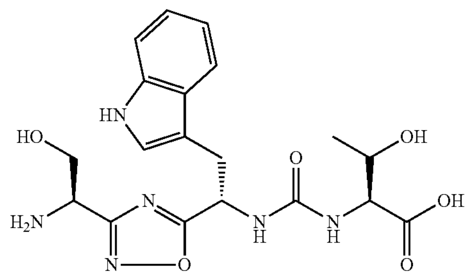 [SMILES: CC(O)[C@H](NC(=O)N[C@@H](Cc1c[nH]c2ccccc12)c1nc([C@@H](N)CO)no1)C(=O)O] | 433.3 | 11.6 |
| 44. | 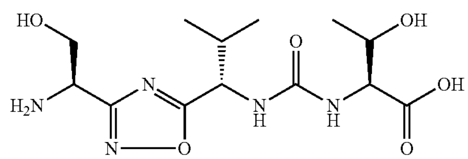 [SMILES: CC(O)[C@H](NC(=O)N[C@H](c1nc([C@@H](N)CO)no1)C(C)C)C(=O)O] | 346.5 | 11.9 |
| 45. | 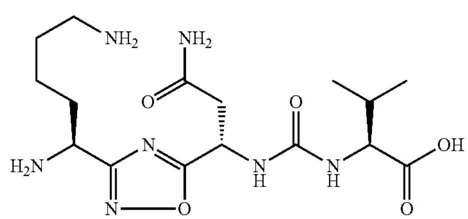 [SMILES: CC(C)[C@H](NC(=O)N[C@@H](CC(N)=O)c1nc([C@@H](N)CCCCN)no1)C(=O)O] | 400.1 | 10.6 |
| 46. | 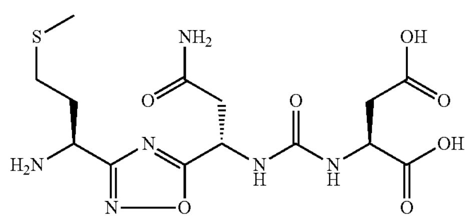 [SMILES: CSCC[C@H](N)c1noc([C@H](CC(N)=O)NC(=O)N[C@@H](CC(=O)O)C(=O)O)n1] | 419.0 | 12.7 |
| 47. | 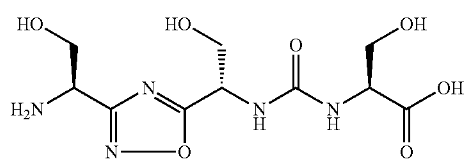 [SMILES: N[C@@H](CO)c1noc([C@H](CO)NC(=O)N[C@@H](CO)C(=O)O)n1] | 320.1 | 14.9 |
| 48. | 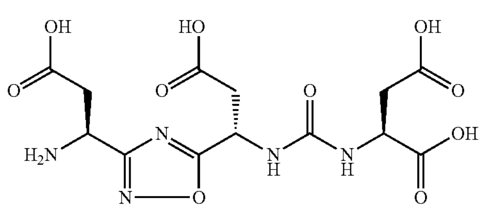 [SMILES: N[C@@H](CC(=O)O)c1noc([C@H](CC(=O)O)NC(=O)N[C@@H](CC(=O)O)C(=O)O)n1] | 404.1 | 14.7 |
| 49. | 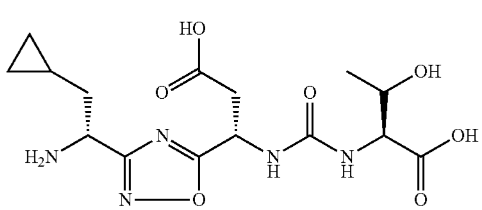 [SMILES: CC(O)[C@H](NC(=O)N[C@@H](CC(=O)O)c1nc([C@H](N)CC2CC2)no1)C(=O)O] | 385.1 | 12.6 |

-continued

| Compound No. | Structure | LCMS (M + H)⁺ | HPLC (t_R, min) |
|---|---|---|---|
| 50. | 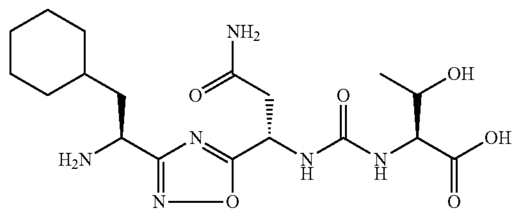 [SMILES: CC(O)[C@H](NC(=O)N[C@@H](CC(N)=O)c1nc([C@@H](N)CC2CCCCC2)no1)C(=O)O] | 427.0 | 10.9 |
| 51. | 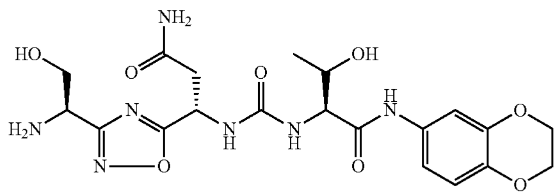 [SMILES: CC(O)[C@H](NC(=O)N[C@@H](CC(N)=O)c1nc([C@@H](N)CO)no1)C(=O)Nc1ccc2c(c1)OCCO2] | 493.3 | 13.8 |
| 52. | 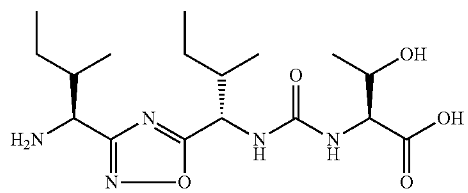 [SMILES: CCC(C)[C@H](N)c1noc([C@@H](NC(=O)N[C@H](C(=O)O)C(C)O)C(C)CC)n1] | 386.1 | 8.5 |
| 53. | 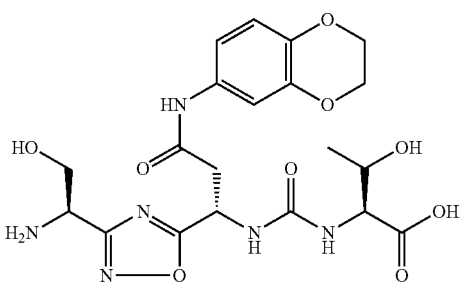 [SMILES: CC(O)[C@H](NC(=O)N[C@@H](CC(=O)Nc1ccc2c(c1)OCCO2)c1nc([C@@H](N)CO)no1)C(=O)O] | 495.0 | 11.2 |
| 54. | 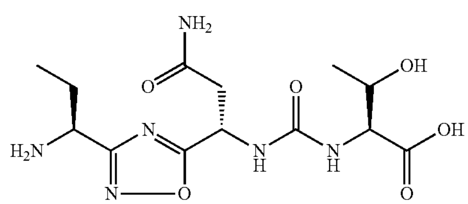 [SMILES: CC[C@H](N)c1noc([C@H](CC(N)=O)NC(=O)N[C@H](C(=O)O)C(C)O)n1] | 359.0 | 14.0 |
| 56. | 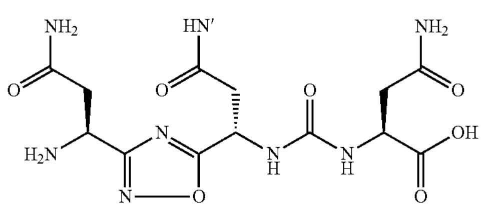 | 401.0 | 13.6 |
| 58. | 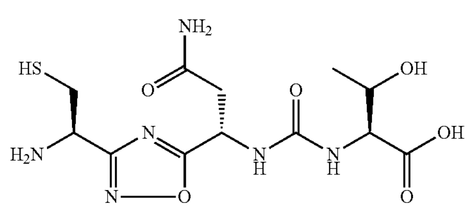 [SMILES: CC(O)[C@H](NC(=O)N[C@@H](CC(N)=O)c1nc([C@@H](N)CS)no1)C(=O)O] | 374.9 | 14.1 |

-continued

| Compound No. | Structure | LCMS (M + H)+ | HPLC (t_R, min) |
|---|---|---|---|
| 59. | 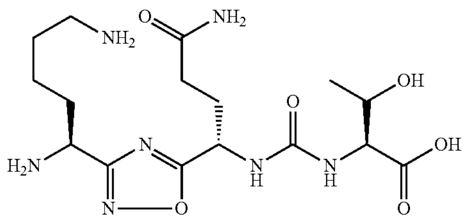 | 416.1 | 12.9 |
| 60. | 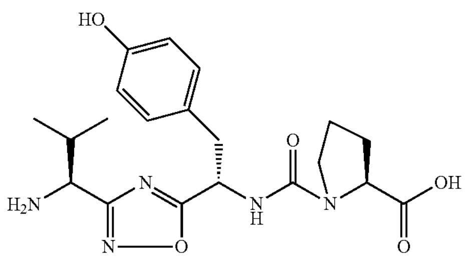 [SMILES: CC(C)[C@H](N)c1noc([C@H](Cc2ccc(O)cc2)NC(=O)N2CCC[C@H]2C(=O)O)n1] | 420.1 | 10.6 |
| 62. | 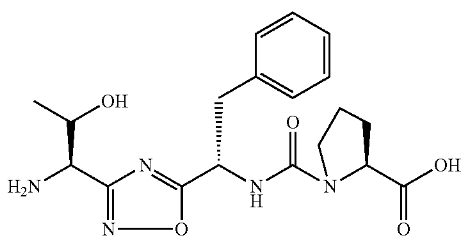 [SMILES: CC(O)[C@H](N)c1noc([C@H](Cc2ccccc2)NC(=O)N2CCC[C@H]2C(=O)O)n1] | 403.9 | 9.2 |
| 63. | 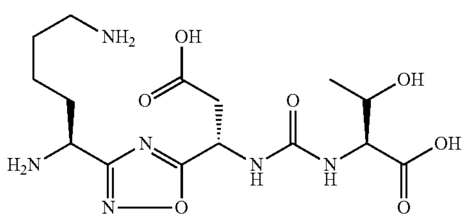 [SMILES: CC(O)[C@H](NC(=O)N[C@@H](CC(=O)O)c1nc([C@@H](N)CCCCN)no1)C(=O)O] | 403.1 | 14.8 |
| 64. | 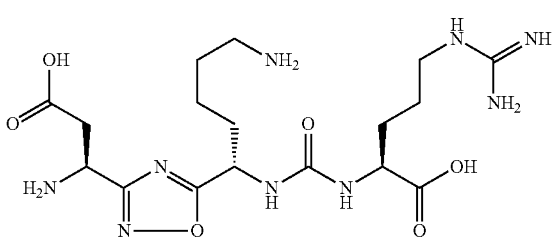 [SMILES: N=C(N)NCCC[C@H](NC(=O)N[C@@H](CCCCN)c1nc([C@@H](N)CC(=O)O)no1)C(=O)O] | 458.5 | 11.8 |
| 65. | 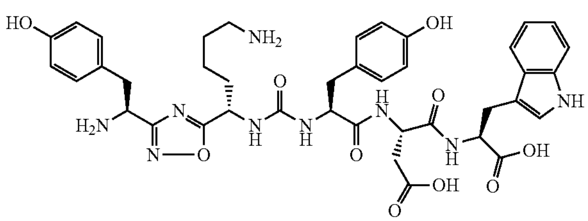 [SMILES: NCCCC[C@H](NC(=O)N[C@@H](Cc1ccc(O)cc1)C(=O)N[C@@H](CC(=O)O)C(=O)N[C@@H](Cc1c[nH]c2ccccc12)C(=O)O)c1nc([C@@H](N)Cc2ccc(O)cc2)no1] | 814.1 | 14.9 |

| Compound No. | Structure | LCMS (M + H)+ | HPLC ($t_R$, min) |
|---|---|---|---|
| 73. | 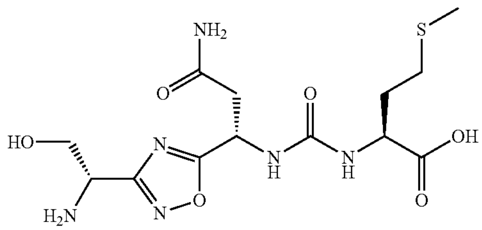 [SMILES: CSCC[C@H](NC(=O)N[C@@H](CC(N)=O)c1nc([C@H](N)CO)no1)C(=O)O] | 391.6 | — |
| 74. | 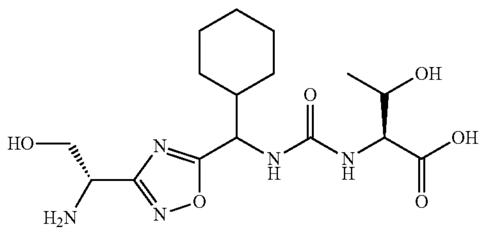 [SMILES: CC(O)[C@H](NC(=O)NC(c1nc([C@H](N)CO)no1)C1CCCCC1)C(=O)O] | 386.1 | — |

Example 3: Synthesis of Compound 75

Compound 75

The compound was synthesized using similar procedure as depicted in Example 2 by using compound 3b (prepared as per the procedure given below) instead of Fmoc-Pro-OH. The crude solid material was purified using preparative HPLC described under experimental conditions. LCMS: 417.5 (M+H)+, HPLC: $t_R$=12.2 min.

Synthesis of Compound 3b:

Step 3a:

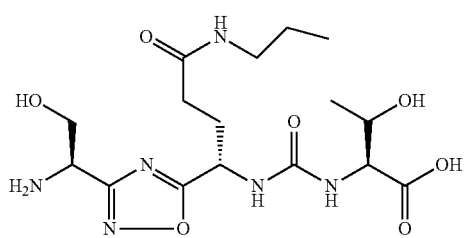

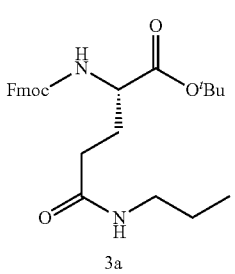

Propylamine (2.9 mL, 35.25 mmol), HATU (14.8 g, 38.8 mmol) and DIPEA (12.3 mL, 70.5 mmol) were added to a solution of Fmoc-Glu-OtBu (15.0 g, 35.3 mmol) in DMF (50 mL) at 0° C. and stirred at room temperature for 1.5 h. The completion of the reaction was confirmed by TLC analysis. The reaction mixture was quenched with water, the resulting solid was filtered, washed with diethyl ether, dried under reduced pressure to yield compound 3a (19.0 g) and used for the next step without purification. LCMS: 489.4 (M+Na+H)+.

Step 3b:

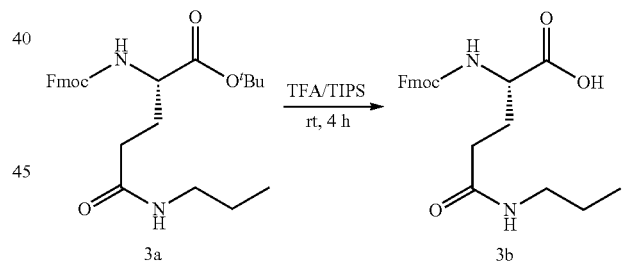

To a solution of compound 3a (19.0 g, 40.72 mmol) in trifluoroacetic acid (19.0 mL) catalytic amount of triisopropylsilane was added and stirred at room temperature for 4 h. The resulting solution was evaporated under nitrogen, washed with diethyl ether to obtain 13.3 g of crude compound which was used for the next step without purification. LCMS: 417.5 (M+H)+.

The below compounds were prepared by procedure similar to the one described in Example 3 with appropriate variations in reactants or amino acids, solvents, quantities of reagents and reaction conditions. The analytical data of the compounds are summarized herein below table.

| Compound No. | Structure | LCMS (M + H)+ | HPLC (t_R, min) |
|---|---|---|---|
| 76. | 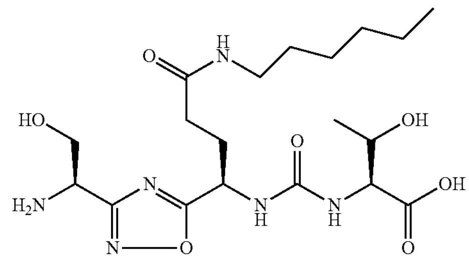 [SMILES: CCCCCCNC(=O)CC[C@@H](NC(=O)N[C@H](C(=O)O)C(C)O)c1nc([C@@H](N)CO)no1] | 459.3 | 9.8 |
| 77. | 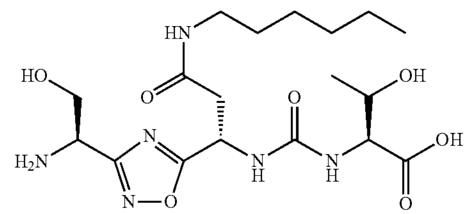 [SMILES: CCCCCCNC(=O)C[C@H](NC(=O)N[C@H](C(=O)O)C(C)O)c1nc([C@@H](N)CO)no1] | 445.0 | 9.6 |
| 78. | 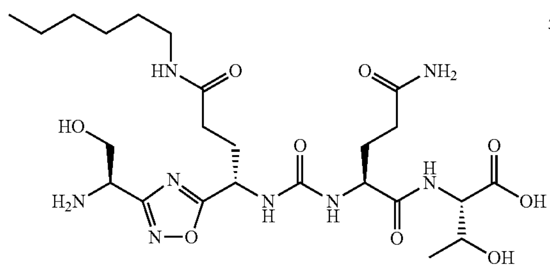 | 587.3 | 10.7 |

Example 4: Synthesis of Compound 79

Compound 79

The compound was synthesized using similar procedure as depicted in Example 2 by using compound 4f (as per the procedure given below) instead of H-Tyr(tBu)-OtBu. The crude solid material was purified using preparative HPLC described under experimental conditions. LCMS: 415.0 (M+H)+, HPLC: $t_R$=13.1 min.

Synthesis of Compound 4f:

Step 4a:

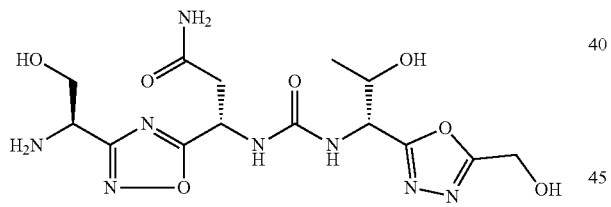

Methyl Iodide (4.9 g, 34 mmol) and potassium carbonate (6.0 g, 44 mmol) were added to the solution of compound 4a (7.1 g, 22 mmol) in DMF (70 mL) and stirred at room temperature for 3 h. The completeness of the reaction was confirmed by TLC analysis. The reaction mixture was partitioned between ice water and ethyl acetate. Organic layer was washed with brine solution, dried over $Na_2SO_4$ and evaporated under reduced pressure to yield 6.4 g of compound 4b. LCMS: 324.0 (M+H)+.

Step 4b:

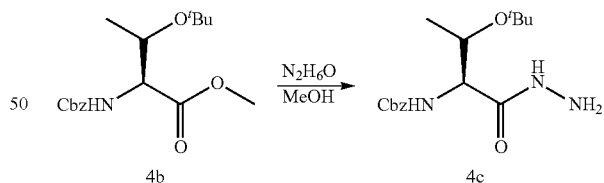

Hydrazine hydrate (6.4 mL) was added to the solution of compound 4b (6.4 g) in methanol (64 mL) and stirred at room temperature for 12 h. The completeness of the reaction was confirmed by TLC analysis. The reaction mixture was partitioned between ice water and ethyl acetate. Organic layer was washed with brine solution, dried over $Na_2SO_4$ and evaporated under reduced pressure to yield 5.5 g of compound 4c. LCMS: 324.2 (M+H)+].

Step 4c:

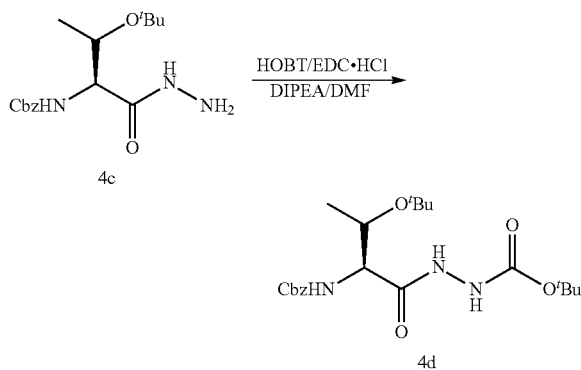

2-(tert-butoxy)acetic acid (1.16 g, 8.8 mmol), HOBT (1.3 g, 9.6 mmol), EDC.HCl (1.83 g, 9.6 mmol), DIPEA (2.5 g, 21 mmol) were added to the solution of compound 4c (2.6 g, 8.8 mmol) in DMF (50 mL) and stirred at room temperature for 4 h. The completeness of the reaction was confirmed by TLC analysis. The reaction mixture was partitioned between ice water and ethyl acetate. Organic layer was washed with $NaHCO_3$, Citric acid brine solution, dried over $Na_2SO_4$ and evaporated under reduced pressure to yield crude compound 6, which was further purified by silica gel column chromatography (eluent: 0-50% ethyl acetate in Hexane) to yield 3 g of product 4d. LCMS: 438.2 $(M+H)^+$.

Step 4d:

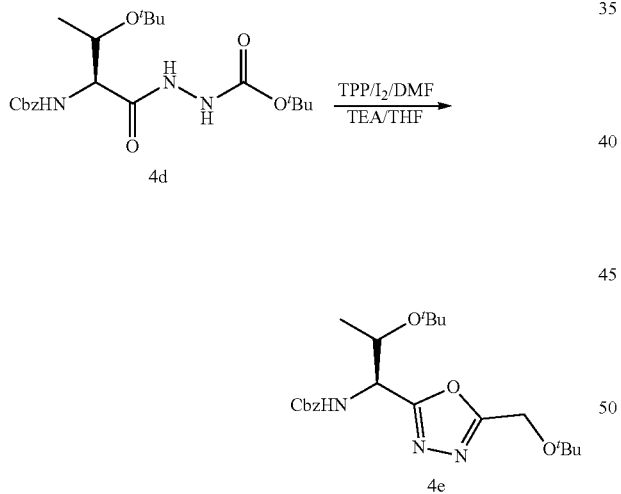

Triphenyl phosphine (6.5 g, 24 mmol), Iodine (6.2 g, 24 mmol), TEA (3.5 g, 35 mmol) were added to the solution of compound 4d (3.1 g, 7.0 mmol) in THF (50 mL) and DMF (10 mL) and stirred at room temperature for 3 h. The completeness of the reaction was confirmed by TLC analysis. The reaction mixture was partitioned between sodium thiosulfate solution and ethyl acetate. Organic layer was washed with brine solution, dried over $Na_2SO_4$ and evaporated under reduced pressure to yield crude compound 4e, which was further purified by silica gel column chromatography (eluent: 0-50% ethyl acetate in Hexane) to yield 2.4 g of product 4e. LCMS: 420.2 $(M+H)^+$.

Step 4e:

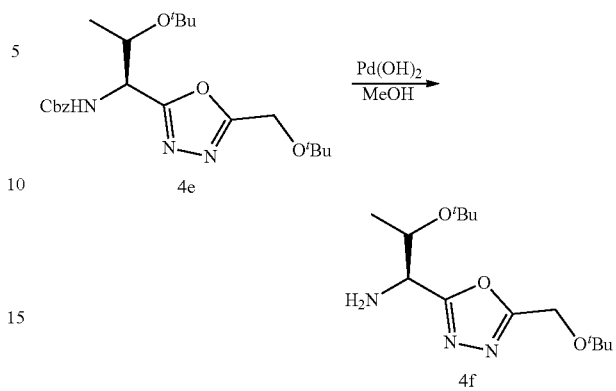

Palladium hydroxide (0.5 g) was added to the solution of compound 4e (2.3 g) in methanol (30 mL) and stirred under $H_2$ gas at room temperature for 2 h. The completeness of the reaction was confirmed by TLC analysis. The reaction mixture was filtered on celite bed and the filtrate evaporated under reduced pressure to yield 1.2 g of product 4f. LCMS: 286.1 $(M+H)^+$.

Step 4f:

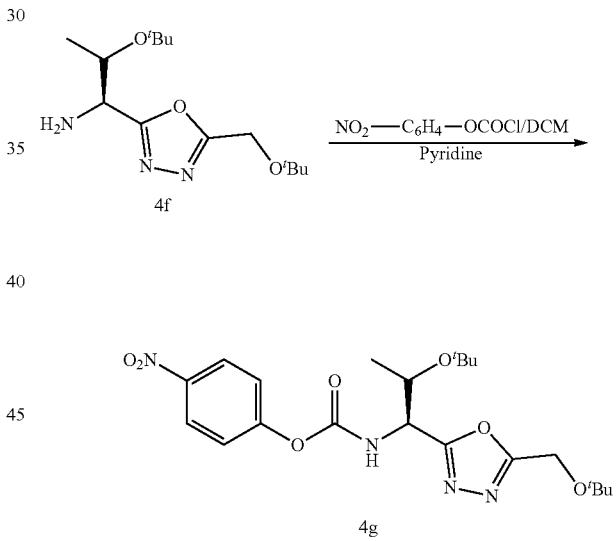

4-Nitro phenyl chloroformate (0.85 g, 4.2 mmol), Pyridine (0.36 g, 4.6 mmol) were added to the solution of compound 4f (1.2 g, 4.2 mmol) in $CH_2CL_2$ (40 mL) and stirred at room temperature for 1 h. The completeness of the reaction was confirmed by TLC analysis. The reaction mixture was partitioned between ice water and ethyl acetate. Organic layer was washed with Citric acid brine solution, dried over $Na_2SO_4$ and evaporated under reduced pressure to yield crude compound 4g, which was further purified by silica gel column chromatography (eluent: 0-40% ethyl acetate in Hexane) to yield 1.8 g of product 4 g.

Example 5: Synthesis of Compound 80

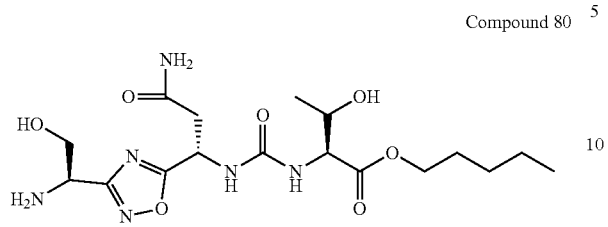

Compound 80

This compound was synthesized using similar procedure as depicted in Example 2 by using compound 5b (prepared as per the procedure given below) instead of H-Tyr(tBu)-OtBu. The crude solid material was purified using preparative HPLC described under experimental conditions. LCMS: 431.5 (M+H)$^+$, HPLC: $t_R$=12.6 min.

Synthesis of Compound 5b:

Step 5a:

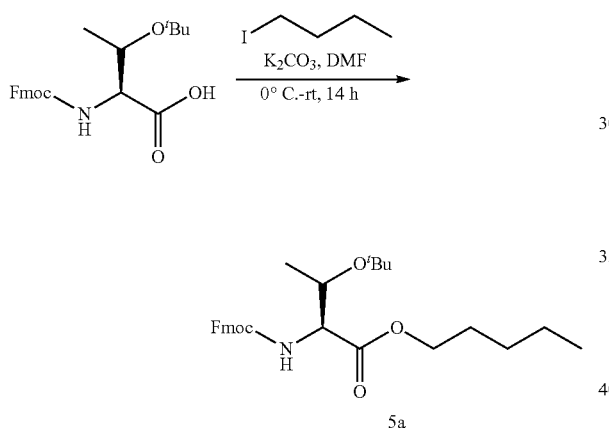

To a solution of Fmoc-Thr(tBu)-OH (5.5 g, 13.8 mmol) in DMF (25.0 mL) K$_2$CO$_3$ (2.9 g, 20.8 mmol) was added at 0° C. and stirred for 30 minutes followed by addition of iodopentane (2.1 mL, 16.6 mmol) at 0° C. The above reaction mixture was stirred at room temperature for 14 h. The completion of the reaction was confirmed by TLC analysis. The reaction mixture was partitioned between water and ethyl acetate. Organic layer was washed with NaHCO$_3$, brine solution, dried over Na$_2$SO$_4$ and evaporated under reduced pressure to yield compound 5a (6.86 g) and used for the next step without purification. LCMS: 246.4 (M-Fmoc+H)$^+$.

Step 5b:

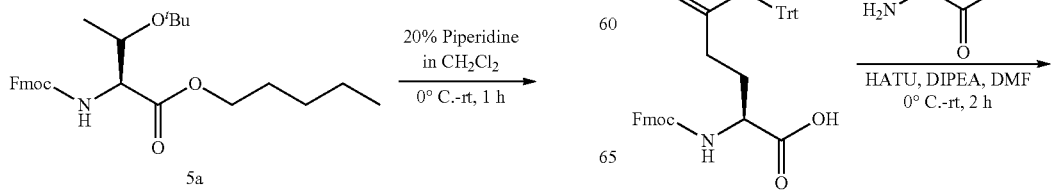

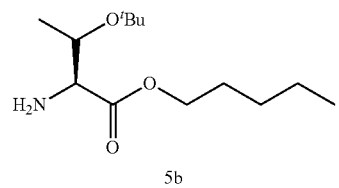

5b

To compound 5a (6.86 g, 14.67 mmol) 20% of piperidine in CH$_2$Cl$_2$ (34.3 mL) was added and the reaction mixture was stirred at room temperature for 1 h. The completeness of the reaction was confirmed by TLC analysis. The reaction mixture was evaporated under nitrogen and partitioned between water and ethyl acetate. Organic layer was washed with NaHCO$_3$, brine solution, dried over Na$_2$SO$_4$ and evaporated under reduced pressure. The crude compound 5b was purified by silica gel column chromatography (Eluent: 0-40% ethyl acetate in hexane to get 2.5 g of 5b. LCMS: 246.1 (M+H)$^+$.

Example 6: Synthesis of Compound 81

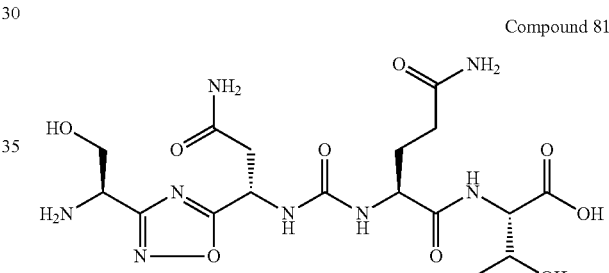

Compound 81

The compound was synthesized using similar procedure as depicted in Example 2 by using compound 6b (prepared as per the procedure given below) instead of H-Tyr(tBu)-OtBu. The crude solid material was purified using preparative HPLC described under experimental conditions. LCMS: 443.8 (M+H)$^+$, HPLC: $t_R$=8.8 min.

Synthesis of Compound 6b:

Step 6a:

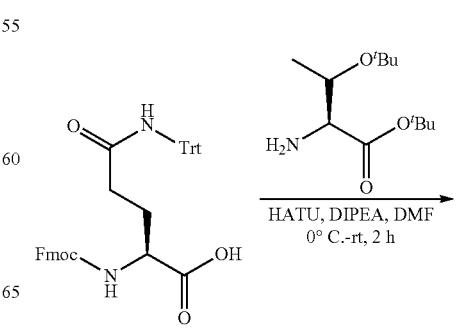

-continued

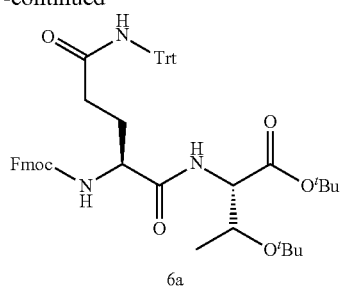

6a

To a solution of Fmoc-Gln(Trt)-OH (5.0 g, 8.2 mmol) in DMF (25.0 mL) HATU (3.4 g, 9.0 mmol), H-Thr(OtBu)-OtBu (1.9 g, 8.2 mmol) and DIPEA (2.9 mL, 16.4 mmol) were added at 0° C. and stirred at room temperature for 2 h. The completion of the reaction was confirmed by TLC analysis. The reaction mixture was quenched with water, the resulting solid was filtered, washed with hexane and dried to yield 7.4 g of compound 6a. LCMS: 824.1 (M+H)$^+$.

Step 6b

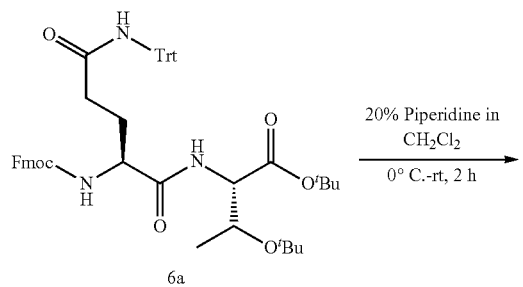

To compound 6a (7.4 g, 8.9 mmol) 20% of piperidine in CH$_2$Cl$_2$ (37.0 mL) was added, the reaction mixture was stirred at room temperature for 2 h. The completeness of the reaction was confirmed by TLC analysis. The reaction mixture was evaporated under nitrogen and partitioned between water and DCM. Organic layer was washed with NaHCO$_3$, brine solution, dried over Na$_2$SO$_4$ and evaporated under reduced pressure. The crude compound was washed with hexane and dried under reduced pressure to yield 3.7 g of compound 6b. LCMS: 601.8 (M+H)$^+$.

Example 7: Synthesis of Compound 82

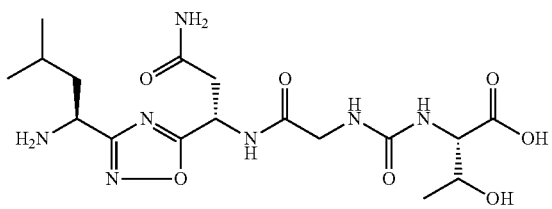

Compound 82

The compound was synthesized using similar procedure as depicted in Example 2 by using compound 7c (prepared as per the procedure given below) instead of compound 2d. The crude solid material was purified using preparative HPLC described under experimental conditions. LCMS: 443.8 (M+H)$^+$, HPLC: t$_R$=8.8 min.

Synthesis of Compound 7c:

Step 7a:

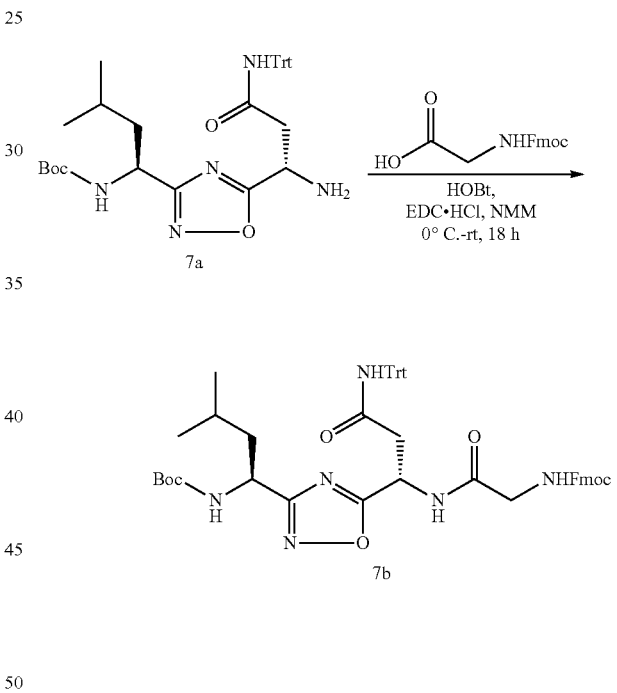

EDC.HCl (2.9 g, 14.97 mmol), HOBt (2.3 g, 14.97 mmol), Fmoc-Gly-OH (2.97 g, 9.98 mmol) and NMM (2.7 mL, 24.95 mmol) were added to a solution of compound 7a (5.83 g, 9.98 mmol, The compound 7a was synthesized using similar procedure as depicted for compound 2d in example-2) in DMF (30.0 mL) at 0° C. and stirred room temperature for 18 h. The reaction mixture was partitioned between water and ethyl acetate. Organic layer was washed with citric acid, NaHCO$_3$, brine solution, dried over Na$_2$SO$_4$ and evaporated under reduced pressure, which was further purified by silica gel column chromatography (Eluent: 10% ethyl acetate in hexane-100% ethyl acetate) to yield 6.0 g of compound 7b. LCMS: 885.4 (M+Na+H)$^+$.

Step 7b:

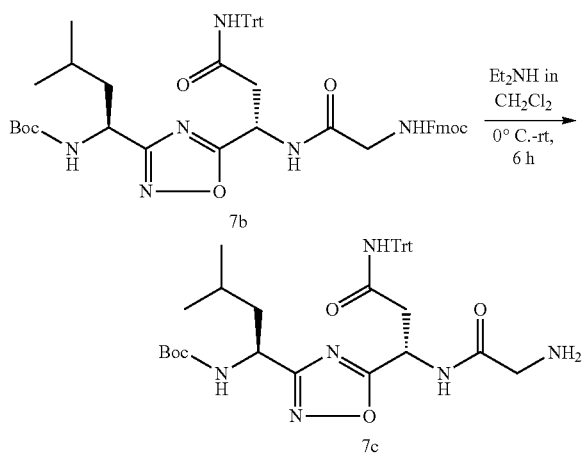

Diethyl amine (24.0 mL) was added to the solution of compound 7b (6.0 g, 6.95 mmol) in CH$_2$Cl$_2$ (24.0 mL). The reaction was stirred for 6 h at room temperature and the resulting solution was concentrated under nitrogen atmosphere to yield compound 7c which was purified by silica gel column chromatography (Eluent: 0-10% ethyl acetate in hexane then 2% methanol in DCM) to yield 4.5 g of compound 7c. LCMS: 641.2 (M+H)$^+$.

Example 8: Synthesis of Compound 83

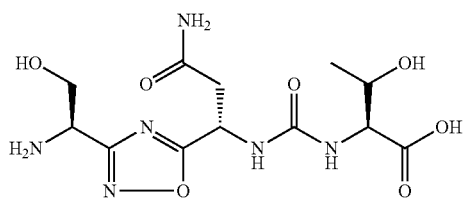

Compound 83

Step 8a:

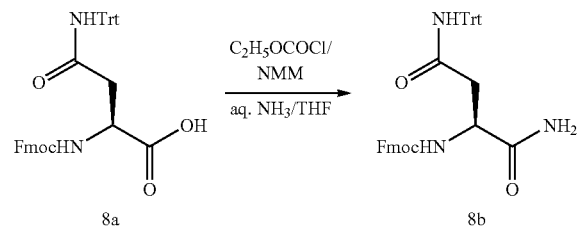

Ethylchloroformate (2.35 mL, 25.05 mmol) and N-Methylmorpholine (2.75 mL, 25.05 mmol) were added to a solution of compound 8a (5.0 g, 8.35 mmol) in THF (50 mL) and stirred at −20° C. After 20 min. aqueous ammonia (3.0 mL) was added to the active mixed anhydride formed in-situ and stirred at 0-5° C. for 1 h. The completeness of the reaction was confirmed by TLC analysis. The reaction mixture was poured into water and hexane, the resulting solid was filtered, washed with hexane and dried to get 4.2 g of compound 8b. LCMS: 596.3 (M+H)$^+$.

Step 8b:

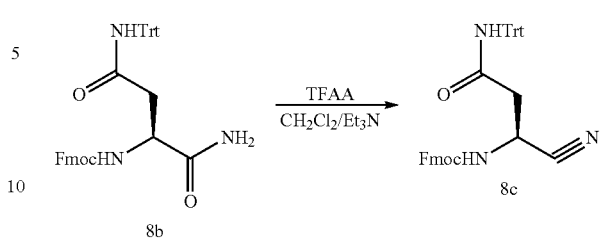

Triethyl amine (3.5 mL, 24.7 mmol) and Trifluoroacetic anhydride (1.5 mL, 10.6 mmol) were added to a solution of compound 8b (4.2 g, 7.1 mmol) in THF (70 mL) and stirred at 0° C. for 1 h. The completeness of the reaction was confirmed by TLC analysis. The reaction mixture was partitioned between water and ethyl acetate. Organic layer was washed with NaHCO$_3$, brine solution, dried over Na$_2$SO$_4$ and evaporated under reduced pressure to yield 4 g of crude compound 8c which was used for the next step without further purification. LCMS: 578.2 (M+H)$^+$, 600.2 (M+Na)$^+$.

Step 8c:

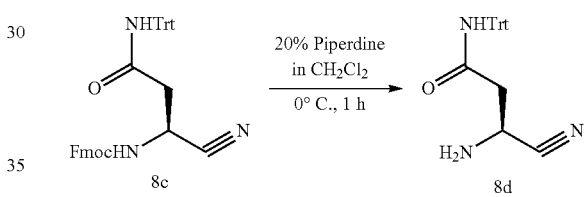

To compound 8c (1.5 g, 2.59 mmol) 20% of piperidine in CH$_2$Cl$_2$ (20.0 mL) was added and the reaction mixture was stirred at 0° C. for 1 h. The completeness of the reaction was confirmed by TLC analysis. The reaction mixture was evaporated under nitrogen and partitioned between water and ethyl acetate. Organic layer was washed with NaHCO$_3$, brine solution, dried over Na$_2$SO$_4$ and evaporated under reduced pressure. The crude compound was washed with hexane and 20% diethyl ether in hexane to yield 0.8 g of compound 8d which was used for the next step without further purification. LCMS: 378.4 (M+Na)$^+$.

Step 8d:

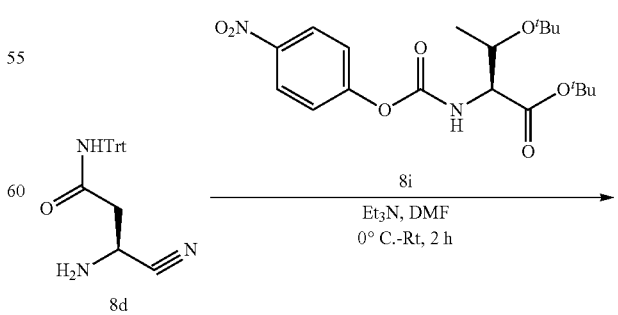

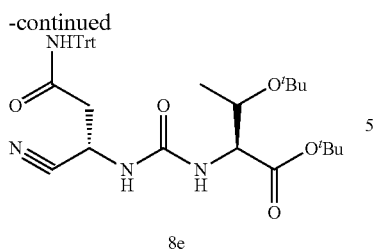

8e

Triethyl amine was added to a solution of compound 8d (0.8 g, 2.3 mmol) in DMF (15.0 mL) at 0° C. over a period of 2 minute. This was followed by the addition of compound 8i (1.0 g, 27.0 mmol). The reaction mixture was stirred at room temperature for 2 h. The completeness of the reaction was confirmed by TLC analysis. The reaction mixture was poured into water and the resulting solid was filtered, washed with hexane and 20% diethyl ether in hexane to yield 1.2 g of compound 8e. LCMS 613.6 (M+H)$^+$.

Step 8e:

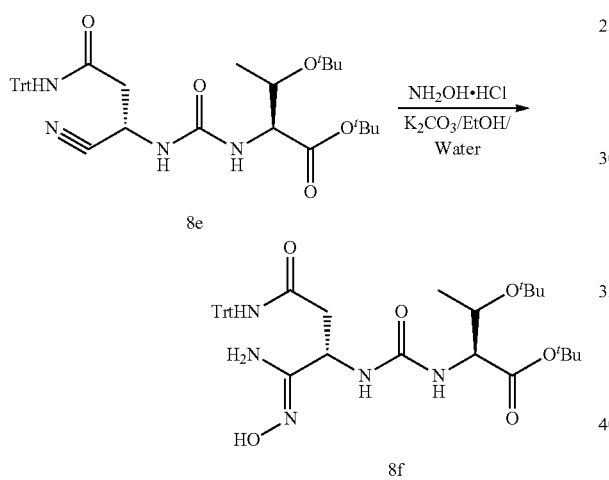

Hydroxylamine hydrochloride (0.204 g, 29.37 mmol), water (10.0 mL) and potassium carbonate (0.4 g, 29.37 mmol) were added to a solution of compound 8e (1.2 g, 19.58 mmol) in EtOH (26.0 mL) and stirred at 85° C. for 2 h. The completeness of the reaction was confirmed by TLC analysis. The reaction mixture was evaporated under reduced pressure and quenched with water, the resulting solid was filtered, washed with hexane and dried to yield 1.0 g of compound 8f. LCMS: 646.9 (M+H)$^+$.

Step 8f:

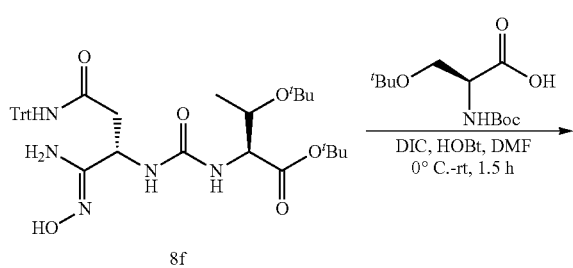

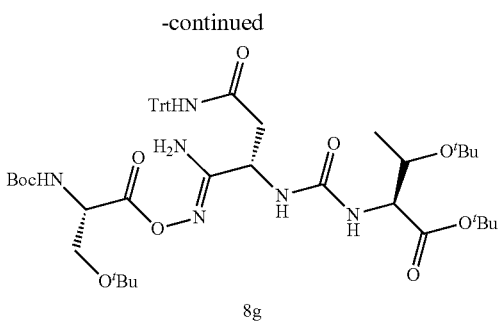

8g

DIC (0.29 mL, 18.58 mmol) and HOBt (0.25 g, 18.58 mmol) were added to a solution of Boc-Ser(tBu)-OH (0.4 g, 15.48 mmol) in DMF (20.0 mL) at 0° C. and stirred for 30 minutes followed by addition of compound 8f (1.0 g, 15.48 mmol) and stirred at room temperature for 1.5 h. The completeness of the reaction was confirmed by TLC analysis. The reaction mixture was quenched with water, the resulting solid was filtered, washed with diethyl ether, dried under reduced pressure to get 1.4 g of compound 8g, which used for the next step without further purification. LCMS: 889.4 (M+H)$^+$.

Step 8g:

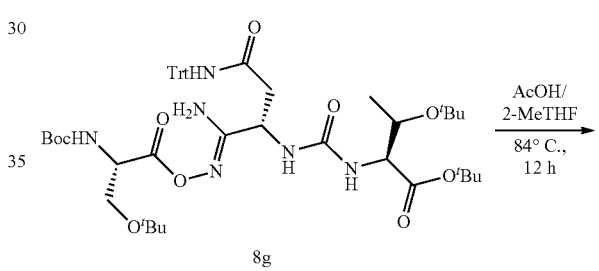

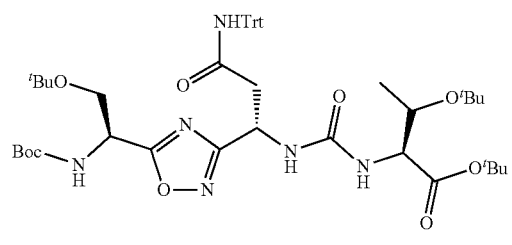

8h

Acetic acid (1.2 mL) was added to a solution of compound 8g (1.2 g, 13.49 mmol) in 2-methyl THF (30.0 mL). The reaction mixture was stirred at 84° C. for 12 h. The completeness of the reaction was confirmed by TLC analysis. The reaction mixture was partitioned between water and ethyl acetate. Organic layer was washed with NaHCO$_3$, brine solution, dried over Na$_2$SO$_4$ and evaporated under reduced pressure. The crude compound was washed with hexane and 5% diethyl ether in hexane to get 0.45 g of compound 8h which was used for the next step without further purification. LCMS: 871.4 (M+H)$^+$.

Step 8h:

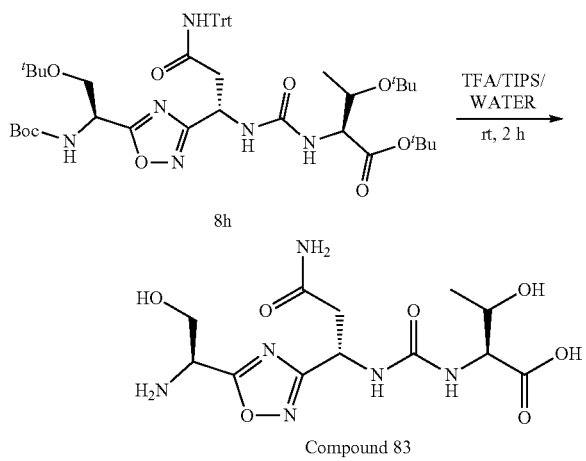

8h

Compound 83

To a solution of compound 8h (0.4 g, 4.55 mmol) in trifluoroacetic acid (9.5 mL), triisopropylsilane (0.25 mL) and water (0.25 mL) were added and stirred at room temperature for 2 h. The resulting solution was evaporated under nitrogen to obtain 0.1 g of crude compound 83. The crude solid material was purified using preparative-HPLC method described under experimental conditions. LCMS: 361.1 (M+H)$^+$; HPLC: $t_R$=13.9 min.

Synthesis of Compound 8i:

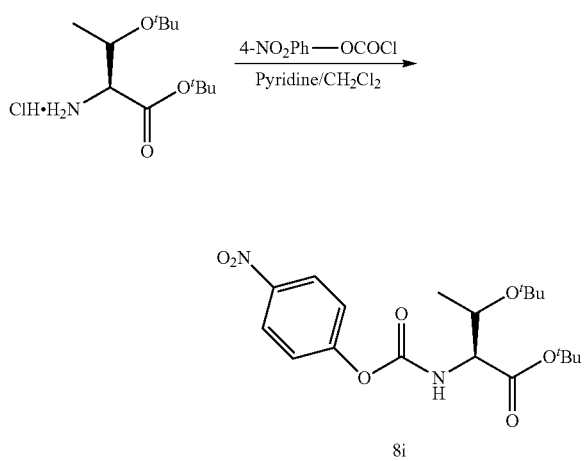

8i

To a solution of HCl.H-Thr($^t$Bu)-O$^t$Bu (8 g, 29.9 mmol) in CH$_2$Cl$_2$ (80 mL), was added pyridine (5.9 g, 74.0 mmol) and the solution was stirred for 5-10 min at room temperature. To this, a solution of 4-nitrophenyl chloroformate (7.2 g, 35.0 mmol) in CH$_2$Cl$_2$ was added and the resultant mixture was stirred for 30 min at room temperature. The completion of the reaction was confirmed by TLC analysis. After completion of reaction, the reaction mixture was diluted with CH$_2$Cl$_2$ and washed with water and 5.0 M citric acid solution. The separated organic layer was dried over Na$_2$SO$_4$, filtered and evaporated under reduced pressure to get crude compound, which was purified by silica gel column chromatography (eluent: 0-20% ethyl acetate in hexane) to yield 9 g of compound 8i. LCMS: 397.3 (M+H)$^+$.

Example 9: Synthesis of Compound 84

Compound 84

Step 9a:

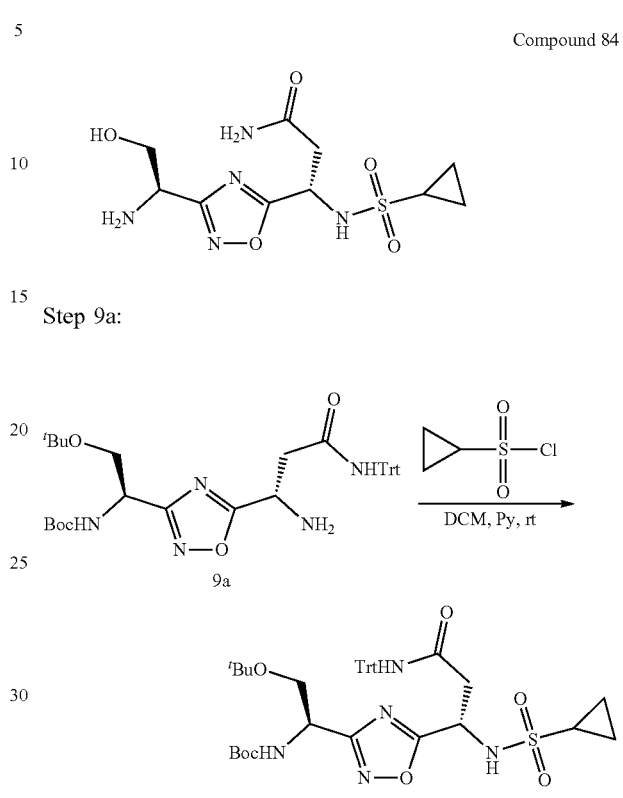

9a

9b

To a stirred solution of compound 9a (1.00 g) in DCM (40.0 mL) was added pyridine (0.33 mL) followed by cyclopropane sulfonyl chloride (0.33 mL) and the resultant mixture was stirred at ambient conditions for 16 h, when TLC-analysis has indicated the completion of the reaction. The reaction mixture was partitioned between water and DCM and the organic layer was washed with dil. HCl (1.0 N). The organic phase was then dried over Na$_2$SO$_4$ and was concentrated under reduced pressure to furnish the crude sulphonamide, which was further purified by column chromatography (neutral alumina, eluent Hexane-EtOAc (2:3)) to furnish the desired Compound 9b (1.10 g). LCMS: 735.4 (M+H+H$_2$O)$^+$.

Step 9b:

9b

-continued

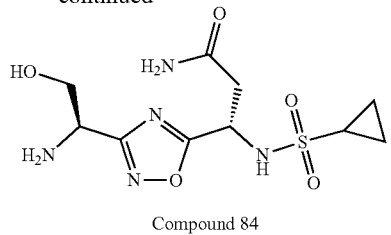

Compound 84

The compound 84 was prepared from compound 9b according to the procedure described in step 1g of Example-1 with appropriate variations in reactants, quantities of reagents, solvents and reaction conditions. LCMS $(M+H)^+$: 319.9

The below compounds were prepared by procedure similar to the one described in Example 9 (Compound 84) with appropriate variations in reactants or amino acids, solvents, quantities of reagents and reaction conditions. The analytical data of the compounds are summarized herein below table.

| Compound No. | Structure | LCMS $(M + H)^+$ |
|---|---|---|
| 85. | 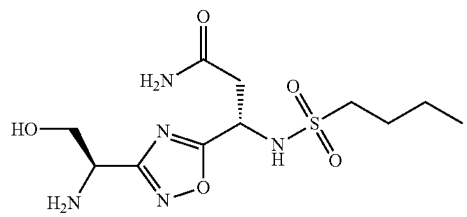 [SMILES: CCCCS(=O)(=O)N[C@@H](CC(N)=O)c1nc([C@@H](N)CO)no1] | 336.2 |
| 86. | 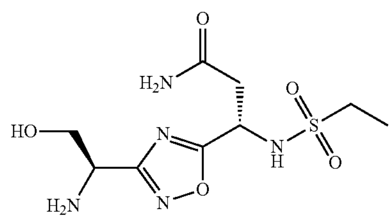 | 308.3 |
| 87. | 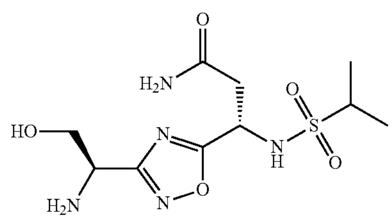 [SMILES: CC(C)S(=O)(=O)N[C@@H](CC(N)=O)c1nc([C@@H](N)CO)no1] | 322.3 |
| 88. | 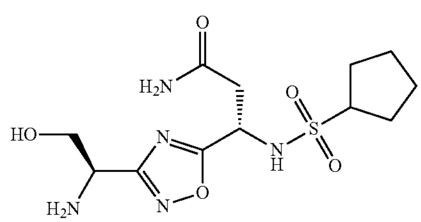 [SMILES: NC(=O)C[C@H](NS(=O)(=O)C1CCCC1)c1nc([C@@H](N)CO)no1] | 348.2 |
| 89. | 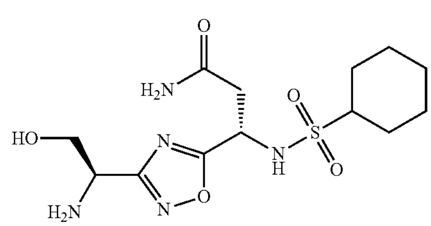 [SMILES: NC(=O)C[C@H](NS(=O)(=O)C1CCCCC1)c1nc([C@@H](N)CO)no1] | 362.3 |

| Compound No. | Structure | LCMS (M + H)+ |
|---|---|---|
| 90. | 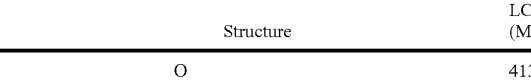 | 413.1 |

Example 10: Synthesis of Compound 91

Step 10a:

Step 10b:

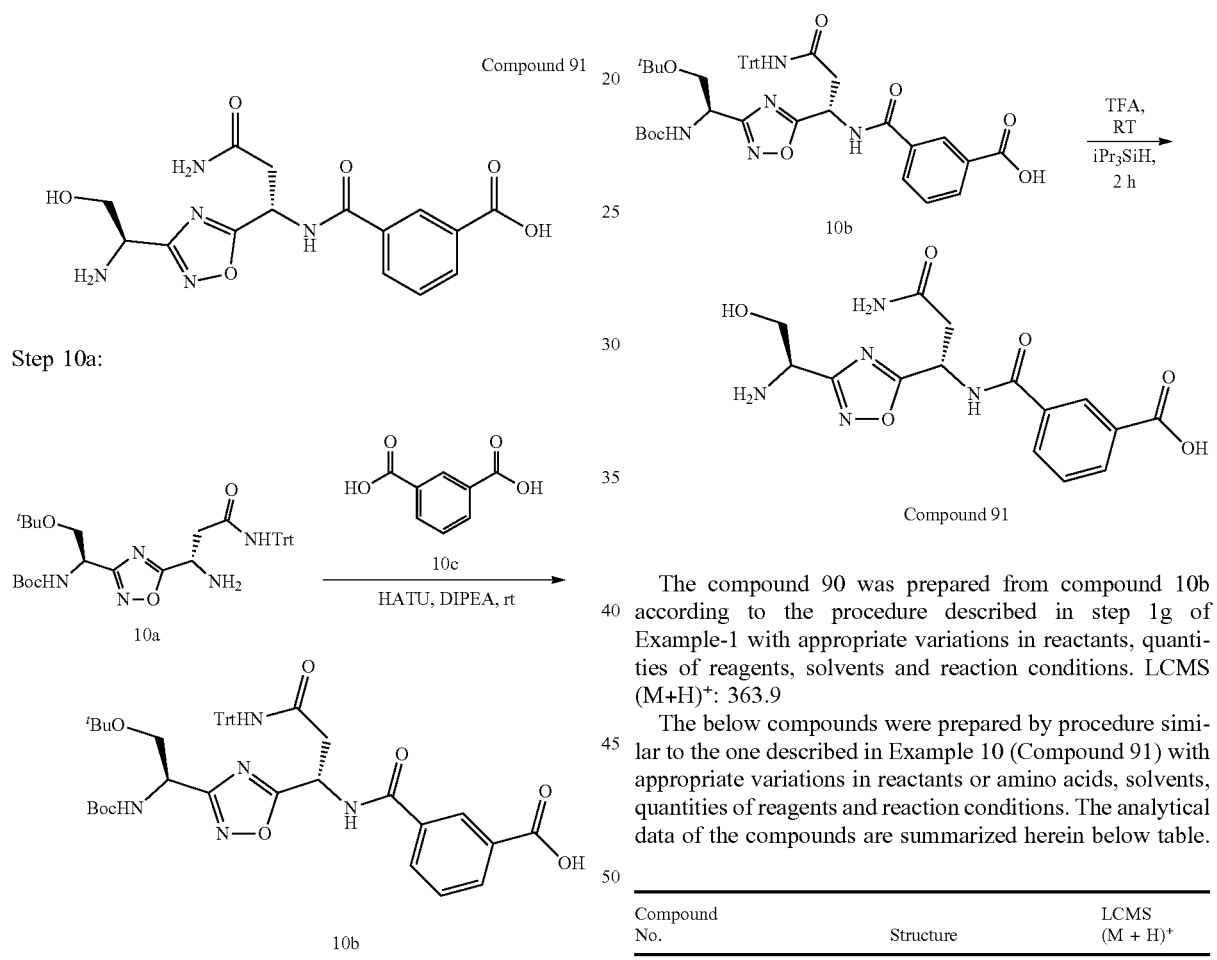

DIPEA (0.11 g, 0.89 mmol) was added under inert atmosphere to a stirred solution containing compound 10a (0.25 g, 0.4 mmol), carboxylic acid 10c (74 mg, 0.44 mmol) and HATU (0.23 g, 0.61 mmol) in dry DMF (3.0 mL). The reaction mixture was stirred at ambient conditions for 16 h and The resultant reaction mixture was partitioned between water (50 mL) and EtOAc (25 mL) and the aqueous layer was extracted with EtOAc (25 mL×3). Combined organic phases were washed once with cold water, dried over $Na_2SO_4$ and the solvent was removed under reduced pressure to furnish the compound 10b (0.12 g). LCMS: 779.0 $(M+H+H_2O)^+$.

The compound 90 was prepared from compound 10b according to the procedure described in step 1g of Example-1 with appropriate variations in reactants, quantities of reagents, solvents and reaction conditions. LCMS $(M+H)^+$: 363.9

The below compounds were prepared by procedure similar to the one described in Example 10 (Compound 91) with appropriate variations in reactants or amino acids, solvents, quantities of reagents and reaction conditions. The analytical data of the compounds are summarized herein below table.

| Compound No. | Structure | LCMS (M + H)+ |
|---|---|---|
| 92. | 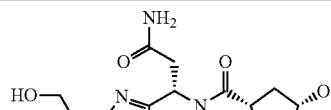 | 329.3 |
| 93. | 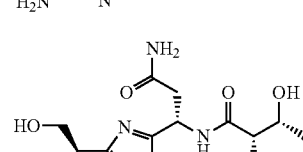 | 317.1 |

Example 11: Synthesis of Compound 94

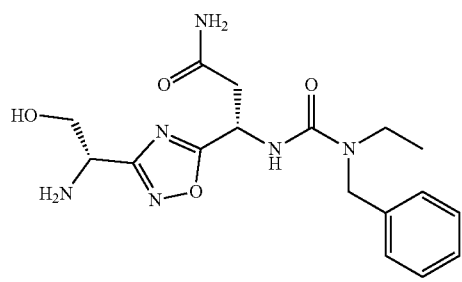

Compound 94

Step 11a:

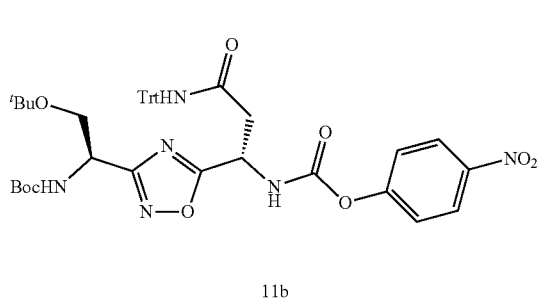

To a stirred solution of 11a (2.00 g) in DCM (40.0 mL) was added pyridine (0.53 mL) followed by 4-nitrophenyl chloroformate (0.65 g) and the resultant mixture was stirred at ambient conditions for 16 h. The reaction mixture was further partitioned between water and DCM and the organic layer was washed with dil. HCl (1.0 N). The organic phase was then dried over $Na_2SO_4$ and was concentrated under reduced pressure to furnish the crude sulphonamide, which was further purified by column chromatography (neutral alumina, eluent Hexane-EtOAc (2:3)) to furnish the desired carbamate 11b (2.66 g). LCMS: 801.4 $(M+H+Na)^+$.

Step 11b:

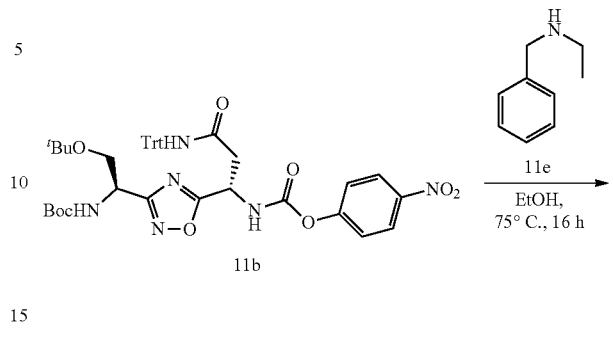

Amine 11e (0.55 g, 4.09 mmol) was added to a stirred solution of compound 11b (2.66 g, 3.41 mmol) in Ethanol (30.0 mL) and the resultant mixture was refluxed at 75° C. for 16 h. The completeness of the reaction was confirmed by TLC analysis. The reaction mixture was evaporated under reduced pressure, diluted with ethyl acetate (75 mL) and was sequentially washed with water (80 mL) followed by sat. $K_2CO_3$ solution (50 mL) and brine (50 mL). After drying the organics over $Na_2SO_4$, solvents were removed under reduced pressure to furnish the compound 11c (1.0 g). LCMS: 775.3 $(M+H)^+$.

Step 11c:

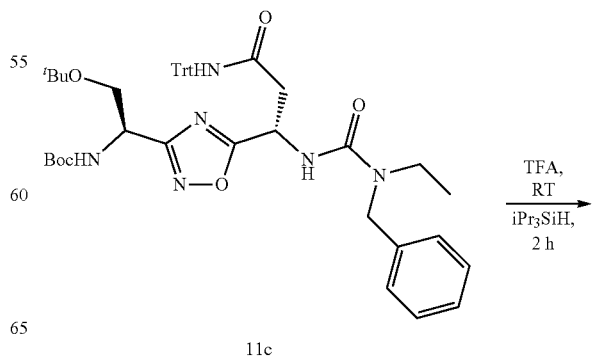

123

-continued

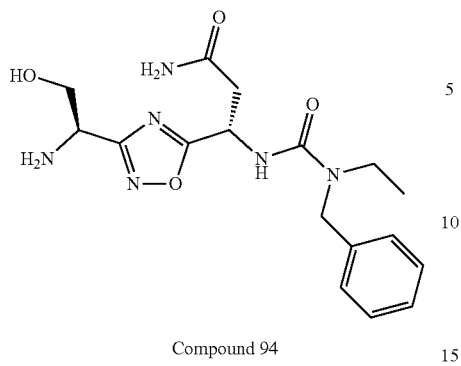

Compound 94

The compound 91 was prepared from compound 11c according to the procedure described in step 1g of Example-1 with appropriate variations in reactants, quantities of reagents, solvents and reaction conditions. LCMS (M+H)$^+$: 377.2

Example 12: Synthesis of Compound 95

Compound 95

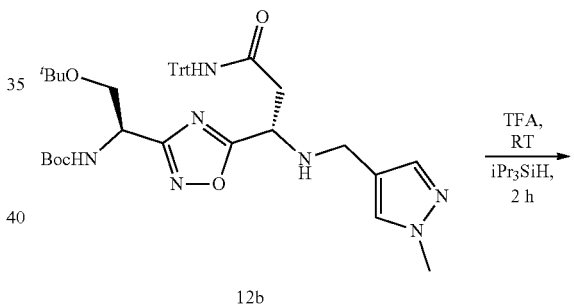

Step 12a:

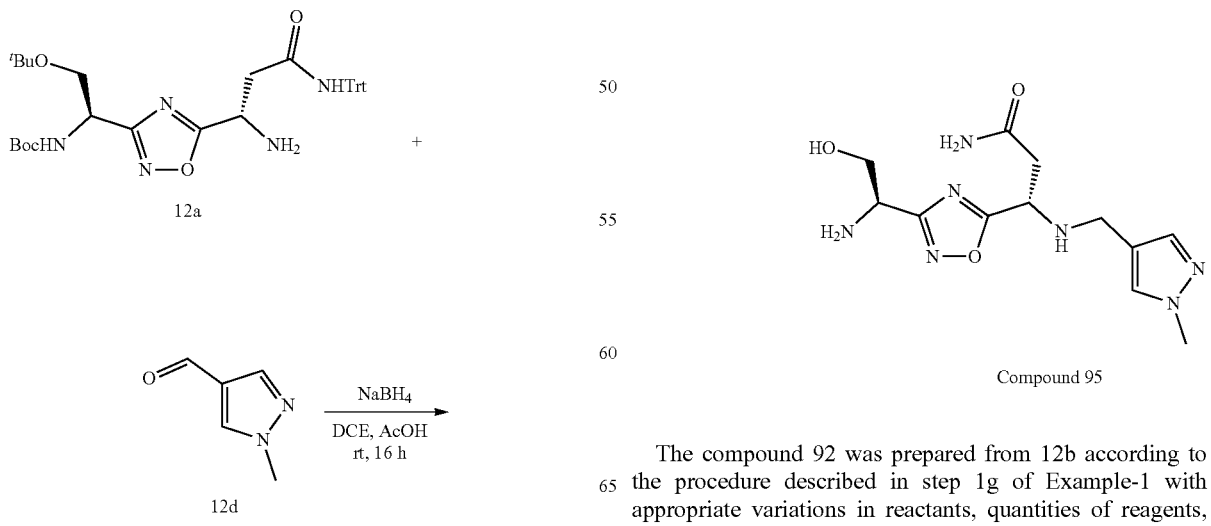

124

-continued

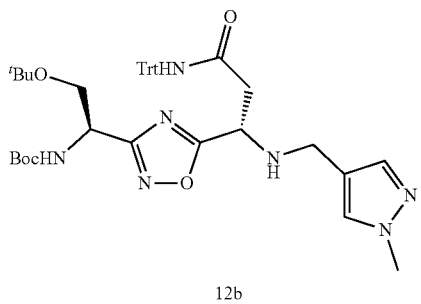

12b

Acetic acid (0.2 mL) was added to a stirred solution of compound 12a (500 mg) and compound 12d (134 mg) in dry DCE (20.0 mL) and the resultant mixture was stirred at RT for 12 h. Sodium borohydride (77.0 mg) was added to the above mixture and the resultant mixture was stirred at ambient temperature for 4 h. The reaction mixture was diluted with water (25 mL) and was extracted with DCM (3×25 mL). Combined organic phases were washed with brine and water, dried over Na$_2$SO$_4$ and the solvents were removed under reduced pressure to furnish the crude compound 12b, which was carried forward to the next step without further purification (200 mg). LCMS: 708.0 (M+H)$^+$.

Step 12b:

The compound 92 was prepared from 12b according to the procedure described in step 1g of Example-1 with appropriate variations in reactants, quantities of reagents, solvents and reaction conditions. LCMS (M+H)$^+$: 310.2

Example 13: Synthesis of Compound 96

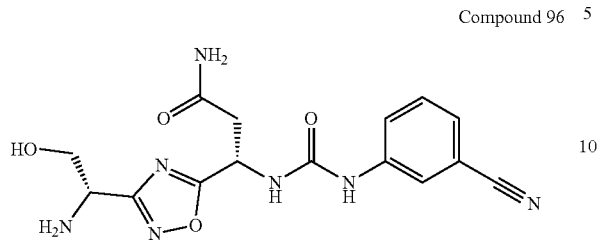

Compound 96

Step 13a:

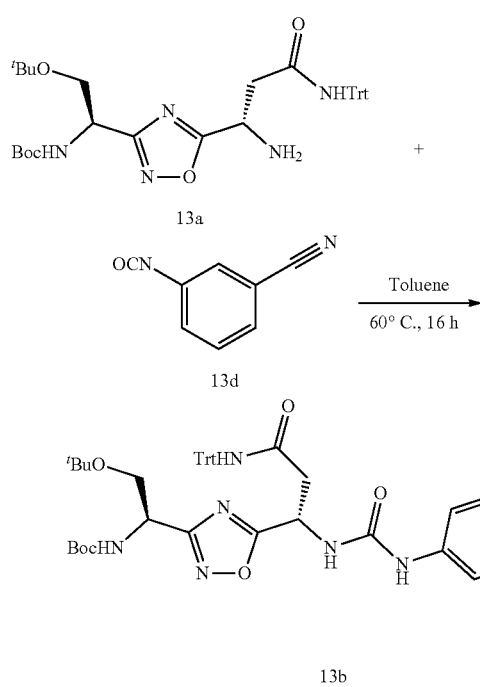

Compound 13d (77.0 mg) was added to a stirred solution of compound 13a (0.3 g) in Toluene (10.0 mL) under inert atmosphere and the resultant mixture was heated at 60° C. for 16 h., The solvent was removed under reduced pressure, the crude product was repeatedly washed with pentane (2×10 mL) and diethyl ether (2×10 mL) and was dried under reduced pressure to furnish compound 13b (200.0 mg). LCMS: 702.0 (M+H-$^t$Bu)$^+$.

Step 2:

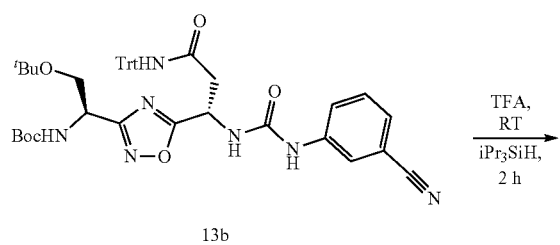

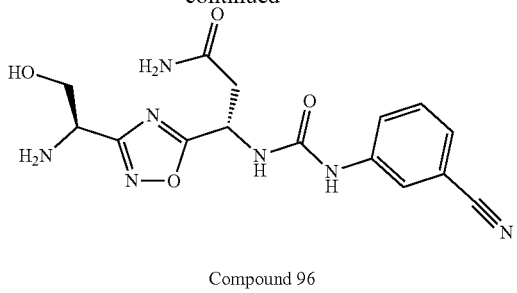

Compound 96

The compound 96 was prepared from 13b according to the procedure described in step 1g of Example-1 with appropriate variations in reactants, quantities of reagents, solvents and reaction conditions. LCMS (M+H)$^+$: 360.0

Example 14: Synthesis of Compound 97

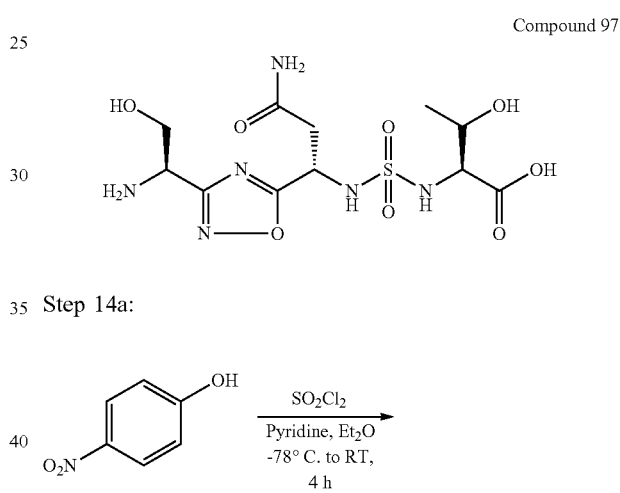

Compound 97

Step 14a:

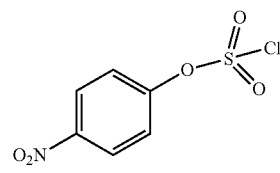

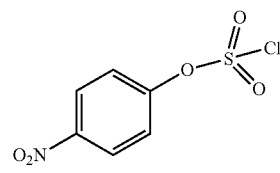

14a

A solution of 4-nitrophenol (1.3 g, 9.99 mmol) and pyridine (0.8 mL, 9.99 mmol) in Et$_2$O (20 mL) were added dropwise to a solution of SO$_2$Cl$_2$ (0.8 mL, 9.99 mmol) in Et$_2$O (20 mL) at −78° C. under argon. The reaction mixture allowed to warm to room temperature, stirred for 4 h. The completeness of the reaction was confirmed by TLC analysis. The volatiles were evaporated under reduced pressure to yield crude compound. The crude compound was purified by silica gel column chromatography (Eluent: 0-3% ethyl acetate in hexane) and resulted in 1.2 g of compound 14a. $^1$H NMR (400 MHz, CDCl$_3$): δ 8.39-8.36 (m, 2H), 7.61-7.57 (m, 2H).

Step 14b:

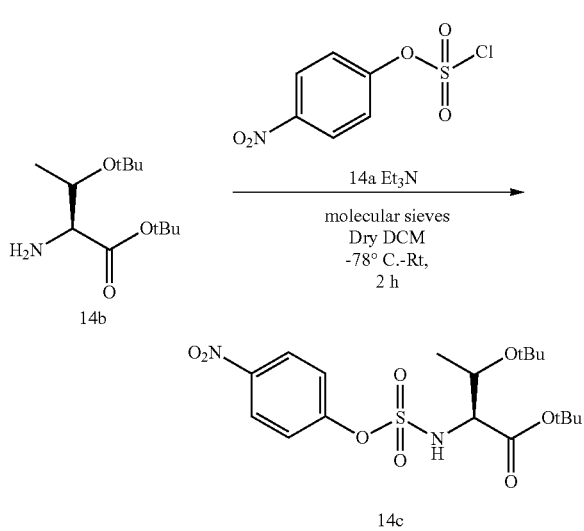

A mixture of compound 14b (0.6 g, 2.59 mmol), molecular sieves (1.0 g), 4-nitrophenol (0.72 g, 5.18 mmol) and Et₃N (1.1 mL, 7.77 mmol) in dry CH₂Cl₂ (25.0 mL), were added dropwise to a solution of compound 14a (1.2 g, 5.18 mmol) in dry CH₂Cl₂ (5.0 mL) at −78° C. under argon atmosphere. After stirring for 30 minutes. the reaction mixture allowed to warm to room temperature for 2 h. The completeness of the reaction was confirmed by TLC analysis. The reaction mixture was evaporated under reduced pressure to yield crude compound. The crude compound was purified by silica gel column chromatography (Eluent: 0-7% ethyl acetate in hexane) and resulted in 0.7 g of compound 14c. $^1$H NMR (300 MHz, CDCl₃): δ 8.30-8.27 (m 2H), 7.52-7.49 (m 2H), 5.70-5.67 (1H d, J 9.6), 4.17-3.90 (1H, m), 1.49 (9H, s), 1.28-1.23 (3H, m), 1.15 (9H, s).

Step 14c:

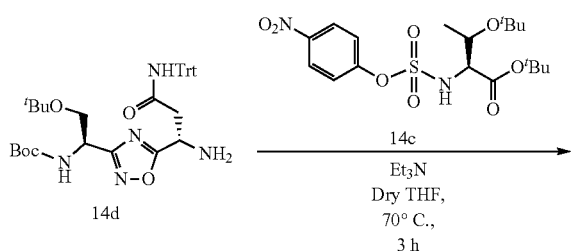

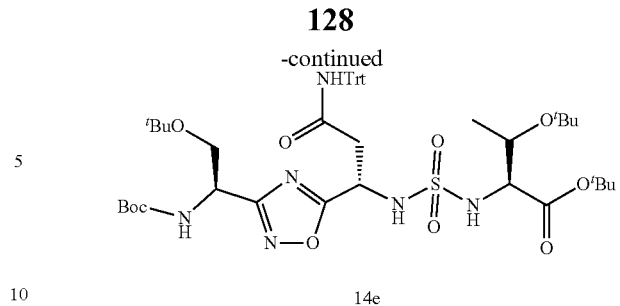

Compound 14c (0.69 g, 1.59 mmol) in THF (5.0 mL) was added to a stirred solution of compound 14d (0.7 g, 1.14 mmol) and Et₃N (0.5 mL, 3.42 mmol) in dry THF (10.0 mL) and the resulting reaction mixture was stirred at 70° C. for 3 h. The completeness of the reaction was confirmed by TLC analysis. The volatiles were evaporated under reduced pressure to yield crude compound. The crude compound was purified by silica gel column chromatography (Eluent: 0-33% ethyl acetate in hexane) and resulted in 0.55 g of compound 14e. LCMS: 907.4 (M+H)⁺.

Step 14d:

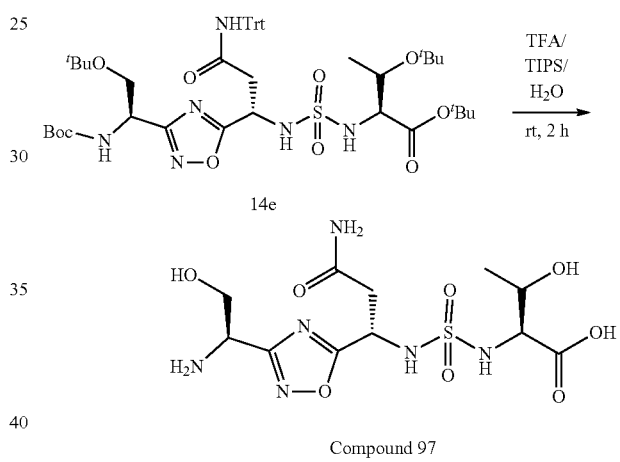

To a solution of compound 14e (0.55 g, 0.55 mmol) in trifluoroacetic acid (9.5 mL), triisopropylsilane (0.25 mL) and water (0.25 mL) were added and stirred at room temperature for 2 h. The resulting solution was evaporated under nitrogen to obtain 0.3 g of crude compound 97. The crude solid material was purified using preparative-HPLC method described under experimental conditions. LCMS: 397.0 (M+H)⁺; HPLC: $t_R$=10.547 min.

The below compounds were prepared by procedure similar to the one described in Example 14 (compound 97) with appropriate variations in reactants or amino acids, solvents, quantities of reagents and reaction conditions. The analytical data of the compounds are summarized herein below table.

| Compound No. | Structure | LCMS (M + H)⁺ | HPLC ($t_R$, min) |
|---|---|---|---|
| 98 | 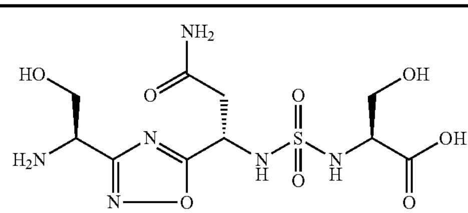 | 403.1 | 14.7 |

-continued

| Compound No. | Structure | LCMS (M + H)+ | HPLC (t_R, min) |
|---|---|---|---|
| 99 | 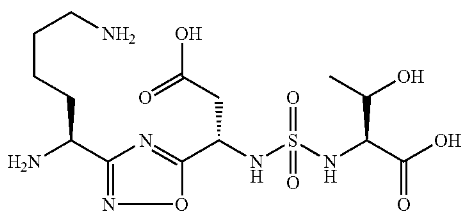 [SMILES: CC(O)[C@H](NS(=O)(=O)N[C@@H](CC(=O)O)c1nc([C@@H](N)CCCCN)no1)C(=O)O] | 439.1 | 16.9 |
| 100 | 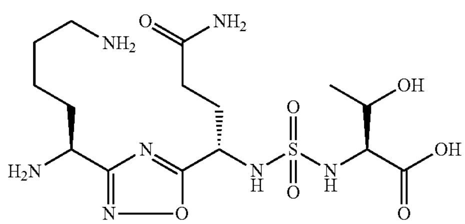 [SMILES: CC(O)[C@H](NS(=O)(=O)N[C@@H](CCC(N)=O)c1nc([C@@H](N)CCCCN)no1)C(=O)O] | 452.4 | 8.9 |
| 101 | 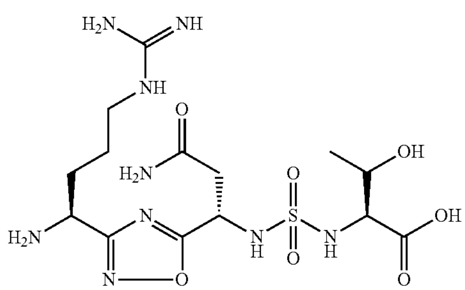 [SMILES: CC(O)[C@H](NS(=O)(=O)N[C@@H](CC(N)=O)c1nc([C@@H](N)CCCNC(=N)N)no1)C(=O)O] | 452.0 | — |
| 102 | 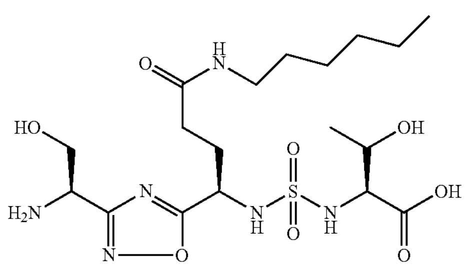 [SMILES: CCCCCCNC(=O)CC[C@@H](NS(=O)(=O)N[C@H](C(=O)O)C(C)O)c1nc([C@@H](N)CO)no1] | 493.4 | — |
| 103 | 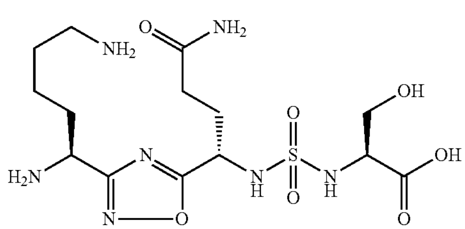 [SMILES: NCCCC[C@H](N)c1noc([C@H](CCC(N)=O)NS(=O)(=O)N[C@@H](CO)C(=O)O)n1] | 438.7 | — |
| 104 | 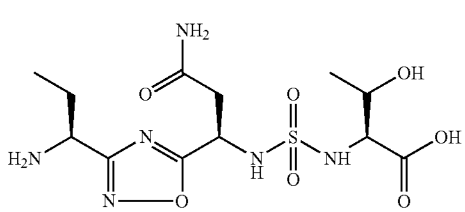 [SMILES: CC[C@H](N)c1noc([C@@H](CC(N)=O)NS(=O)(=O)N[C@H](C(=O)O)C(C)O)n1] | 395.2 | 10.2 |

Although the present application has been illustrated by certain of the preceding examples, it is not to be construed as being limited thereby; but rather, the present application encompasses the generic area as herein before disclosed. Various modifications and embodiments can be made without departing from the spirit and scope thereof. For example, the following compounds which can be prepared by following similar procedure as described above with suitable modification known to the one ordinary skilled in the art are also included in the scope of the present application:

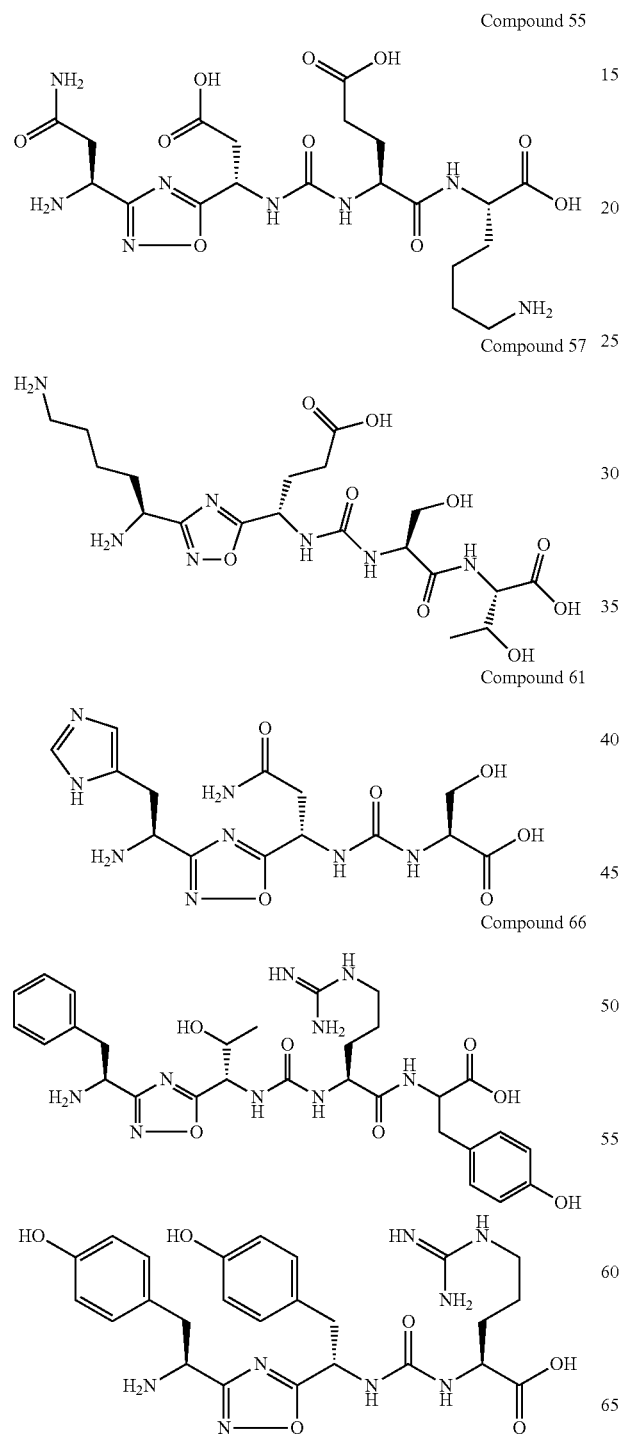

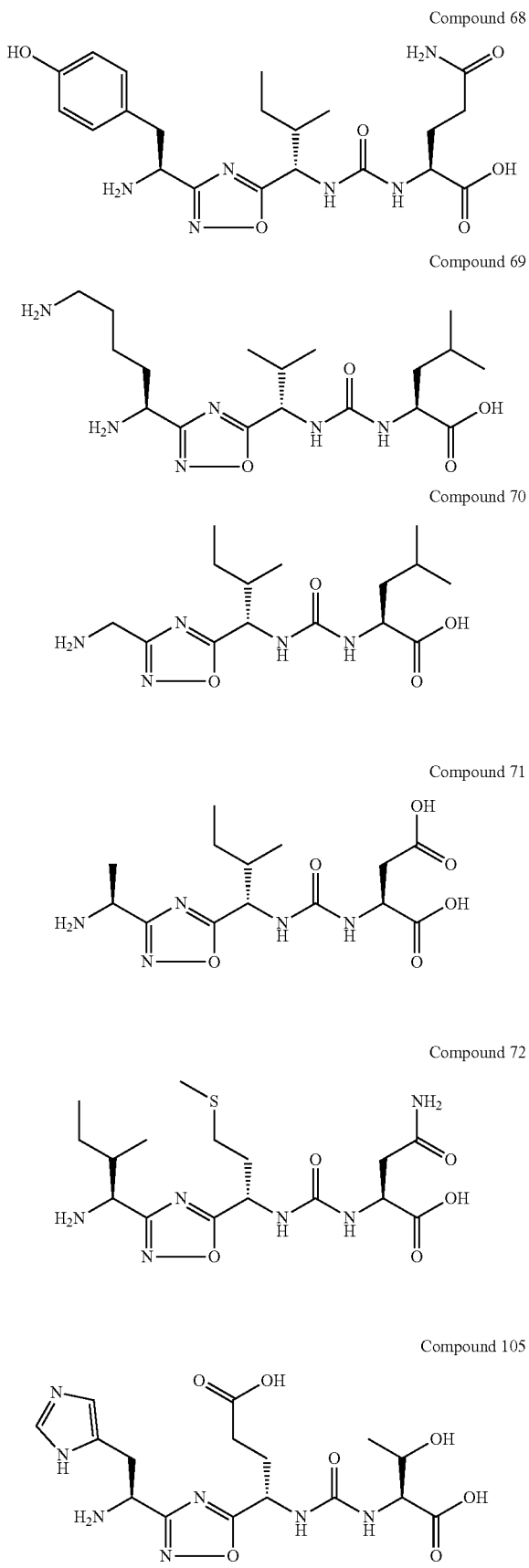

Compound 106
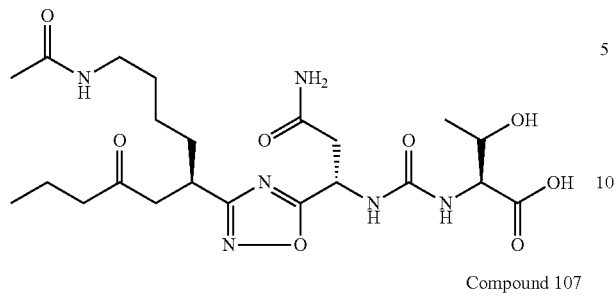
Compound 107
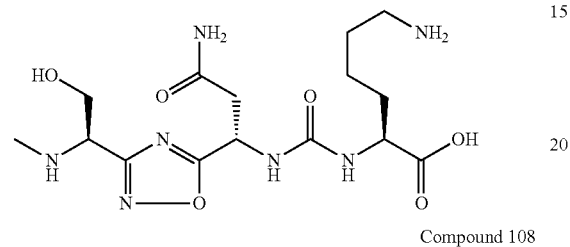
Compound 108
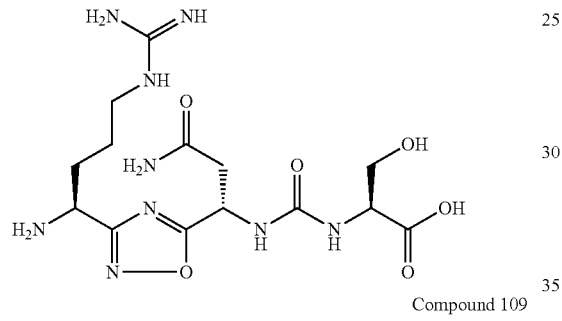
Compound 109
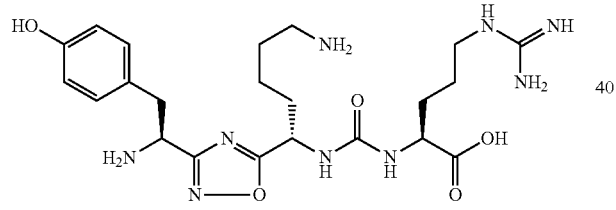
Compound 110
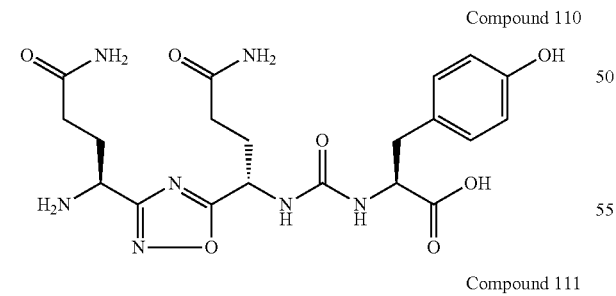
Compound 111
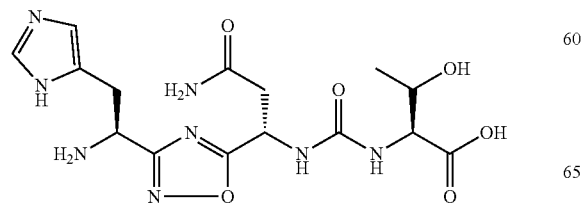
Compound 112
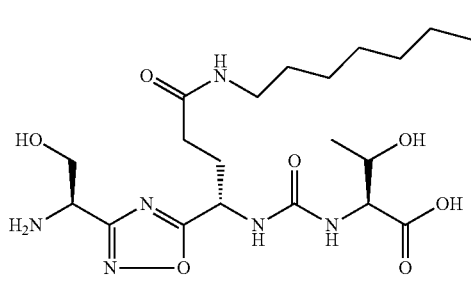
Compound 113
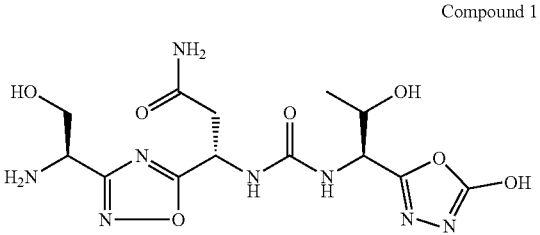
Compound 114
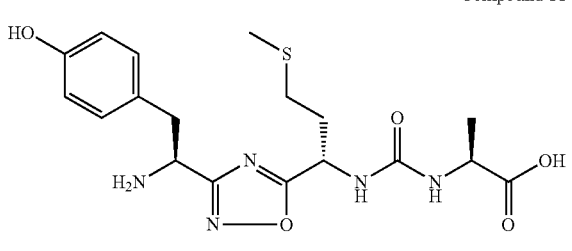
Compound 115
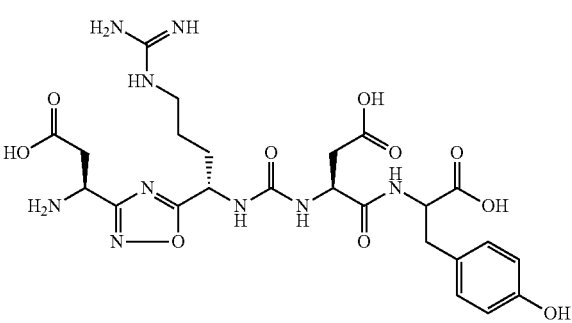
Compound 116
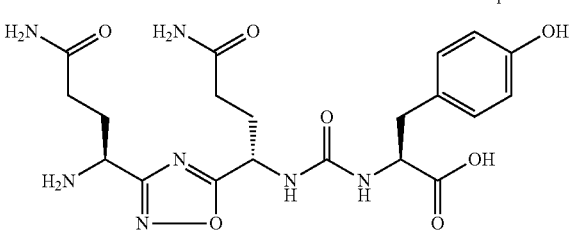
Compound 117
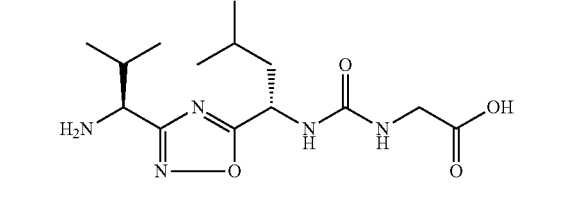

Compound 118

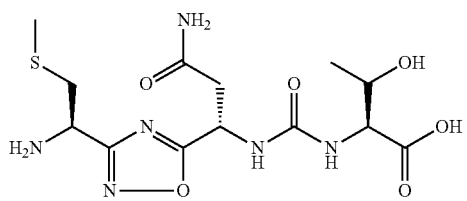

Compound 119

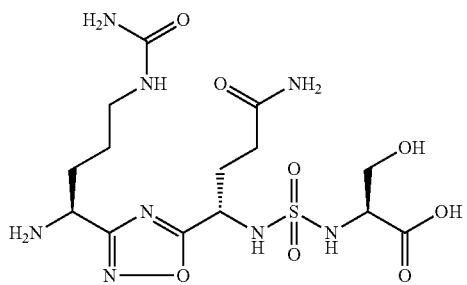

Compound 120

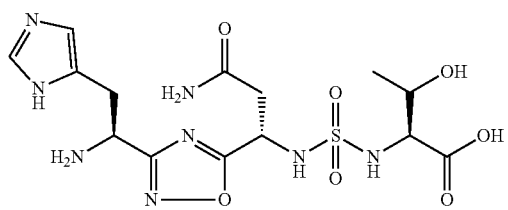

Compound 121

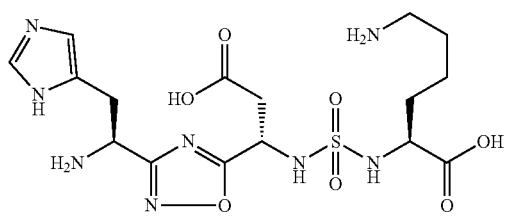

Compound 122

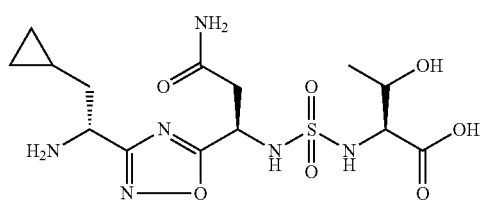

Compound 123

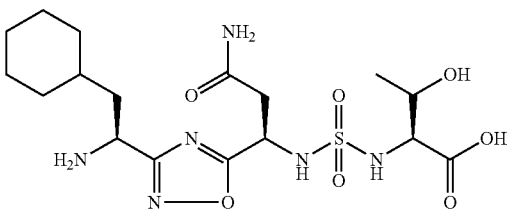

Compound 124

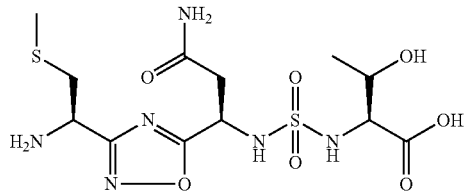

Example 15: Rescue of Mouse Splenocyte Proliferation in the Presence of Recombinant PD-L1

Recombinant mouse PD-L1 (rm-PDL-1, cat no: 1019-B7-100; R&D Systems) were used as the source of PD-L1.

Requirement:

Mouse splenocytes harvested from 6-8 weeks old C57 BL6 mice; RPMI 1640 (GIBCO, Cat #11875); DMEM with high glucose (GIBCO, Cat #D6429); Fetal Bovine Serum [Hyclone, Cat #SH30071.03]; Penicillin (10000 unit/mL)-Streptomycin (10,000 µg/mL) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #-A10492); Histopaque (density-1.083 gm/mL) (SIGMA 10831); Trypan blue solution (SIGMA-T8154); 2 mL Norm Ject Luer Lock syringe—(Sigma 2014-12); 40 µm nylon cell strainer (BD FALCON 35230); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 µL of Dimethyl sulfoxide (DMSO $C_2H_6SO$, SIGMA-D-5879) and aliquoted in to tubes for further use. Working concentrations were titrated from 10 µM to 1 µM. (eBioscience-650850-85); 0.05% Trypsin and 0.02% EDTA (SIGMA 59417C); 96-well format ELISA plates (Corning CLS3390); BD FACS caliber (E6016); Recombinant mouse B7-H1/PDL1 Fc Chimera, (rm-PD-L1 cat no: 1019-B7-100).

Protocol

Splenocyte Preparation and Culturing:

Splenocytes harvested in a 50 mL falcon tube by mashing mouse spleen in a 40 µm cell strainer were further treated with 1 mL ACK lysis buffer for 5 min at room temperature. After washing with 9 mL of RPMI complete media, cells were re-suspended in 3 mL of 1×PBS in a 15 mL tube. 3 mL of Histopaque was added carefully to the bottom of the tube without disturbing overlaying splenocyte suspension. After centrifuging at 800×g for 20 min at room temperature, the opaque layer of splenocytes was collected carefully without disturbing/mixing the layers. Splenocytes were washed twice with cold 1×PBS followed by total cell counting using Trypan Blue exclusion method and used further for cell based assays.

Splenocytes were cultured in RPMI complete media (RPMI+10% fetal bovine serum+1 mM sodium pyruvate+10,000 units/mL penicillin and 10,000 µg/mL streptomycin) and maintained in a $CO_2$ incubator with 5% $CO_2$ at 37° C.

CFSE Proliferation Assay:

CFSE is a dye that passively diffuses into cells and binds to intracellular proteins. $1\times10^6$ cells/mL of harvested splenocytes were treated with 5 µM of CFSE in pre-warmed 1×PBS/0.1% BSA solution for 10 min at 37° C. Excess CFSE was quenched using 5 volumes of ice-cold culture media to the cells and incubated on ice for 5 min. CFSE labelled splenocytes were further given three washes with ice cold complete RPMI media. CFSE labelled $1\times10^5$ splenocytes added to wells containing either MDA-MB231 cells ($1\times10^5$ cells cultured in high glucose DMEM medium) or recombinant human PDL-1 (100 ng/mL) and test compounds. Splenocytes were stimulated with anti-mouse CD3 and anti-mouse CD28 antibody (1 µg/mL each) and the culture was further incubated for 72 h at 37° C. with 5% $CO_2$. Cells were harvested and washed thrice with ice cold FACS buffer and % proliferation was analysed by flow cytometry with 488 nm excitation and 521 nm emission filters.

Data Compilation, Processing and Inference:

Percent splenocyte proliferation was analysed using cell quest FACS program and percent rescue of splenocyte proliferation by compound was estimated after deduction of % background proliferation value and normalising to % stimulated splenocyte proliferation (positive control) as 100%. The results are given in Table I.

Stimulated splenocytes: Splenocytes+anti-CD3/CD28 stimulation

Background proliferation: Splenocytes+anti-CD3/CD28+PD-L1

Compound proliferation: Splenocytes+anti-CD3/CD28+PD-L1+Compound

Compound effect is examined by adding required conc. of compound to anti-CD3/CD28 stimulated splenocytes in presence of ligand (PDL-1).

TABLE I

Percent rescue of splenocyte proliferation data of compounds of invention

| Compound No. | Percent rescue of splenocyte proliferation (@100 nM) |
|---|---|
| 1 | 76 |
| 2 | 68 |
| 3 | 73 |
| 4 | 44 |
| 5 | 38 |
| 6 | 69 |
| 7 | 91 |
| 8 | 48 |
| 9 | 84 |
| 10 | 84 |
| 11 | 66 |
| 13 | 62 |
| 14 | 92 |
| 15 | 28 |
| 16 | 50 |
| 17 | 58 |
| 18 | 57 |
| 19 | 54 |
| 20 | 51 |
| 21 | 51 |
| 23 | 49 |
| 24 | 17 |
| 27 | 37 |
| 28 | 36 |
| 30 | 65 |
| 31 | 42 |
| 32 | 70 |
| 33 | 60 |

TABLE I-continued

Percent rescue of splenocyte proliferation data of compounds of invention

| Compound No. | Percent rescue of splenocyte proliferation (@100 nM) |
|---|---|
| 34 | 59 |
| 35 | 66 |
| 36 | 68 |
| 37 | 60 |
| 38 | 52 |
| 39 | 75 |
| 40 | 67 |
| 41 | 78 |
| 42 | 50 |
| 43 | 60 |
| 44 | 71 |
| 45 | 17 |
| 46 | 53 |
| 47 | 49 |
| 51 | 20 |
| 52 | 71 |
| 56 | 26 |
| 60 | 99 |
| 62 | 35 |
| 75 | 119 |
| 76 | 67 |
| 77 | 75 |
| 78 | 42 |
| 79 | 37 |
| 80 | 55 |
| 81 | 18 |
| 82 | 12 |
| 83 | 34 |
| 84 | 71 |
| 88 | 10 |
| 89 | 54 |
| 90 | 66 |
| 94 | 97 |
| 95 | 30 |
| 101 | 70 |
| 102 | 38 |
| 103 | 79 |

We claim:

1. A method of treating cancer in a subject in need thereof, comprising administering to the subject a compound selected from:

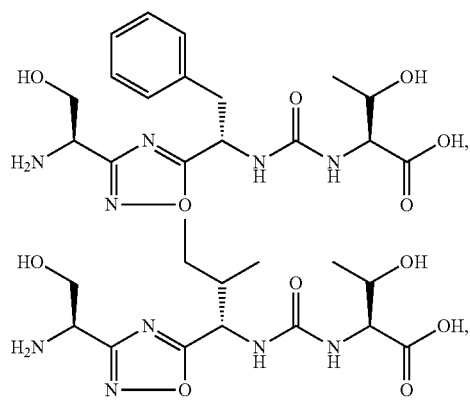

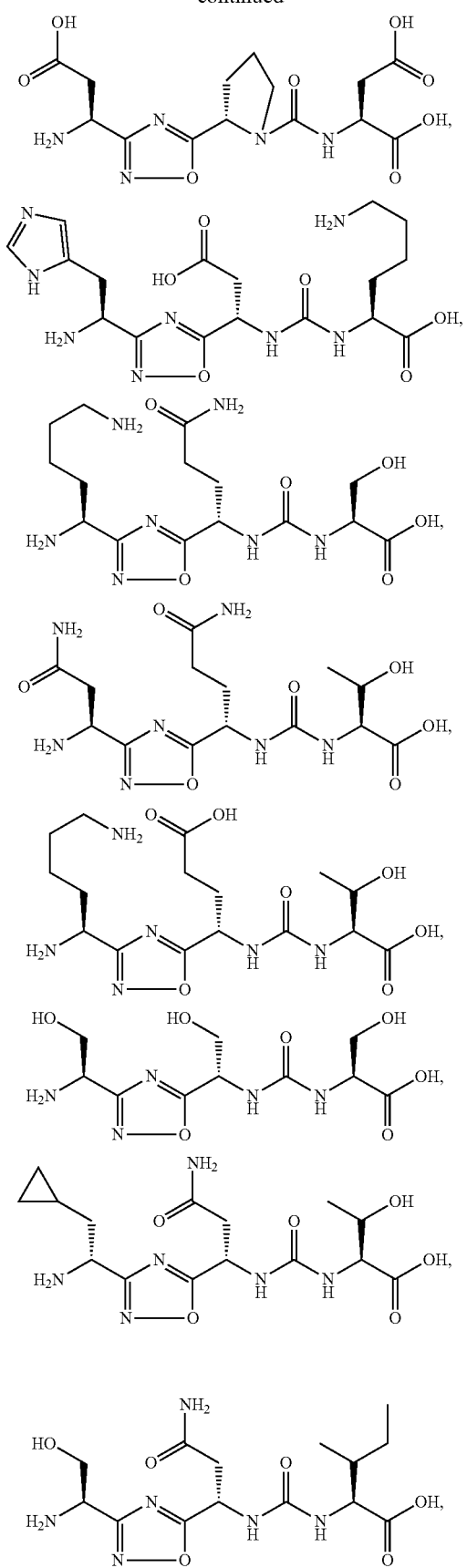
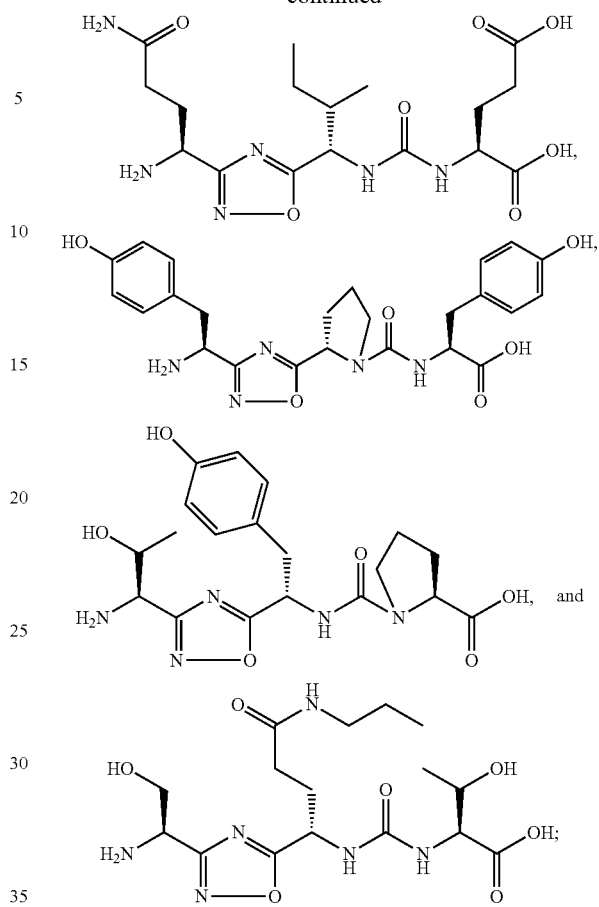
or a pharmaceutically acceptable salt thereof.
2. The method of claim 1, wherein the compound is
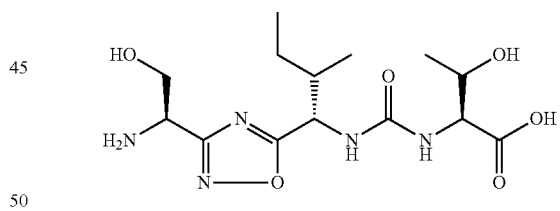
or a pharmaceutically acceptable salt thereof.
3. The method of claim 1, wherein the compound is
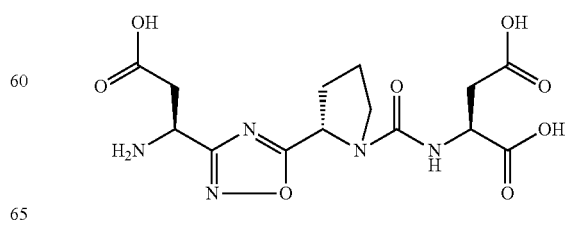
or a pharmaceutically acceptable salt thereof.

4. The method of claim 1, wherein the compound is

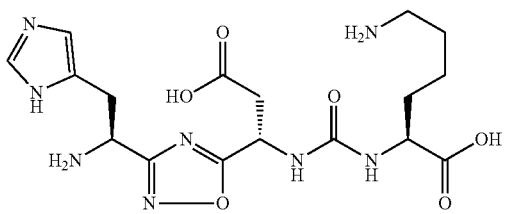 [SMILES: NCCCC[C@H](NC(=O)N[C@@H](CC(=O)O)c1nc([C@@H](N)Cc2cnc[nH]2)no1)C(=O)O]

or a pharmaceutically acceptable salt thereof.

5. The method of claim 1, wherein the compound is

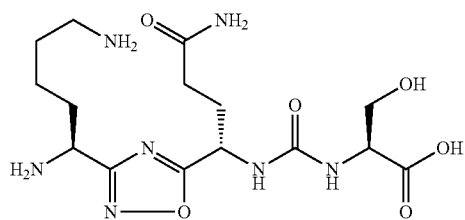

or a pharmaceutically acceptable salt thereof.

6. The method of claim 1, wherein the compound is

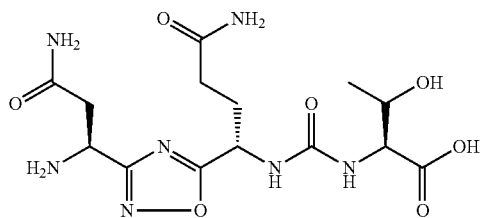 [SMILES: CC(O)[C@H](NC(=O)N[C@@H](CCC(N)=O)c1nc([C@@H](N)CC(N)=O)no1)C(=O)O]

or a pharmaceutically acceptable salt thereof.

7. The method of claim 1, wherein the compound is

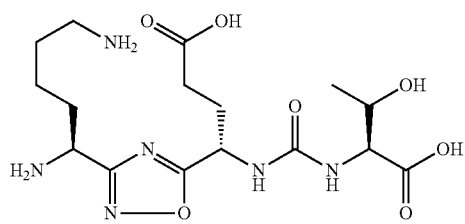

or a pharmaceutically acceptable salt thereof.

8. The method of claim 1, wherein the compound is

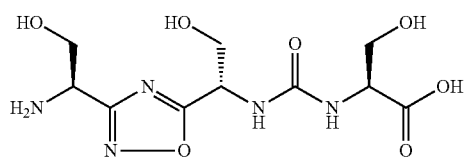 [SMILES: N[C@@H](CO)c1noc([C@H](CO)NC(=O)N[C@@H](CO)C(=O)O)n1]

or a pharmaceutically acceptable salt thereof.

9. The method of claim 1, wherein the compound is

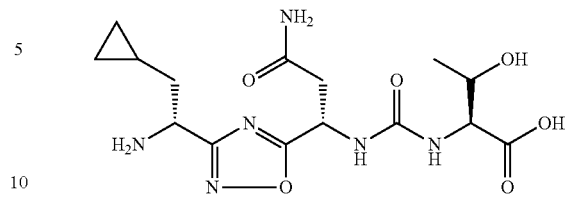

or a pharmaceutically acceptable salt thereof.

10. The method of claim 1, wherein the compound is

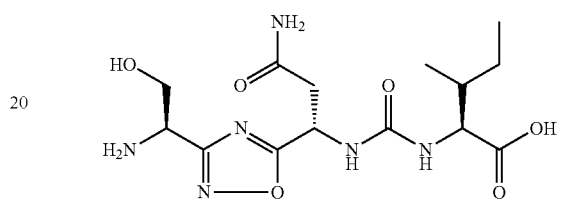

or a pharmaceutically acceptable salt thereof.

11. The method of claim 1, wherein the compound is

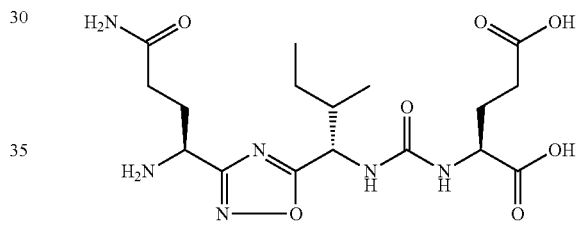

or a pharmaceutically acceptable salt thereof.

12. The method of claim 1, wherein the compound is

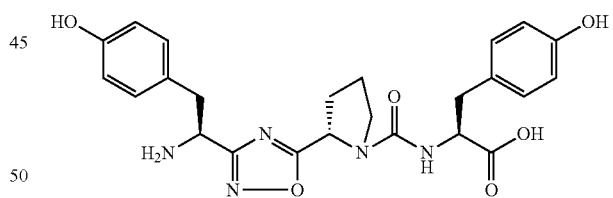

or a pharmaceutically acceptable salt thereof.

13. The method of claim 1, wherein the compound is

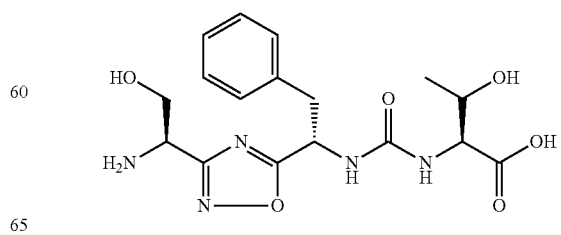

or a pharmaceutically acceptable salt thereof.

14. The method of claim 1, wherein the compound is

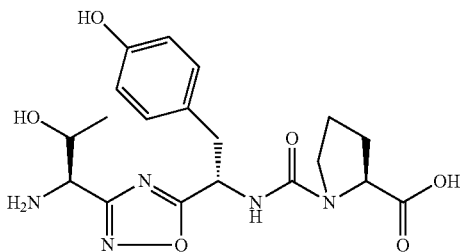 [SMILES: CC(O)[C@H](N)c1noc([C@H](Cc2ccc(O)cc2)NC(=O)N2CCC[C@H]2C(=O)O)n1]

or a pharmaceutically acceptable salt thereof.

15. The method of claim 1, wherein the compound is

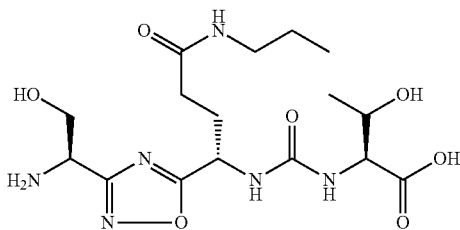 [SMILES: CCCNC(=O)CC[C@H](NC(=O)N[C@H](C(=O)O)C(C)O)c1nc([C@@H](N)CO)no1]

or a pharmaceutically acceptable salt thereof.

16. The method of claim 1, wherein the compound is

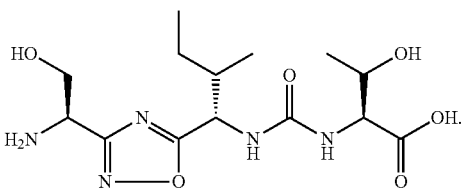

17. The method of claim 1, wherein the compound is

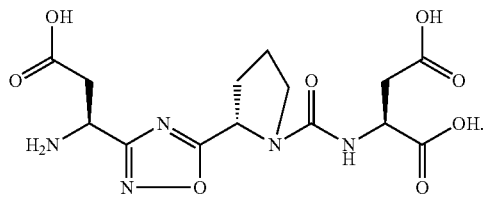 [SMILES: N[C@@H](CC(=O)O)c1noc([C@@H]2CCCN2C(=O)N[C@@H](CC(=O)O)C(=O)O)n1]

18. The method of claim 1, wherein the compound is

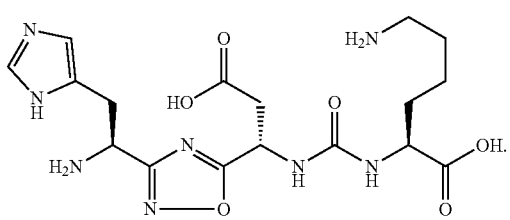 [SMILES: NCCCC[C@H](NC(=O)N[C@@H](CC(=O)O)c1nc([C@@H](N)Cc2cnc[nH]2)no1)C(=O)O]

19. The method of claim 1, wherein the compound is

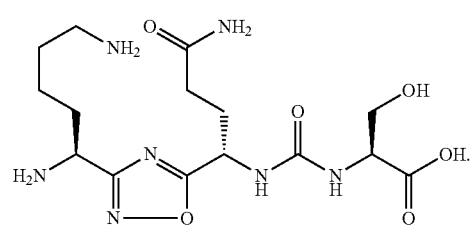

20. The method of claim 1, wherein the compound is

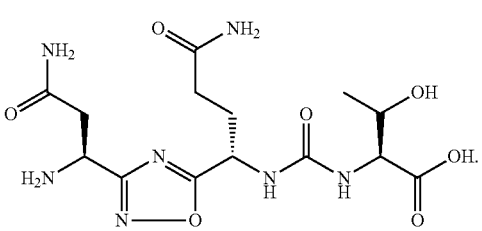 [SMILES: CC(O)[C@H](NC(=O)N[C@@H](CCC(N)=O)c1nc([C@@H](N)CC(N)=O)no1)C(=O)O]

21. The method of claim 1, wherein the compound is

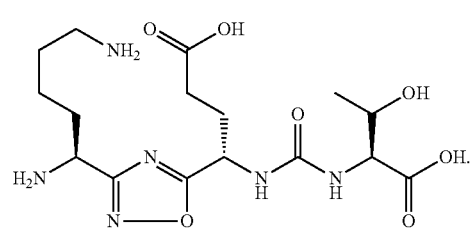 [SMILES: CC(O)[C@H](NC(=O)N[C@@H](CCC(=O)O)c1nc([C@@H](N)CCCCN)no1)C(=O)O]

22. The method of claim 1, wherein the compound is

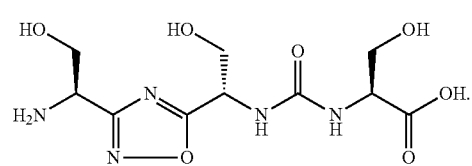

23. The method of claim 1, wherein the compound is

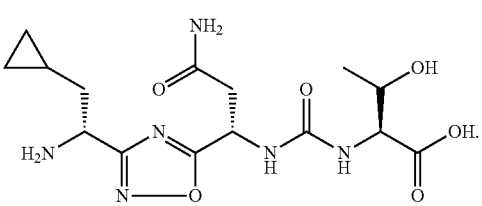 [SMILES: CC(O)[C@H](NC(=O)N[C@@H](CC(N)=O)c1nc([C@H](N)CC2CC2)no1)C(=O)O]

24. The method of claim 1, wherein the compound is

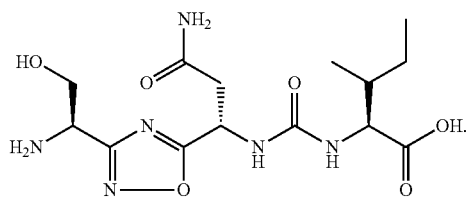 [SMILES: CCC(C)[C@H](NC(=O)N[C@@H](CC(N)=O)c1nc([C@@H](N)CO)no1)C(=O)O]

25. The method of claim 1, wherein the compound is

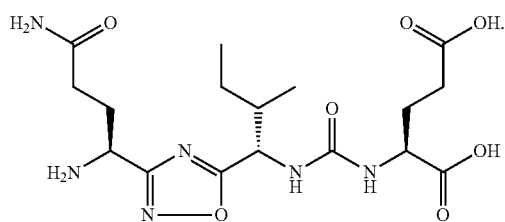 [SMILES: CCC(C)[C@H](NC(=O)N[C@@H](CCC(=O)O)C(=O)O)c1nc([C@@H](N)CCC(N)=O)no1]

26. The method of claim 1, wherein the compound is

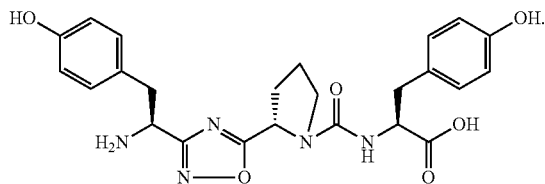 [SMILES: N[C@@H](Cc1ccc(O)cc1)c1noc([C@@H]2CCCN2C(=O)N[C@@H](Cc2ccc(O)cc2)C(=O)O)n1]

27. The method of claim 1, wherein the compound is

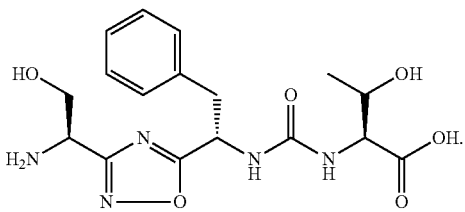 [SMILES: CC(O)[C@H](NC(=O)N[C@@H](Cc1ccccc1)c1nc([C@@H](N)CO)no1)C(=O)O]

28. The method of claim 1, wherein the compound is

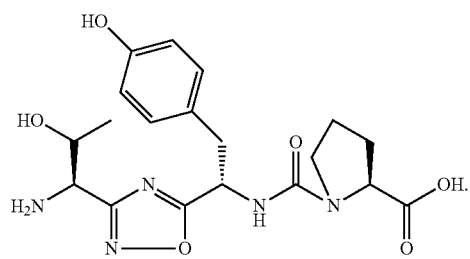 [SMILES: CC(O)[C@H](N)c1noc([C@H](Cc2ccc(O)cc2)NC(=O)N2CCC[C@H]2C(=O)O)n1]

29. The method of claim 1, wherein the compound is

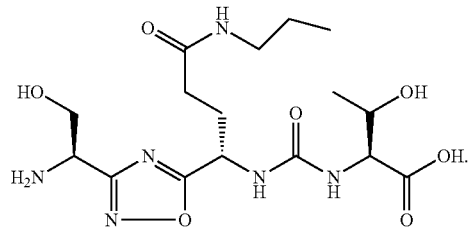 [SMILES: CCCNC(=O)CC[C@H](NC(=O)N[C@H](C(=O)O)C(C)O)c1nc([C@@H](N)CO)no1]

30. The method of claim 1, wherein the cancer is selected from lung cancer, breast cancer, colon cancer, renal cancer, bladder cancer, thyroid cancer, prostate cancer, osteosarcoma, or Hodgkin's lymphoma.

\* \* \* \* \*